(12) United States Patent
McNair et al.

(10) Patent No.: US 10,957,449 B1
(45) Date of Patent: Mar. 23, 2021

(54) DETERMINING NEW KNOWLEDGE FOR CLINICAL DECISION SUPPORT

(71) Applicant: Cerner Innovation, Inc., Kansas City, KS (US)

(72) Inventors: Douglas S. McNair, Leawood, KS (US); John Christopher Murrish, Overland Park, KS (US); Kanakasabha Kailasam, Olathe, KS (US)

(73) Assignee: Cerner Innovation, Inc.

( * ) Notice: Subject to any disclaimer, the term of this patent is extended or adjusted under 35 U.S.C. 154(b) by 0 days.

(21) Appl. No.: 14/148,046

(22) Filed: Jan. 6, 2014

Related U.S. Application Data

(60) Provisional application No. 61/864,992, filed on Aug. 12, 2013.

(51) Int. Cl.
G16H 50/20 (2018.01)
(52) U.S. Cl.
CPC .................................... *G16H 50/20* (2018.01)
(58) Field of Classification Search
CPC ....................................................... G16H 50/20
See application file for complete search history.

(56) References Cited

U.S. PATENT DOCUMENTS

| | | |
|---|---|---|
| 4,839,853 A | 6/1989 | Deerwester et al. |
| 5,243,565 A | 9/1993 | Yamamoto |

(Continued)

FOREIGN PATENT DOCUMENTS

| | | |
|---|---|---|
| EP | 1043666 A2 | 10/2000 |
| EP | 2365456 A2 | 9/2011 |

(Continued)

OTHER PUBLICATIONS

Byron Cook and Eric Koskinen, "Making Prophecies with Decision Predicates", Jan. 2011, ACM 978-1-4503-0490-0/11/01 (Year : 2011).*

(Continued)

*Primary Examiner* — Evangeline Barr
(74) *Attorney, Agent, or Firm* — Shook, Hardy & Bacon L.L.P.

(57) ABSTRACT

Systems, methods and computer-readable media are provided for facilitating clinical decision support and managing patient population health by health-related entities including caregivers, health care administrators, insurance providers, and patients. Embodiments of the invention provide decision support services including providing timely contextual patient information including condition risks, risk factors and relevant clinical information that are dynamically updatable; imputing missing patient information; dynamically generating assessments for obtaining additional patient information based on context; data-mining and information discovery services including discovering new knowledge; identifying or evaluating treatments or sequences of patient care actions and behaviors, and providing recommendations based on this; intelligent, adaptive decision support services including identifying critical junctures in patient care processes, such as points in time that warrant close attention by caregivers; near-real time querying across diverse health records data sources, which may use diverse clinical nomenclatures and ontologies; improved natural language processing services; and other decision support services.

21 Claims, 46 Drawing Sheets

(56) References Cited

U.S. PATENT DOCUMENTS

| | | |
|---|---|---|
| 5,301,109 A | 4/1994 | Landauer et al. |
| 5,664,109 A | 9/1997 | Johnson et al. |
| 5,809,494 A | 9/1998 | Nguyen |
| 5,835,900 A | 11/1998 | Fagg et al. |
| 6,039,688 A | 3/2000 | Douglas et al. |
| 6,246,964 B1 | 6/2001 | Blaunstein |
| 6,246,975 B1 | 6/2001 | Rivonelli et al. |
| 6,247,004 B1 | 6/2001 | Moukheibir |
| 6,397,224 B1 | 5/2002 | Zubeldia et al. |
| 6,618,715 B1 | 9/2003 | Johnson et al. |
| 6,654,740 B2 | 11/2003 | Tokuda et al. |
| 6,665,669 B2 | 12/2003 | Han et al. |
| 6,996,575 B2 | 2/2006 | Cox et al. |
| 7,039,634 B2 | 5/2006 | Xu et al. |
| 7,120,626 B2 | 10/2006 | Li et al. |
| 7,249,117 B2 | 7/2007 | Estes |
| 7,440,947 B2 | 10/2008 | Adcock et al. |
| 7,447,643 B1 | 11/2008 | Olson et al. |
| 7,496,561 B2 * | 2/2009 | Caudill ............... G06F 17/3069 |
| 7,529,765 B2 | 5/2009 | Brants et al. |
| 7,555,425 B2 | 6/2009 | Oon |
| 7,558,778 B2 | 7/2009 | Carus et al. |
| 7,617,078 B2 | 11/2009 | Rao et al. |
| 7,640,171 B2 | 12/2009 | Gendron et al. |
| 7,657,540 B1 | 2/2010 | Bayliss |
| 7,668,820 B2 | 2/2010 | Zuleba |
| 7,720,846 B1 | 5/2010 | Bayliss |
| 7,831,423 B2 | 11/2010 | Schubert |
| 7,844,449 B2 | 11/2010 | Lin et al. |
| 7,844,566 B2 | 11/2010 | Wnek |
| 7,853,456 B2 | 12/2010 | Soto et al. |
| 7,865,373 B2 | 1/2011 | Punzak et al. |
| 7,899,764 B2 | 3/2011 | Martin et al. |
| 7,899,796 B1 | 3/2011 | Borthwick et al. |
| 7,900,052 B2 | 3/2011 | Jonas |
| 7,912,842 B1 | 3/2011 | Bayliss |
| 7,933,909 B2 | 4/2011 | Trepetin |
| 7,953,685 B2 | 5/2011 | Liu et al. |
| 8,078,554 B2 | 12/2011 | Fung et al. |
| 8,126,736 B2 | 2/2012 | Anderson et al. |
| 8,160,895 B2 | 4/2012 | Schmitt et al. |
| 8,165,893 B1 | 4/2012 | Goldberg et al. |
| 8,200,505 B2 | 6/2012 | Walker et al. |
| 8,515,777 B1 | 8/2013 | Rajasenan |
| 8,539,424 B2 | 9/2013 | Tetelbaum |
| 8,589,424 B1 | 11/2013 | Patel et al. |
| 8,666,785 B2 | 3/2014 | Baluta et al. |
| 8,838,628 B2 | 9/2014 | Leighton et al. |
| 8,856,156 B1 | 10/2014 | McNair et al. |
| 9,375,142 B2 | 6/2016 | Schultz et al. |
| 9,542,647 B1 | 1/2017 | Mirhaji |
| 9,734,146 B1 | 8/2017 | McNair et al. |
| 10,249,385 B1 | 4/2019 | McNair et al. |
| 10,268,687 B1 | 4/2019 | McNair et al. |
| 10,431,336 B1 | 10/2019 | Murrish et al. |
| 10,628,553 B1 | 4/2020 | Murrish et al. |
| 2002/0032583 A1 | 3/2002 | Joao |
| 2002/0035486 A1 | 3/2002 | Huyn et al. |
| 2002/0038227 A1 | 3/2002 | Fey et al. |
| 2002/0038308 A1 | 3/2002 | Cappi |
| 2002/0042793 A1 | 4/2002 | Choi |
| 2002/0073138 A1 | 6/2002 | Gilbert et al. |
| 2002/0128860 A1 | 9/2002 | Leveque et al. |
| 2003/0023571 A1 | 1/2003 | Barnhill |
| 2003/0038308 A1 | 2/2003 | Kim |
| 2003/0163057 A1 | 8/2003 | Flick et al. |
| 2003/0212580 A1 | 11/2003 | Shen |
| 2004/0199332 A1 | 10/2004 | Iliff |
| 2004/0230105 A1 | 11/2004 | Geva et al. |
| 2004/0260666 A1 | 12/2004 | Pestotnik et al. |
| 2005/0027562 A1 | 2/2005 | Brown |
| 2005/0049497 A1 | 3/2005 | Krishnan et al. |
| 2005/0119534 A1 * | 6/2005 | Trost ............... G06F 19/3456 600/300 |
| 2005/0144042 A1 | 6/2005 | Joffe et al. |
| 2005/0288910 A1 | 12/2005 | Schlessinger et al. |
| 2006/0020465 A1 | 1/2006 | Cousineau et al. |
| 2006/0064447 A1 | 3/2006 | Malkov |
| 2006/0129427 A1 * | 6/2006 | Wennberg ............. G06F 19/328 705/2 |
| 2006/0161457 A1 | 7/2006 | Rapaport et al. |
| 2006/0173663 A1 | 8/2006 | Langheier |
| 2006/0205564 A1 | 9/2006 | Peterson |
| 2006/0206027 A1 | 9/2006 | Malone |
| 2006/0206359 A1 | 9/2006 | Stang |
| 2006/0218010 A1 | 9/2006 | Michon et al. |
| 2006/0271556 A1 | 11/2006 | Mukherjee et al. |
| 2007/0005621 A1 | 1/2007 | Lesh et al. |
| 2007/0026365 A1 | 2/2007 | Friedrich et al. |
| 2007/0031873 A1 | 2/2007 | Wang et al. |
| 2007/0094048 A1 | 4/2007 | Grichnik |
| 2007/0106533 A1 | 5/2007 | Greene |
| 2007/0106752 A1 | 5/2007 | Moore |
| 2007/0233391 A1 | 10/2007 | Milstein et al. |
| 2007/0239482 A1 | 10/2007 | Finn et al. |
| 2007/0244724 A1 * | 10/2007 | Pendergast ............ G06F 19/322 705/3 |
| 2008/0021288 A1 | 1/2008 | Bowman et al. |
| 2008/0046292 A1 | 2/2008 | Myers et al. |
| 2008/0097938 A1 | 4/2008 | Guyon et al. |
| 2008/0131374 A1 | 6/2008 | Medich et al. |
| 2008/0133269 A1 | 6/2008 | Ching |
| 2008/0147441 A1 | 6/2008 | Kil |
| 2008/0172214 A1 | 7/2008 | Col et al. |
| 2008/0172251 A1 | 7/2008 | Reichert et al. |
| 2008/0183454 A1 | 7/2008 | Barabasi et al. |
| 2008/0195422 A1 | 8/2008 | Nessinger et al. |
| 2008/0243548 A1 | 10/2008 | Cafer |
| 2008/0249376 A1 | 10/2008 | Zaleski et al. |
| 2008/0255884 A1 | 10/2008 | Carus et al. |
| 2008/0256006 A1 | 10/2008 | Buscema et al. |
| 2008/0268413 A1 | 10/2008 | Leichner |
| 2008/0275731 A1 | 11/2008 | Rao et al. |
| 2008/0287746 A1 | 11/2008 | Reisman |
| 2008/0288292 A1 | 11/2008 | Bi et al. |
| 2008/0288474 A1 | 11/2008 | Chin et al. |
| 2008/0294692 A1 | 11/2008 | Angell et al. |
| 2008/0301177 A1 | 12/2008 | Doherty |
| 2008/0306926 A1 | 12/2008 | Friedlander et al. |
| 2009/0006431 A1 | 1/2009 | Agrawal et al. |
| 2009/0012928 A1 | 1/2009 | Lussier et al. |
| 2009/0112892 A1 | 4/2009 | Cardie et al. |
| 2009/0125333 A1 * | 5/2009 | Heywood ............. A61B 5/0002 705/3 |
| 2009/0132284 A1 | 5/2009 | Fey et al. |
| 2009/0164249 A1 | 6/2009 | Hunt et al. |
| 2009/0228303 A1 | 9/2009 | Faulkner et al. |
| 2009/0259493 A1 | 10/2009 | Venon et al. |
| 2009/0299977 A1 | 12/2009 | Rosales |
| 2009/0304246 A1 | 12/2009 | Walker et al. |
| 2009/0318775 A1 | 12/2009 | Michelson et al. |
| 2009/0319295 A1 | 12/2009 | Kass-Hout et al. |
| 2010/0082369 A1 | 4/2010 | Prenelus et al. |
| 2010/0088117 A1 | 4/2010 | Belden |
| 2010/0121883 A1 | 5/2010 | Cutting et al. |
| 2010/0131434 A1 | 5/2010 | Magent et al. |
| 2010/0131438 A1 | 5/2010 | Pandya et al. |
| 2010/0131482 A1 | 5/2010 | Linthicum et al. |
| 2010/0131883 A1 | 5/2010 | Linthicum et al. |
| 2010/0142774 A1 | 6/2010 | Ben-Haim et al. |
| 2010/0145720 A1 | 6/2010 | Reiner |
| 2010/0179818 A1 | 7/2010 | Kelly et al. |
| 2010/0185685 A1 | 7/2010 | Chew et al. |
| 2010/0198755 A1 | 8/2010 | Soll et al. |
| 2010/0274576 A1 | 10/2010 | Young |
| 2010/0293003 A1 | 11/2010 | Abbo |
| 2010/0299155 A1 | 11/2010 | Findlay et al. |
| 2010/0324861 A1 | 12/2010 | Goulding et al. |
| 2010/0324938 A1 * | 12/2010 | Ennett .................. G06F 19/322 705/3 |
| 2011/0010401 A1 | 1/2011 | Adams et al. |
| 2011/0015937 A1 | 1/2011 | Janas et al. |
| 2011/0046979 A1 | 2/2011 | Tulipano et al. |
| 2011/0067108 A1 | 3/2011 | Hoglund |

(56) References Cited

U.S. PATENT DOCUMENTS

| | | | |
|---|---|---|---|
| 2011/0077973 | A1 | 3/2011 | Breitenstein et al. |
| 2011/0087501 | A1 | 4/2011 | Severin |
| 2011/0093467 | A1 | 4/2011 | Sharp et al. |
| 2011/0119089 | A1 | 5/2011 | Carlisle |
| 2011/0161110 | A1 | 6/2011 | Mault |
| 2011/0201900 | A1 | 8/2011 | Zhang et al. |
| 2011/0225001 | A1 | 9/2011 | Shen |
| 2011/0246238 | A1 | 10/2011 | Vdovjak et al. |
| 2011/0270629 | A1 | 11/2011 | Abbo |
| 2011/0295621 | A1 | 12/2011 | Farooq et al. |
| 2011/0306845 | A1 | 12/2011 | Osorio |
| 2012/0016685 | A1 | 1/2012 | Ryan et al. |
| 2012/0020536 | A1 | 1/2012 | Moehrle |
| 2012/0047105 | A1 | 2/2012 | Saigal et al. |
| 2012/0059779 | A1 | 3/2012 | Syed et al. |
| 2012/0072235 | A1 | 3/2012 | Varadarajan et al. |
| 2012/0078127 | A1 | 3/2012 | McDonald et al. |
| 2012/0086963 | A1 | 4/2012 | Fujitsuka et al. |
| 2012/0089420 | A1 | 4/2012 | Hoffman et al. |
| 2012/0089421 | A1 | 4/2012 | Hoffman et al. |
| 2012/0110016 | A1 | 5/2012 | Phillips |
| 2012/0173475 | A1* | 7/2012 | Ash .................. G06F 17/30563 707/600 |
| 2012/0174014 | A1 | 7/2012 | Ash et al. |
| 2012/0174018 | A1 | 7/2012 | Ash et al. |
| 2012/0175475 | A1 | 7/2012 | McErlane |
| 2012/0203575 | A1 | 8/2012 | Tulipano et al. |
| 2012/0215784 | A1 | 8/2012 | King et al. |
| 2012/0232930 | A1 | 9/2012 | Schmidt et al. |
| 2012/0246102 | A1 | 9/2012 | Sudharsan |
| 2013/0006911 | A1 | 1/2013 | Christie, IV et al. |
| 2013/0023434 | A1 | 1/2013 | Van Laar |
| 2013/0046529 | A1 | 2/2013 | Grain |
| 2013/0046558 | A1 | 2/2013 | Landi et al. |
| 2013/0110547 | A1 | 5/2013 | Englund et al. |
| 2013/0110548 | A1 | 5/2013 | Kutty |
| 2013/0132312 | A1 | 5/2013 | Lee et al. |
| 2013/0132323 | A1 | 5/2013 | Soto et al. |
| 2013/0197938 | A1 | 8/2013 | Bayouk et al. |
| 2013/0245389 | A1 | 9/2013 | Schultz et al. |
| 2014/0095184 | A1 | 4/2014 | Gotz et al. |
| 2014/0095186 | A1* | 4/2014 | Gotz .................. G06Q 10/0635 705/2 |
| 2014/0180699 | A1 | 6/2014 | Massa et al. |
| 2014/0181128 | A1 | 6/2014 | Riskin et al. |
| 2014/0200414 | A1 | 7/2014 | Osorio |
| 2014/0336539 | A1 | 11/2014 | Torres et al. |
| 2015/0049947 | A1 | 2/2015 | Katsaros et al. |
| 2015/0161329 | A1 | 6/2015 | Mabotuwana et al. |
| 2015/0254408 | A1 | 9/2015 | Mahtani et al. |
| 2015/0324535 | A1 | 11/2015 | Ash et al. |
| 2015/0363559 | A1 | 12/2015 | Jackson et al. |
| 2016/0004840 | A1 | 1/2016 | Rust et al. |
| 2016/0063212 | A1 | 3/2016 | Monier et al. |
| 2016/0143594 | A1 | 5/2016 | Moorman et al. |

FOREIGN PATENT DOCUMENTS

| | | |
|---|---|---|
| WO | 2012/122122 A1 | 9/2012 |
| WO | 2012122195 A1 | 9/2012 |
| WO | 2012122196 A1 | 9/2012 |

OTHER PUBLICATIONS

Abbott A, Tsay A. Sequence Analysis and Optimal Matching Methods in Sociology, Review and Prospect. Sociol Meth Res 2000;29:3-33.

Agrawal R, et al. 'Fast Discovery of Association Rules.' In Fayyad U, et al., eds., Advances in Knowledge Discovery and Data Mining, pp. 307-328. Menlo Park, AAAI Press, 1996.

Berchtold A, Raftery A. The Mixture Transition Distribution Model for High-Order Markov Chains and Non-Gaussian Time Series. Stat Sci 2002;17:328-56.

Billari F, et al. Timing, Sequencing, and quantum of Life Course Events: A Machine-Learning Approach. Eur J Pop 2006;22:37-65.

Deville J, Saporta G. Correspondence Analysis with an Extension Towards Nominal Time Series. J Econometrics 1983;22:169-89.

Dijkstra W, Taris T. Measuring the Agreement Between Sequences. Sociol Meth Res 1995;24:214-31.

Dvorak J, et al. Risk Factor Analysis for Injuries in Football Players: Possibilities for a Prevention Program. Am J Sports Med. 2000;28:S69-74.

Dvorak J, Junge A. Football Injuries and Physical Symptoms: A Review of the Literature. Am J Sports Med 2000;28:S3-9.

Han J-W, et al. Frequent Pattern Mining: Current status and future directions. Data Mining and Knowledge Discovery 2007;15:55-86.

Hawkins R, Fuller C. A Prospective Eidemiological Study of Injuries in Four English Professional Football Clubs. Br J Sports Med 1999;33:196-203.

Junge A, Dvorak J. Soccer Injuries: A Review on Incidence and Prevention. Sports Med. 2004;34:929-38.

Nielsen A, Yde J. Epidemiology and Traumatology of Injuries in Soccer. Am J Sports Med 1989;17:803-7.

Zaki M. Spade: An Efficient Algorithm for Mining Frequent Sequences. Machine Learning 2001;42:31-60.

Huyse, Frits et al., Compri-An Instrument to Detect Patients With Complex Care Needs; Psychosomatics 42:3, May-Jun. 2001; 7 pages.

Berry, Leonard et al., Care Coordination for Patients With Complex Health Profiles in Inpatients and Outpatient Settings; Mayo Clinic Proceedings; www.mayoclinicproceedings.org; Jan. 11, 2013; 11 pages.

Cohen, Eyal et al., Integrated Complex Care Coordination for Children With Medical Complexity: A Mixed-Methods Evaluation of Tertiary Care-Community Collaboration; BioMed Central the Open Access Publisher; www.biomedcentral.com/1472-6963/12/366; Oct. 23, 2012; 23 pages.

Nealon, et al.: Agent-Based Applications in Health Care, Department of Computing, Oxford Brookes University and Computer Science and Mathematics Department, University Rovira I Virgill, 17 pages.

Kang, et al.: Mining Based Decision Support Multi-agent System for Personalized e-Healthcare Service*, Schook of Computer Engineering, Sungkyunkwan University, 10 pages.

Mabry, et al.: Clinical Decision Support with IM-Agents and ERMA Multi-agents, Department of Computer Science and Emergency Medicine, 6 pages.

First Action Interview Preinterview Communication dated Jan. 3, 2013 in U.S. Appl. No. 13/250,072, 8 pages.

First Action Interview Office Action dated Oct. 8, 2013 in U.S. Appl. No. 13/250,072, 5 pages.

Final Office Action dated Jun. 2, 2014 in U.S. Appl. No. 13/250,072, 15 pages.

Non-Final Office Action dated Mar. 2, 2015 in U.S. Appl. No. 13/250,072, 14 pages.

Final Office Action dated Sep. 28, 2015 in U.S. Appl. No. 13/250,072, 15 pages.

First Action Interview Preinterview Communication dated Feb. 10, 2014 in U.S. Appl. No. 13/269,244, 5 pages.

First Action Interview Office Action dated Jun. 17, 2014 in U.S. Appl. No. 13/269,244, 5 pages.

Non-Final Office Action dated Dec. 5, 2014 in U.S. Appl. No. 13/269,244, 18 pages.

Final Office Action dated Jul. 13, 2015 in U.S. Appl. No. 13/269,244, 21 pages.

First Action Interview Preinterview Communication dated Mar. 28, 2013 in U.S. Appl. No. 13/269,262, 4 pages.

First Action Interview Office Action dated Oct. 11, 2013 in U.S. Appl. No. 13/269,262, 5 pages.

Final Office Action dated Jun. 2, 2014 in U.S. Appl. No. 13/269,262, 14 pages.

Non-Final Office Action dated May 22, 2015 in U.S. Appl. No. 13/963,732, 14 pages.

Non-Final Office Action dated Sep. 1, 2015 in U.S. Appl. No. 13/874,961, 33 pages.

(56) References Cited

OTHER PUBLICATIONS

First Action Interview Preinterview Communication dated Dec. 27, 2013 in U.S. Appl. No. 13/647,187, 7 pages.
First Action Interview Office Action dated Apr. 3, 2014 in U.S. Appl. No. 13/647,187, 10 pages.
Final Office Action dated Sep. 29, 2014 in U.S. Appl. No. 13/647,187, 21 pages.
Non-Final Office Action dated Aug. 31, 2015 in U.S. Appl. No. 13/647,187, 16 pages.
International Search Report and Written Opinion dated Nov. 26, 2014 in Application No. PCT/US2014/050735, 11 pages.
First Action Interview Preinterview Communication dated Jun. 30, 2015 in U.S. Appl. No. 14/147,978, 5 pages.
First Action Interview Preinterview Communication dated Jul. 30, 2015 in U.S. Appl. No. 14/147,991, 5 pages.
First Action Interview Preinterview Communication dated Aug. 11, 2015 in U.S. Appl. No. 14/148,002, 5 pages.
First Action Interview Preinterview Communication dated Aug. 13, 2015 in U.S. Appl. No. 14/148,020, 5 pages.
First Action Interview Preinterview Communication dated Jun. 30, 2015 in U.S. Appl. No. 14/148,028, 5 pages.
First Action Interview Preinterview Communication dated Jul. 17, 2015 in U.S. Appl. No. 14/148,039, 4 pages.
First Action Interview Preinterview Communication dated Aug. 14, 2015 in U.S. Appl. No. 14/148,050, 5 pages.
First Action Interview Preinterview Communication dated Aug. 11, 2015 in U.S. Appl. No. 14/148,059, 5 pages.
Non-Final Office Action dated Aug. 5, 2015 in U.S. Appl. No. 14/477,284, 11 pages.
First Action Interview Preinterview Communication dated Sep. 26, 2012 in U.S. Appl. No. 12/982,131, 4 pages.
Final Office Action dated Apr. 24, 2013 in U.S. Appl. No. 12/982,131, 25 pages.
Non-Final Office Action dated Dec. 20, 2013 in U.S. Appl. No. 12/982,131, 19 pages.
Final Office Action dated Nov. 7, 2014 in U.S. Appl. No. 12/982,131, 17 pages.
Notice of Allowance dated Apr. 9, 2015 in U.S. Appl. No. 12/982,131, 12 pages.
First Action Interview Preinterview Communication dated Sep. 26, 2012 in U.S. Appl. No. 12/982,137, 4 pages.
Final Office Action dated May 8, 2013 in U.S. Appl. No. 12/982,137, 22 pages.
Notice of Allowance dated Nov. 14, 2013 in U.S. Appl. No. 12/982,137, 15 pages.
First Action Interview Preinterview Communication dated Oct. 4, 2012 in U.S. Appl. No. 12/982,143, 5 pages.
First Action Interview Office Action dated Nov. 21, 2012 in U.S. Appl. No. 12/982,143, 7 pages.
Final Office Action dated May 1, 2013 in U.S. Appl. No. 12/982,143, 22 pages.
Non-Final Office Action dated Oct. 2, 2013 in U.S. Appl. No. 12/982,143, 24 pages.
Notice of Allowance dated Jun. 4, 2014 in U.S. Appl. No. 13/645,896, 11 pages.
Murat Sariyar and Andreas Borg, The Recordlinkage Package: Detecting Errors in Data, Dec. 2010, The R Journal vol. 212, pp. 61-67.
Christian Roever, Package 'bspec', Feb. 21, 2013, r-project.org, pp. 1-27.
Ohno-Machado, Lucila; "Realizing the full potential of electronic health records: the role of natural language processing", Sep. 2011, Journal of American Medical Information Association, vol. 18 No. 5, p. 539.
International Preliminary Report on Patentability dated Feb. 25, 2016 in Application No. PCT/US2014/050735, 9 pages.
Final Office Action dated Dec. 4, 2015 in U.S. Appl. No. 13/963,732, 21 pages.
First Action Interview Office Action dated Dec. 3, 2015 in U.S. Appl. No. 14/147,978, 8 pages.
First Action Interview Office Action dated Jan. 20, 2016 in U.S. Appl. No. 14/147,991, 8 pages.
First Action Interview Office Action dated Jan. 15, 2016 in U.S. Appl. No. 14/148,002, 8 pages.
First Action Interview Office Action dated Jan. 6, 2016 in U.S. Appl. No. 14/148,020, 8 pages.
First Action Interview Office Action dated Dec. 22, 2015 in U.S. Appl. No. 14/148,028, 8 pages.
First Action Interview Office Action dated Nov. 19, 2015 in U.S. Appl. No. 14/148,039, 8 pages.
First Action Interview Office Action dated Jan. 22, 2016 in U.S. Appl. No. 14/148,050, 8 pages.
First Action Interview Office Action dated Dec. 17, 2015 in U.S. Appl. No. 14/148,059, 8 pages.
Non-Final Office Action dated Mar. 10, 2016 in U.S. Appl. No. 13/269,244, 28 pages.
First Action Interview Preinterview Communication dated Mar. 10, 2016 in U.S. Appl. No. 14/175,750, 4 pages.
Notice of Allowance dated Mar. 11, 2016 in U.S. Appl. No. 14/477,284, 6 pages.
Non-Final Office Action dated Mar. 30, 2016 in U.S. Appl. No. 13/250,072, 12 pages.
Final Office Action dated May 3, 2016 in U.S. Appl. No. 13/647,187, 19 pages.
Final Office Action dated Sep. 8, 2016 in U.S. Appl. No. 14/148,002, 24 pages.
Final Office Action dated Sep. 9, 2016 in U.S. Appl. No. 14/148,050, 23 pages.
Final Office Action dated Sep. 23, 2016 in U.S. Appl. No. 14/148,059, 27 pages.
Final Office Action dated Sep. 26, 2016 in U.S. Appl. No. 13/269,244, 35 pages.
Final Office Action dated Nov. 2, 2016 in U.S. Appl. No. 13/874,961, 18 pages.
Final Office Action dated Dec. 15, 2016 in U.S. Appl. No. 13/250,072, 18 pages.
Non-Final Office Action dated Jan. 13, 2017 in U.S. Appl. No. 13/647,187, 20 pages.
Final Office Action dated Feb. 16, 2017 in U.S. Appl. No. 14/175,750, 13 pages.
European Search Report dated Mar. 13, 2017 in European Patent Application No. 14835964, 9 pages.
Final Office Action dated May 12, 2017 in U.S. Appl. No. 13/963,732, 20 pages.
Non-Final Office Action dated May 18, 2017 in U.S. Appl. No. 14/147,978, 29 pages.
Non-Final Office Action dated Jun. 6, 2017 in U.S. Appl. No. 14/148,059, 30 pages.
Final Office Action dated Jun. 28, 2016 in U.S. Appl. No. 13/874,961, 19 pages.
Final Office Action dated Jul. 1, 2016 in U.S. Appl. No. 14/147,978, 25 pages.
Final Office Action dated Jul. 14, 2016 in U.S. Appl. No. 14/148,028, 28 pages.
Final Office Action dated Jul. 20, 2016 in U.S. Appl. No. 14/148,039, 32 pages.
Non-Final Office Action dated Jul. 26, 2016 in U.S. Appl. No. 13/963,732, 16 pages.
Final Office Action dated Jul. 29, 2016 in U.S. Appl. No. 14/148,020, 23 pages.
Notice of Allowance dated Aug. 2, 2016 in U.S. Appl. No. 14/477,284, 7 pages.
Final Office Action dated Aug. 15, 2016 in U.S. Appl. No. 14/147,991, 34 pages.
First Action Interview Office Action dated Aug. 17, 2016 in U.S. Appl. No. 14/175,750, 5 pages.
Non-Final Office Action dated Sep. 1, 2016 in U.S. Appl. No. 14/209,568, 12 pages.
Non-Final Office Action dated Sep. 22, 2017 in U.S. Appl. No. 14/175,750, 10 pages.
Non-Final Office Action dated Oct. 2, 2017 in U.S. Appl. No. 13/250,072, 8 pages.

(56) References Cited

OTHER PUBLICATIONS

First Action Interview Pre-Interview Communication dated Dec. 8, 2017 in U.S. Appl. No. 14/792,736, 22 pages.
Final Office Action dated Dec. 11, 2017 in U.S. Appl. No. 14/148,059, 27 pages.
Non-Final Office Action dated Dec. 27, 2017 in U.S. Appl. No. 13/963,732, 18 pages.
Final Office Action dated Jan. 4, 2018 in U.S. Appl. No. 14/147,991, 35 pages.
Final Office Action dated Jan. 5, 2018 in U.S. Appl. No. 14/148,028, 44 pages.
Final Office dated Jan. 18, 2018 in U.S. Appl. No. 14/147,978, 28 pages.
Final Office Action dated Jan. 26, 2018 in U.S. Appl. No. 14/148,039, 33 pages.
Final Office Action dated Feb. 16, 2018 in U.S. Appl. No. 14/281,593, 15 pages.
Non-Final Office Action dated Mar. 2, 2018 in U.S. Appl. No. 14/209,568, 23 pages.
Non-Final Office Action received for U.S. Appl. No. 14/148,059, dated Apr. 26, 2019, 28 pages.
Non-Final Office Action received for U.S. Appl. No. 14/792,736, dated Apr. 11, 2019, 18 pages.
Non-Final Office Action received for U.S. Appl. No. 14/982,982, dated May 14, 2019, 9 pages.
Aronson, Alan R., "MetaMap: Mapping Text to the UMLS Metathesaurus", 2006, pp. 1-26.
Final Office action received for U.S. Appl. No. 13/647,187, dated Dec. 14, 2018, 28 pages.
Non-Final Office Action received for U.S. Appl. No. 14/147,991, dated Nov. 27, 2018, 37 pages.
Final Office Action received for U.S. Appl. No. 14/555,058, dated Sep. 7, 2018, 19 pages.
Final Office Action received for U.S. Appl. No. 14/792,736, dated Oct. 15, 2018, 18 pages.
Non-Final Office Action received for U.S. Appl. No. 14/147,978, dated Sep. 28, 2018, 29 pages.
Non-Final Office Action received for U.S. Appl. No. 14/555,058, dated Dec. 29, 2017, 13 pages.
Non-Final Office Action received for U.S. Appl. No. 13/647,187, dated Apr. 13, 2018, 27 Pages.
Non-Final Office Action received for U.S. Appl. No. 14/148,059, dated Jun. 28, 2018, 27 Pages.
Non-Final Office Action received for U.S. Appl. No. 15/392,928, dated May 3, 2018, 15 Pages.
Notice of Allowance received for U.S. Appl. No. 13/874,961, dated Oct. 15, 2018, 9 pages.
Kiran, et al., "An improved multiple minimum support based approach to mine rare association rules", Computational Intelligence and Data Mining, 2009, 8 pages.
Arpaia et al., "Multi-Agent Remote Predictive Diagnosis of Dangerous Good Transports", Instrumentation and Measurement Technology Conference, Proceedings of the IEEE, May 17-19, 2005, pp. 1685-1690.
Non Final Office Action received for U.S. Appl. No. 14/555,058, dated Jun. 25, 2019, 20 pages.
Non-Final Office Action received for U.S. Appl. No. 13/963,732, dated Jul. 11, 2019, 13 pages.
Final Office Action received for U.S. Appl. No. 14/148,020, dated Oct. 9, 2019, 25 pages.
Preinterview First Office Action received for U.S. Appl. No. 15/855,720, dated Oct. 3, 2019, 4 pages.
Non-Final Office Action received for U.S. Appl. No. 13/269,244, dated Apr. 8, 2020, 17 pages.
Final Office Action received for U.S. Appl. No. 14/555,058, dated Feb. 12, 2020, 22 pages.
First Action Interview Office Action received for U.S. Appl. No. 15/386,876, dated Jan. 28, 2020, 24 pages.
Final Office Action received for U.S. Appl. No. 13/269,244, dated Aug. 12, 2020, 18 pages.
Final Office Action received for U.S. Appl. No. 14/148,059, dated Jul. 16, 2020, 16 pages.
Final Office Action received for U.S. Appl. No. 15/855,720, dated Jul. 2, 2020, 15 pages.
Notice of Allowance received for U.S. Appl. No. 14/148,020, dated Jul. 22, 2020, 10 pages.
Appavoo et al., "Enabling Autonomic Behavior in Systems Software With Hot Swapping", IBM Systems Journal, vol. 42, No. 1, 2003, pp. 60-76.
Townsend, Hilary, "Natural Language Processing and Clinical Outcomes: The Promise and Progress of NLP for Improved Care", Journal of AHIMA, vol. 84, No. 2, Available online at: <https://bok.ahima.org/doc?oid=106198#. X0SgnSgzY2x>, Mar. 2013, 3 pages.
Final Office Action dated Jun. 16, 2017 in U.S. Appl. No. 14/209,568, 20 pages.
First Action Interview Preinterview Communication dated Jun. 21, 2017 in U.S. Appl. No. 14/281,593, 4 pages.
Non-Final Office Action dated Jun. 28, 2017 in U.S. Appl. No. 14/148,046, 31 pages.
Non-Final Office Action dated Jul. 5, 2017 in U.S. Appl. No. 14/147,991, 36 pages.
Non-Final Office Action dated Jul. 24, 2017 in U.S. Appl. No. 14/148,020, 22 pages.
Supplemental Notice of Allowability dated Jul. 26, 2017 in U.S. Appl. No. 14/477,284, 6 pages.
Final Office Action dated Jul. 27, 2017 in U.S. Appl. No. 13/647,187, 23 pages.
Non-Final Office Action dated Aug. 10, 2017 in U.S. Appl. No. 14/148,002, 26 pages.
First Action Interview Office Action dated Sep. 6, 2017 in U.S. Appl. No. 14/281,593, 7 pages.
Non-Final Office Action dated Jun. 21, 2017 in U.S. Appl. No. 14/148,039, 34 pages.
Non-Final Office Action dated Jul. 31, 2017 in U.S. Appl. No. 14/148,060, 24 pages.
Non-Final Office Action received for U.S. Appl. No. 16/819,890, dated Sep. 29, 2020, 12 pages.
Non-Final Office Action received for U.S. Appl. No. 15/386,876, dated Sep. 14, 2020, 15 pages.
Prados-Suarez et al., "Contextualized Access to Electronical Health Records in Cardiology", IEEE Transactions on Information Technology in Biomedicine, vol. 16, No. 3, May 2012, pp. 401-412.
Summons to Attend Oral Proceedings received for European Patent Application No. 14835964.9, mailed on Jan. 13, 2021, 12 pages.

\* cited by examiner

| EXAMPLE SOLVERS | |
|---|---|
| DISCOVERYTIME/COMPILETIME | RUNTIME |
| FREQUENT/RELEVANT ITEMSET MINING -- DX | TANIMOTO DISTANCE MATCHING -- DX |
| FREQUENT/RELEVANT ITEMSET MINING -- DX | DISCERN RECOMMENDER -- DX |
| MODEL MISSINGS-DELAYEDS -- DX | IMPUTE MISSINGS-DELAYEDS -- DX |
| FREQUENT/RELEVANT ITEMSET MINING -- RX | SEQUENCEING/DE-DUPING -- ORDS/QTNRS |
| FREQUENT/RELEVANT ITEMSET MINING -- RX | DISCERN RECOMMENDER -- RX |
| MODEL MISSINGS-DELAYEDS -- RX | IMPUTE VALUES FOR MISSINGS-DELAYEDS |
| MULTIVOCALITY CONCORDANCE MODULE(S) | CRONBACH ALPHA NOTIFY DISCORDS |

*FIG. 1E.*

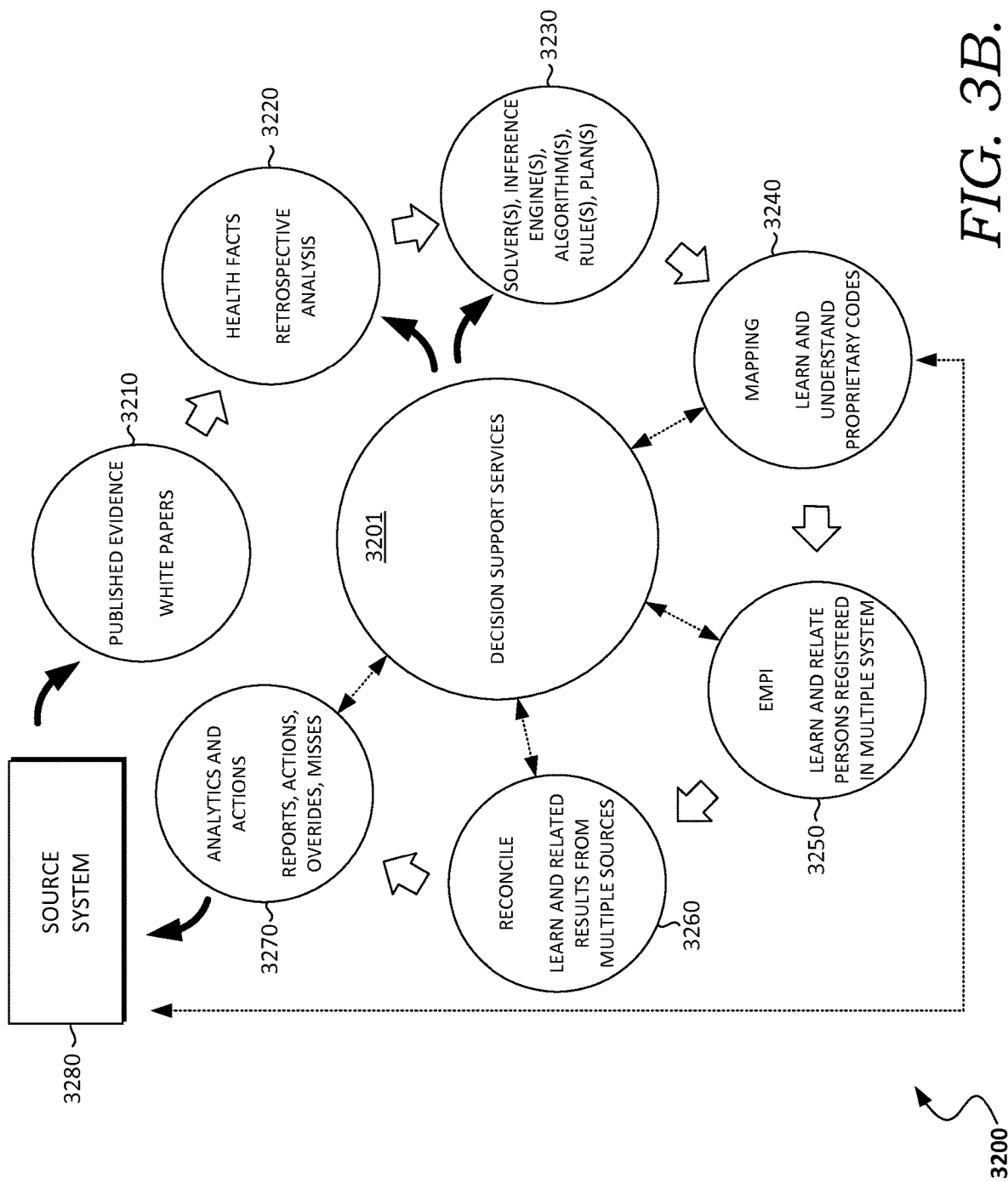

Panel 1

☐ CARE DECISIONS

DO YOU HAVE SWELLING IN YOUR ANKLES OR LEGS?
- ● NO
- ○ A LITTLE
- ○ SOME
- ○ A LOT

DOES YOUR HEART FAILURE MAKE YOU SLEEPING WELL AT NIGHT DIFFICULT?
- ● NO
- ○ A LITTLE
- ○ SOME
- ○ A LOT

DOES YOUR HEART FAILURE MAKE YOU SIT OR LIE DOWN TO REST DURING THE DAY?

Panel 2

☐ CARE DECISIONS

ORDERS: COMPRESSION SOCKS, DIURETIC DOSE
PROBLEMS: ANXIETY, DEPRESSION

DO YOU HAVE SWELLING IN YOUR ANKLES OR LEGS?
- ○ NO
- ○ A LITTLE
- ● SOME
- ○ A LOT

DOES YOUR HEART FAILURE MAKE YOU SLEEPING WELL AT NIGHT DIFFICULT?
- ○ NO
- ○ A LITTLE
- ● SOME
- ○ A LOT

Panel 3

☐ CARE DECISIONS

ORDERS: COMPRESSION SOCKS, DIURETIC DOSE
PROBLEMS: ANXIETY, DEPRESSION

○ A LOT

DOES YOUR HEART FAILURE MAKE YOU SLEEPING WELL AT NIGHT DIFFICULT?
- ○ NO
- ○ A LITTLE
- ● SOME
- ○ A LOT

DOES YOUR HEART FAILURE MAKE YOU SLEEPING WELL AT NIGHT DIFFICULT?
- ● NO
- ○ A LITTLE
- ○ SOME
- ○ A LOT

[ NEXT ] [ SAVE PROGRAMS ]
[ LOAD SAVED QUESTION ] [ START OVER ]

Panel 4

☐ CARE DECISIONS

ORDERS: COMPRESSION SOCKS, DIURETIC DOSE
PROBLEMS: ANXIETY, DEPRESSION

DO YOU HAVE SWELLING IN YOUR ANKLES OR LEGS?

SOME

DOES YOUR HEART FAILURE MAKE YOUR SLEEPING WELL AT NIGHT DIFFICULT?

SOME

DOES YOU YOUR HEART FAILURE MAKE YOU SIT OR LIE DOWN TO REST DURING THE DAY?

NO

[ NEXT ]
[ RESET ]

☐ RUN QUERY

QUERY TYPE: [PATIENT LIST ▶]

PATIENT LIST: [PATIENT LIST B ▶]

WHERE:

| CONCEPT | CONCEPT QUALIFIER | VALUE | CODES | | | | | | | |
|---|---|---|---|---|---|---|---|---|---|---|
| DIABETES | HAS DIAGNOSIS | | ICD9250.02 | | | | | | | |
| SYSTOLIC BL... | > | 125 | EVENT CODE: 250784 | | | | | | | |
| | | | | | | | | | | |
| | | | | | | | | | | |
| | | | | | | | | | | |

[ADD] [REMOVE]

[OK]
[CANCEL]

■ DISCERN CARE DECISIONS

| SELECT PERSON | TASK | EDIT | VIEW | PATIENT | CHART | LINKS | NOTIFICATIONS | NAVIGATION | HELP |
MESSAGE CENTE | RUN QUERY | AR TRACKING SHELL ORDERS QUEUE STAFF ASSIGNMENT
NEW STICKY NAM | RUN NATURAL LANGUAGE QUERY | ANGE SUSPEND AUDIO/VISUAL CHARGE ENTRY EXIT CALCULATOR | CARDIOLOGY ▶

⊟ SCOTT JAMES
PROVIDER: DR. SMITH    AGE: 55 YEARS    MRN: 123456789    * ALLERGIES NOT RECORDED *
                       DOB: NOVEMBER 29 1957

◀                                          ▶

⊟ TOC
FLOWSHEET          CHF READMISSION: STAGE 1 RISK 22%
MAR
POWERORDERS        ⌐DEMOGRAPHIC─────────────────────────────┐
TASK LIST          │ COPD                             TRUE  │
I&O                │ DIABETES                         TRUE  │
PROBLEM LIST       │ IDIOPATHIC CARDIOMYOPATHY        TRUE  │
IVIEW              │ INTRAVENTRICULAR CONDITION DELAY TRUE  │
┊CHF READMISSION┊  │ ISCHEMIC HEART DISEASE           TRUE  │
                   └────────────────────────────────────────┘

⊟ CARE DECISIONS
                                                              ◀              ▶
                   ┌──────────────────────────────────────────────────────────┐
                   │ DO YOU HAVE SWELLING IN YOUR ANKLES OR LEGS?             │
                   │   ⦿ NO                                                   │
                   │   ○ A LITTLE                                             │
                   │   ○ SOME                                                 │
                   │   ○ A LOT                                                │
                   │                                                          │
                   │ DOES YOUR HEART FAILURE MAKE YOU SLEEPING WELL           │
                   │ AT NIGHT DIFFICULT?                                      │
                   │   ⦿ NO                                                   │
                   └──────────────────────────────────────────────────────────┘

⊟ COMPONENTS                                          REFRESH    CONFIGURE

┌FINDINGS─────────────────────────────────────────────────────────────────┐
│ FINDING                                              DATE PERFORMED     │
│ DIABETES                                             2013-04-17         │
│ COPD                                                 2013-04-17         │
│ IDIOPATHIC CARDIO                                    2001-04-13         │
└─────────────────────────────────────────────────────────────────────────┘
┌LABS─────────────────────────────────────────────────────────────────────┐
└─────────────────────────────────────────────────────────────────────────┘

DEAU, JONA...
DEAU, JONATHAN    DOB:08/20/1982    DOSE WT:85,000 KG (01/10/2013)    SEX:MALE    MRN:489    ATTENDING: MCGEE, BOYD
ALLERGIES: PENICILLIN    AGE:30 YEARS    MY HEALTH: NO    ISOLATION:    LOC:IMC 1N; 125; 01    FIN#:374

:TOC    ◀ ▸ | ⌂ GROWTH CHART

DISCERN CAREDECISION
MAR
FLOWSHEET DOC
ACTIVITIES AND INTERVENTIONS
NEW TASKS
ORDERS
MEDICATION LIST
NOTES
DIAGNOSIS & PROBLEMS
ALLERGIES
HISTORIES
ACQUIRED DATA
GROWTH CHART
PATIENT INFORMATION
DOCUMENTATION
FORM BROWSER
HEALTH MAINTENANCE
IMMUNIZATION SCHEDULE
MAR SUMMARY
ONCOLOGY
OVERVIEW
PERIOPERATIVE DOC
REFERENCE
RESULTS REVIEW
PRENATAL SUMMARY
AMBULATORY SUMMARY
ICU SUMMARY

ADMIT

PHYSICIAN CONTACT ASSIGN

CONSOLIDATED PROBLEMS
CLASSIFICATION: ALL
ADD NEW AS: THIS VISIT

CONSOLIDATED PROBLEMS

LABS

SUBJECTIVE/HISTORY OF PRESENT ILLNESS

PROCEDURE HISTORY (0)

CARE PROCESS MODELS

CREATE NOTE

PROBLEMS (5)                                   ALL VISITS
  COLON CANCER (153.9) CHRONIC        THIS VISIT
  COPD [CHRONIC OBSTRUCTIVE
  PULMONARY DISEASE] (496)             THIS VISIT
  DIABETES TYPE II NOS (250,000)       THIS VISIT
  GASTROPARESIS (536.3)                THIS VISIT
  AT RISK FOR INJURY

SHOW HISTORICAL (0)

LABS    | SELECTED VISIT | LAST 1 DAYS | LAST 72 HRS | MORE |
        | 6/7/13 | 6/7/13 | 3/9/13 | 1/10/13 |        | 12/9/12 | 9/10/12 |
        | 22:09  | 16:03  | 22:05  | 12:23  | 10:50  | 22:02   | 21:51   |
▲ PRIMARY RESULTS
LDL     |   --   |   --   |  136   |  136   |   --   |   139   |   129   |
TRIG    |   --   |  91.0  |  136   |  89.0  |   --   |   69.0  |   121.0 |

DETERMINING NEW KNOWLEDGE FOR CLINICAL DECISION SUPPORT

CROSS REFERENCE TO RELATED APPLICATIONS

This Application claims the benefit of U.S. Provisional Application No. 61/864,992, titled Clinical Decision Support and Services, filed Aug. 12, 2013, which is hereby expressly incorporated by reference in its entirety.

Also, much of this disclosure is shared with the following U.S. patent applications, filed on even date herewith, (one of which is this application), each of which is hereby expressly incorporated by reference it its entirety:

| Title | application No. | Filing Date |
|---|---|---|
| DYNAMICALLY DETERMINING RISK OF CLINICAL CONDITION | 14/147,978 | Jan. 6, 2014 |
| DECISION SUPPORT WITH CLINICAL NOMENCLATURES | 14/148,050 | Jan. 6, 2014 |
| DYNAMIC QUERYING WITH CLINICAL NOMENCLATURE | 14/147,991 | Jan. 6, 2014 |
| DECISION SUPPORT FROM DISPARATE CLINICAL SOURCES | 14/148,002 | Jan. 6, 2014 |
| ENHANCED NATURAL LANGUAGE PROCESSING | 14/148,020 | Jan. 6, 2014 |
| DYNAMIC FLOW OF CARE FOR DECISION SUPPORT | 14/148,028 | Jan. 6, 2014 |
| DYNAMIC ASSESSMENT FOR DECISION SUPPORT | 14/148,039 | Jan. 6, 2014 |
| DETERMINING NEW KNOWLEDGE FOR CLINICAL DECISION SUPPORT | 14/148,046 | Jan. 6, 2014 |
| USER INTERFACE FOR CLINICAL DECISION SUPPORT | 14/148,059 | Jan. 6, 2014 |

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In brief and at a high level, this disclosure describes, among other things, methods, systems, computer storage media, and graphical user interfaces for facilitating clinical decision support and managing patient population health by health-related entities including caregivers, health care administrators, insurance providers, patients, and other entities. An embodiment of the invention includes a system for providing services for mapping clinical health information across health records systems and data sources; dynamically directing care processes triggered by findings at points in time to support specialists with contextualized decision support information for determining next actions, using information from care plans and pathways, in some cases; discovering and incorporating, into decision support services, new ontologies, and behavior generation, sensory perception, and world modeling to achieve adaptive goals.

An embodiment includes a system for dynamically directing the care process for single and multi-conditions at key points in time to provide decision support using contextually intelligent aware components. For example, relevant labs, findings, medications, and procedures can be presented to a user flexed or tailored to the user, such as a user-specialty, role, venue, clinical condition(s), or other attributes. An embodiment includes one or more software agents or software routines implemented across a distributed cloud-computing platform for facilitating the services. In some embodiments, the agents or routines are autonomous or semi-autonomous, adaptive, and capable of machine-learning. In so doing, embodiments can provide predictive, preventative, screening and monitoring services, in addition to diagnostic and therapeutic services, for patient conditions and events including overlapping concurrent, multi-condition and multi-diagnoses.

Additional examples of decision support services provided by embodiments of the invention are described below in the Detailed Description. Some of these services include providing timely contextual information about patients including condition risks, risk factors and relevant clinical information components that are dynamically updatable; imputing missing patient information including information needed to provide diagnoses, recommendations, or decision support; dynamically generating assessments for obtaining additional patient information based on context, such as caregiver specialty; data-mining and information discovery services including discovering new knowledge, such as new clinical variables associated with clinical conditions or events; identifying or evaluating treatments or sequences of patient care actions and behaviors, and providing recommendations based on this information; intelligent, adaptive decision support services including identifying critical junctures in patient care processes, such as points in time that warrant close attention by caregivers; near-real time querying across diverse health records data sources, which may use diverse clinical nomenclatures and ontologies; improved natural language processing services; and other decision support services.

BRIEF DESCRIPTION OF THE DRAWINGS

Embodiments are described in detail below with reference to the attached drawing figures, wherein:

FIGS. 1A-1E depict aspects of an exemplary operating environment suitable to implement embodiments of the present invention;

FIG. 3B illustratively depicts a block diagrams of an exemplary system for facilitating clinical decision support in accordance with embodiments of the present invention;

FIGS. 5A-5F illustratively depict screen displays showing example graphical user interfaces for facilitating clinical decision support for patient(s) by caregiver(s) in accordance with embodiments of the present invention;

FIGS. 6A-6G illustratively depict example screen displays showing aspects user interfaces for performing a query in accordance with embodiments of the present invention;

FIG. 8A-8D depicts illustrative screen displays of an example user interface for presenting and receiving clinical patient information in accordance with embodiments of the present invention.

DETAILED DESCRIPTION

Figure 1A:
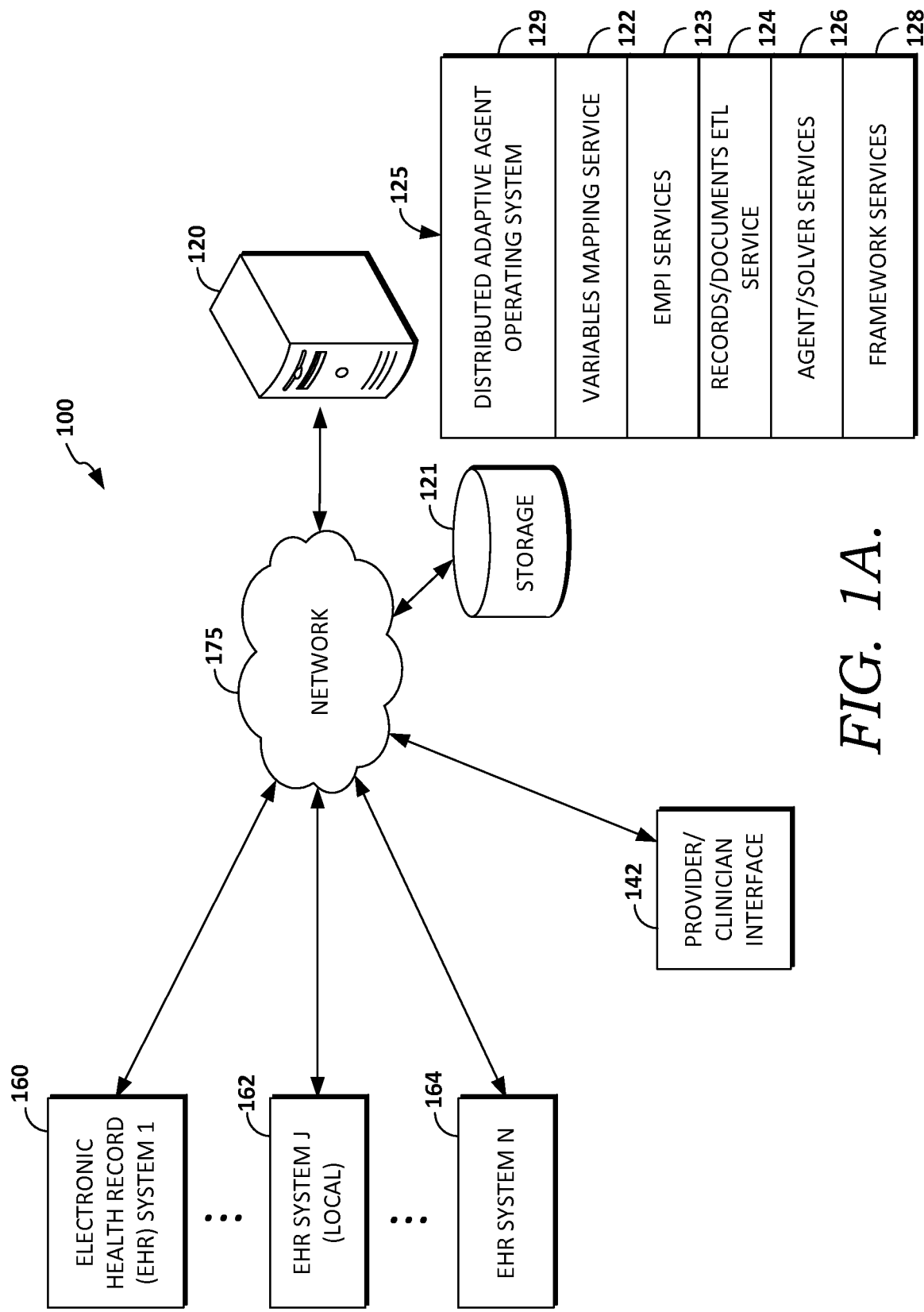

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other storage devices. These technologies can store data momentarily, temporarily, or permanently.

Throughout this description, several terms are used to aid the understanding of certain concepts pertaining to the associated system and services. These terms intended to help provide an easy methodology of communicating the ideas expressed herein and are not necessarily meant to limit the scope of embodiments our technology. The following is a list of these terms:

| Term | |
|---|---|
| Clinical concept | Discretized health-related information capable of being encoded. A clinical concept may include clinical variables, clinical values, clinical information elements or combinations thereof. For example, a clinical variable having a clinical value may be encoded as a single code representing the clinical variable and clinical value. |
| Clinical variable/ attribute | A category or type of clinical information about a patient such as BP, Respiratory Rate, weight, blood glucose, sex, age, condition(s), diagnoses, or other types of clinical information. |
| Clinical value | Patient-specific value associated with a clinical variable, such as 132 lbs. for weight, 32 years for age, male for sex, 120 SBP, demographic values, diagnosis (such as yes or no; acute, moderate, or other value) |
| Clinical information element or component | A piece or component of health-related information for a patient, such as a lab result, finding, test, study, or other element of clinical information. |
| Clinical condition | A disease, diagnosis, medical issue, or medical event for a patient, wherein an event may include an epoch or series of epochs. |
| Condition risk score | A likelihood or probability that a patient has or will develop a clinical condition. In some instances a degree of the patient's condition (e.g., mild, severe, or acute) is also considered. |
| Condition risk factors | A set clinical variables and associated values for a patient that are determined to be relevant to a condition, including a decision support event, and used for determining a patient's likelihood for having or developing the condition. In some embodiments and scenarios, condition risk factors can include other conditions. |
| Condition program | A program, such as a course, algorithm, rule(s), routine, guideline, plan, or goal for determining a patient's likelihood of having or developing a condition. |
| Contextual ontology | A set of clinical concepts associated with a particular context, such as a condition, which may be codified and interpretable by humans and machines. |

Regarding the use of singular and plural, we do not mean to intend any sort of strict numerical implication by using the singular or plural of a term; similar to our lack of intent to imply the singular by using "a" or "the." Trying to capture the plural in words or in the FIGs. would often lead to wordiness. For example, though we might refer to "a database," clearly we fully anticipate that such reference would be equally applicable to multiple databases. By way of another example "a memory" does not imply one single memory device.

In brief and at a high level, this disclosure describes, among other things, methods, systems, computer storage media, and graphical user interfaces for providing decision support services. By way of a high level example, systems and methods are provided for dynamically directing the care processes for single and multi-conditions at key points in time to provide guidance using contextually intelligent aware components. For example, relevant labs, findings, medications, and procedures are presented to me flexed to my specialty, role, venue, condition, and other attributes powered by inference engines, solvers, algorithms, rules or plans, and facilitated via healthcare agents continually learning. In some embodiments, the systems and methods operate with multiple platforms, such as Cerner's PowerChart®, MPages®, Touch apps, and our Population Health, and non-Cerner solutions. In an example embodiment software agents collaborate together to support a practice-driven workflow. Using rules-driven decision modules and through machine learning algorithms, the agents come up with conclusions that enable caregivers to identify, predict, attribute, measure, and act. Drawing data from multiple sources like HIE, EMR, Claims, and PBM databases, the agents can create or arrange a longitudinal person or patient record.

For example, in one embodiment and still at a high level, a supervised learning algorithm simplifies the process of standardizing proprietary codes so that all clinical attributes are coded to appropriate standards. Person or patient records from different systems are then matched using a record-linking formula that uses both clinical and demographic attributes. These efforts result in a complete and shareable person record. Using this longitudinal record alongside a contextual discern ontology framework and mathematical models, the agents produce the appropriate outcomes, such as condition risk scores. The contextual ontology, which is like a language for a particular risk, that both humans and machines can interpret, is developed using a supervised mathematical knowledge discovery engine. It enables the module to present information based on the caregiver's role, venue, and patient condition. Like a human learning from past experience, solvers and routines pore over a decade of de-identified health facts data to provide the healthcare agents with the knowledge needed to produce helpful conclusions. Accordingly, like a highly skilled assistant, embodiments of the systems and methods present the caregiver with information at just the right time, along with data that is relevant to the current context. And if something is missing that would help complete the picture, some embodiments of the systems and methods even highlights that for the caregiver.

Continuing the example, upon opening a patient chart, the chart application connects with embodiments of the decision support services, which may operate in the cloud, to see if there are any new risks for a clinical condition (including a decision support event) to manage for a particular patient or sets of patients. In some embodiments, a dynamic menu or table of contents (TOC) indicates the risk for one or more clinical conditions, and in some embodiments, a newly identified risk is highlighted or colored. In some embodiments, a caregiver may be notified of a newly identified risk by alarm, email or text message, icon, or other technique. Upon selecting a risk of one or more conditions from the TOC, the user-caregiver is provided supporting details, including a condition risk score and risk factors that contributed to the score and other relevant clinical information elements. In some embodiments, this score can be calibrated based on the caregiver's own health system's historical activity and can be categorized into high, medium, or low risk level. In some embodiments, in addition to this score and related factors that contributed to the risk score, the user interface of the decision-support application displays the clinical components that are relevant to the risk, role, and venue, using the list of meaningful concepts it built for this risk. In some embodiments, these components and clinical factors within each component are further customizable before the provider role or specific need. In some embodiments, a wide variety of such components, such as labs, findings, meds, vitals, and orders may be incorporated into the user-interface decision support application and provide end users with the capability of customizing or building build their own risk models.

In some embodiments, the decision support patient chart includes functionality for flexing or altering the information that is displayed (including what information is presented and the order, ranking, or priority that the information is presented) based on the caregiver specialty, condition(s), venue, or other attributes. For example, when a user opens another patient's chart, the application again uses the user' role (e.g. caregiver specialty) and venue and the person's (or patient's) information in the cloud to see if there are new risks for conditions. In some embodiments a risk score and all the factors that contributed to this score are presented. In some embodiments, where the decision support services determine that additional details might help complete the picture a caregiver needs to provide appropriate care, it provides a helpful questionnaire. In some embodiments, where a question answer already exists in the patient's record, it is pre-populated. In some embodiments, the question and answer pair are associated with an appropriate industry terminology standard, such as standard clinical concepts, which makes it possible for additional decision support-related measurements or events to be triggered. Upon submitting the answers, an embodiment of the system sends notifications to appropriate clinicians and associated roles so they can continue care. In so doing, nothing gets lost in handoff, and each caregiver is presented a view that is tailored or flexed to their role.

An exemplary operating environment suitable for use in implementing embodiments of the invention is described below.

Turning now to FIG. 1A there is presented an example operating environment 100 suitable for practicing embodiments of the invention. Example operating environment 100 includes a computerized system for compiling and/or running an embodiment of a method for providing decision support in accordance with embodiments of the present invention. With reference to FIG. 1A, one or more electronic health record (EHR) systems, such as EHR system 1 160, EHR system J 162, or EHR system N 164 are communicatively coupled to network 175, which is communicatively coupled to computer system 120. In some embodiments, components of operating environment 100 that are shown as distinct components may be embodied as part of or within other components of environment 100. For example, the one or more EHR systems 160-164 may be implemented in computer system 120. Similarly, a single EHR system may perform functions for two or more of the example EHR systems shown in FIG. 1A.

In embodiments, network 175 includes the Internet, and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component shown communicatively coupled to network 175 and network 175. In such embodiments, the firewall may reside on a second component located between the first component and network 175, such as on a server (not shown), or reside on another component within network 175, or may reside on or as part of the first component.

Embodiments of electronic health record (EHR) systems 160, 162, or 164 include one or more data stores of health records, which may be stored on storage 121, and may further include one or more computers or servers that facilitate the storing and retrieval of the health records. In some embodiments, one or more EHR systems 160, 162, and 164 may be implemented as a cloud-based platform or may be distributed across multiple physical locations. Example embodiments of EHRs 160, 162, or 164 include hospital, ambulatory, clinic, health exchange, and health plan records systems. EHR systems 160, 162, and 164 may further include record systems, which store real-time or near real-time patient (or user) information, such as wearable, bedside, or in-home patient monitors, for example. It is further contemplated that embodiments of EHRs 160, 162, or 164 may use distinct clinical ontologies, nomenclatures, vocabularies, or encoding schemes for clinical information, or clinical terms. For example, EHR 160 may be affiliated with a first hospital system that uses a first nomenclature, while EHR 162 may be affiliated with a second hospital system that uses a second nomenclature. Similarly, EHR system J 162, which may be a local (with respect to the caregiver, patient, or clinician) health record, may use a first clinical nomenclature while EHR system N 164, which may be a remotely located (with respect to the caregiver, patient, or clinician) EHR may use a second nomenclature. Further, in some embodiments EHRs 160, 162, and 164 are affiliated with two or more separate health care entities that use two or more distinct nomenclatures. Although FIG. 1A depicts multiple example EHR systems, it is contemplated that some embodiments may employ only one EHR system, or alternatively, may rely on provider clinician interface 142 for storing or retrieving patient record information.

Example operating environment 100 further includes provider clinician interface 142 communicatively coupled through network 175 to the one or more EHRs 160, 162, and 164. Although environment 100 depicts a communicative coupling through network 175 between interface 142 and the one or more EHRs 160, 162, and 164, it is contemplated that some embodiments of interface 142 may be directly communicatively coupled to the EHRs. Embodiments of interface 142 may take the form of a user interface operated by a software application or set of applications on a client computing device such as a personal computer, laptop, smartphone, mobile computer, or tablet computing device. In one embodiment, the application includes the PowerChart® software, manufactured by Cerner Corporation. In an embodiment, the application is a Web-based application or applet.

Provider clinician interface 142 facilitates accessing and receiving information about a specific patient or set of patients, receiving information such as patient information, selections, queries, commands, or actions, and displaying results, recommendations or orders, for example. In some embodiments interface 142 also facilitates receiving orders for the patient from the clinician/user, based on the results. In some embodiments, interface 142 comprises a graphical user interface for facilitating clinical decision support such as illustratively depicted in FIGS. 5A-5F, and 6A-6E. Additionally, interface 142 may use used for providing diagnostic or update services, such as evaluating or modifying condition programs, prediction models associated with condition programs, libraries, content tables used for agents discussed in connection to FIG. 1C, for facilitating human confirmation or computer-derived determinations such as actions, recommendations, diagnoses, linkages, or other such services.

Embodiments of provider/clinician interface 142 may take the form of a user interface and application, which may be embodied as a software application operating on one or more mobile computing devices, tablets, smart-phones, front-end terminals in communication with one or more servers, back-end computing systems, laptops or other computing devices. In some embodiments, provider/clinician interface 142 includes a Web-based application or set of applications that is usable to manage user services provided by embodiments of the invention. In an embodiment interface 142 includes Cerner's PowerChart application. Additional details of some embodiments of interface 142 are described in connection to user interface 2140 of FIG. 1C and FIGS. 5A-5F, and 6A-6E.

Example operating environment 100 further includes computer system 120, which may take the form of a server, and which is communicatively coupled through network 175 to EHR systems 160, 162, and 164, storage 121, and provider/clinician interface 142.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120. Some embodiments of software stack 125 include a distributed adaptive agent operating system 129, which may be implemented as a platform in the cloud, and which is capable of hosting a number of services such as 122, 123, 124, 126, and 128 and decision support manager services. Embodiments of services 122, 123, 124, 126, and 128 run as a local or distributed stack in the cloud, on one or more personal computers or servers such as system 120, and/or a computing device running interface 142. In one embodiment, interface 142 operates in conjunction with software stack 125. Embodiments of services 122, 123, 124, 126, and 128 may be embodied as as one or more software agents, programs, applications, or routines, and in some embodiments are implemented using a BDI model, such as described below.

In embodiments, variables mapping service 122 and records/documents ETL service 124 provide services that facilitate retrieving frequent item sets, extracting database records, and cleaning the values of variables in records. For example, variables indexing service 122 may perform functions for synonymic discovery, indexing or mapping variables in records, or mapping disparate health systems' ontologies, such as determining that a particular medication frequency of a first record system is the same as another record system. In some embodiments, these services may invoke or be invoked by EMPI services 123 or agent/solvers services 126, or other software services. EMPI services 123 include services related to patient record linkage or master patient indexing services, such as described in connection to EMPI component 3250 of FIG. 3B.

Agent/solver services 126 include services that perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org). Agent/solver services 126 are associated with framework services 128, which in an embodiment includes Apache Hadoop and in an embodiments Hbase framework and/or Apache Spark, or in another embodiment similar frameworks, including so called "BigData platforms" which are operable for providing a distributed file system, and which in some embodiments facilitate provide access to cloud-based services such as those provided by Cerner Healthe Intent®.

Example operating environment 100 also includes storage (or data store) 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rule-bases; agent libraries, solvers and solver libraries, such as for agent/solvers services 126, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data stores associated with the one or more EHR systems, such as 161, 162, and 164 and interface 142. Further, although depicted as a single storage data store, data store 121 may comprise one or more data stores, or may be in the cloud.

Figure 1B:
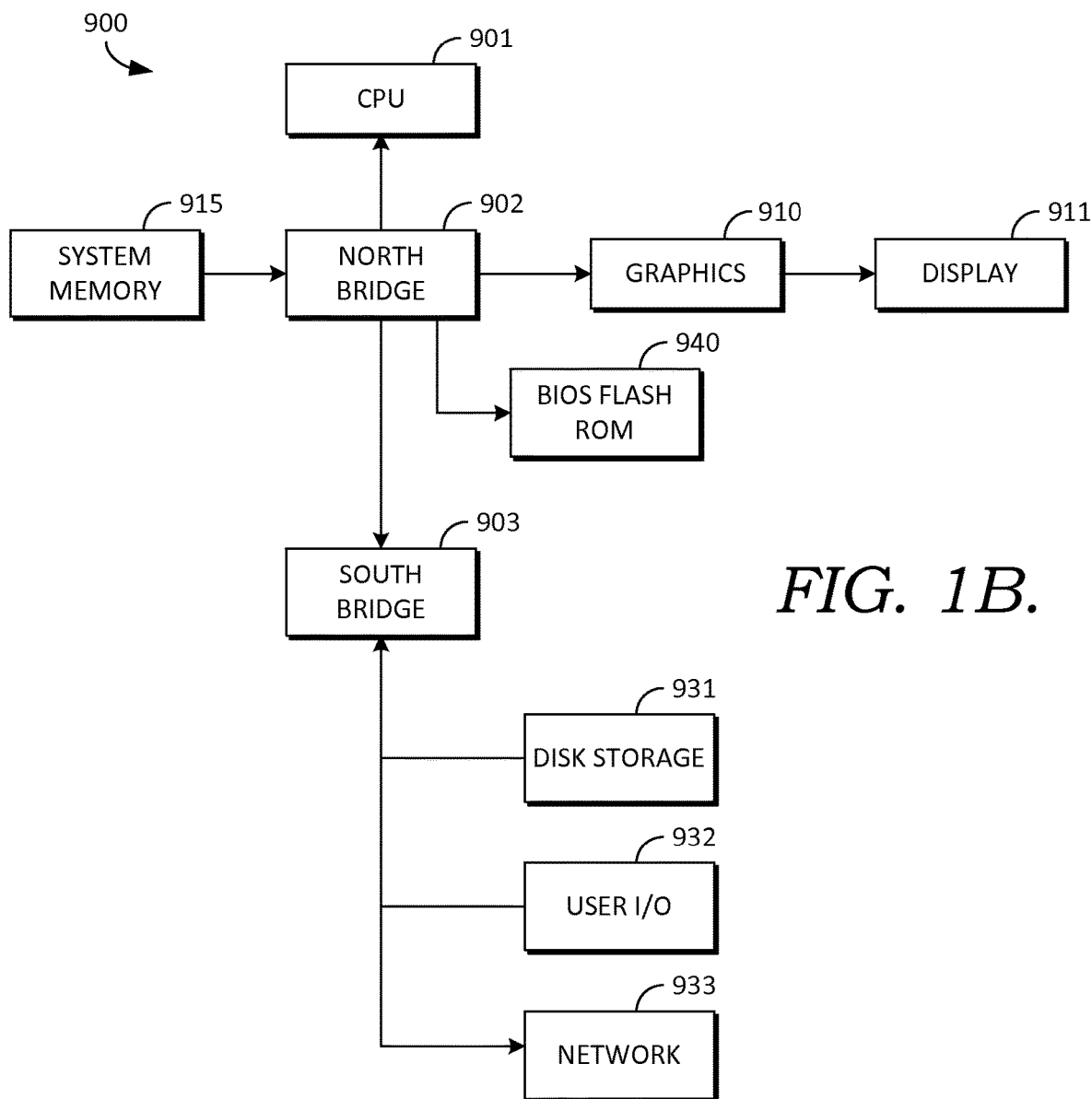

Turning briefly to FIG. 1B, there is shown one example embodiment of computing system 900 that has software instructions for storage of data and programs in computer-readable media. Computing system 900 is representative of a system architecture that is suitable for computer systems such as computer system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 1C:
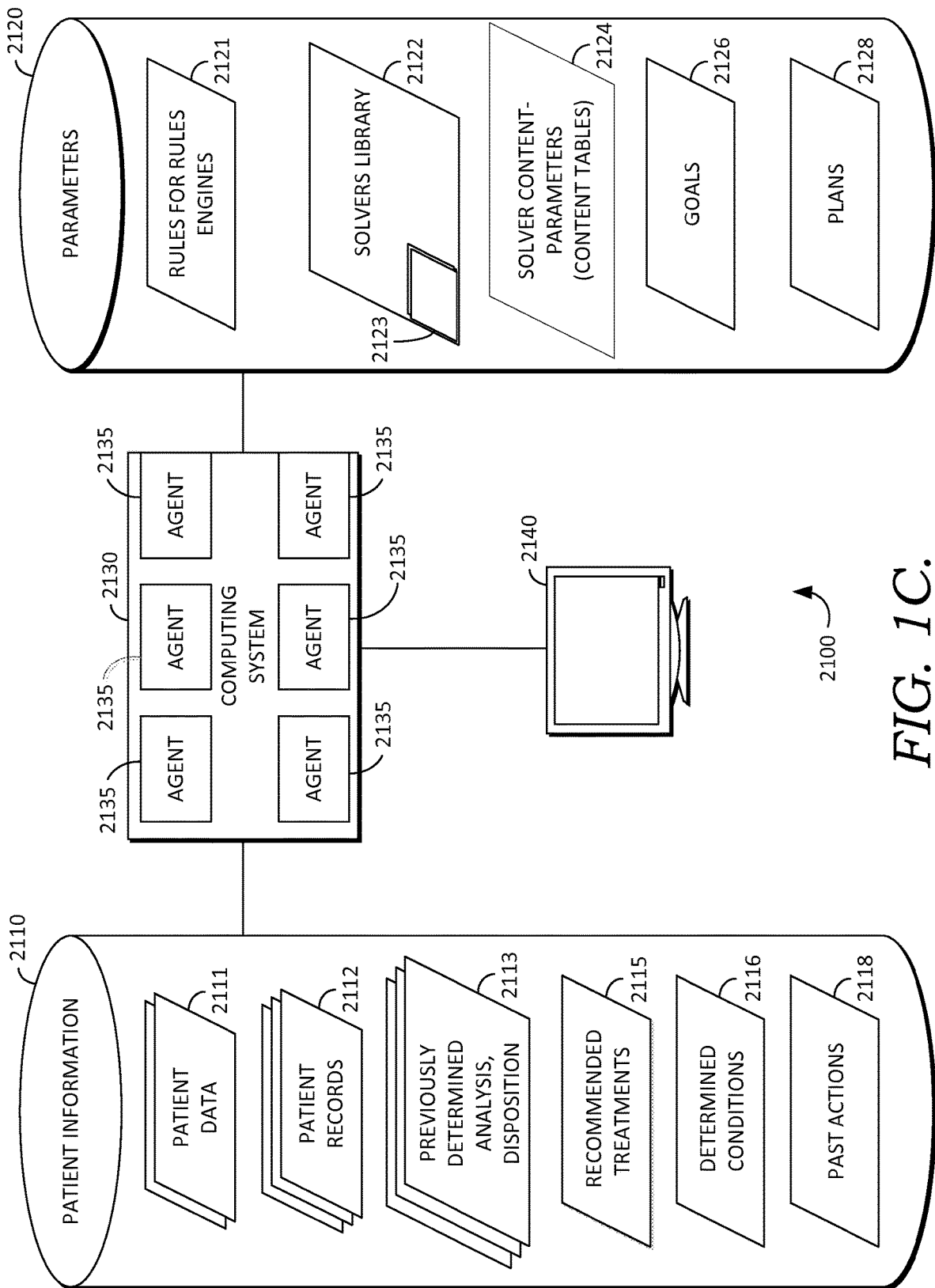

In some embodiments, computer system 120 is a multi-agent computer system with one or more software agents. Turning now to FIG. 1C, in some embodiments, computer system 120, storage 121, and software stack 125 are implemented in operating environment 2100 using a multi-agent computer system such as exemplary computing system 2130 with one or more agents 2135, as shown in FIG. 1C and described in greater detail below. But it will be appreciated that computing system 2130 may also take the form of a single agent system or a non-agent system, as described in other embodiments herein. In some embodiments, computer system 120 is embodied as computing system 2130, and in some embodiments, stack 125 operates on an embodiment of computing system 2130. Computing system 2130 may be embodied as a distributed computing system, a centralized computing system, a single computer such as a desktop or laptop computer or a networked computing system, described in other embodiments herein.

In some embodiments, computing system 2130 is a multi-agent computer system with agents 2135. Multi-agent computing system 2130 may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents 2135 based on beliefs, capabilities and choices that communicate via declarative messaging and use abstractions to allow for future adaptations and flexibility. An agent 2135 has its own thread of control which promotes the concept of autonomy.

Some embodiments using multi-agent system 2130 are include capabilities to adapt the frequency and messages used for communication between the system 2130 and one or more users through user interface 2140, based on changes to the environment and provide capabilities to filter out noisy data, thereby providing more flexible and adaptable decision-making abilities. In some embodiments, this is accomplished by using leveraging preceptors and effectors. Preceptors or sensors, which in some embodiments may be determined by agents, detect changes in an operating environment and pass this information to the agent system. Effectors, which in some embodiments may be determined agents 2135, respond directly to changes in an operating environment and consider goals and alternatives prior to implementing a change to the environment. Examples of sensors are further discussed in the contexts of FIGS. 7B and 7C. For example FIG. 7B shows epoch A at time t, which is dependent on sensors 1 to N at time t−1.

Embodiments using multi-agent system 2130 further have the capability of supporting intelligent information retrieval and filter out noisy data and utilize heuristics to narrow down a search space to assist in solving complex problems. The multi-agent system 2130 facilitates designing individual agent behaviors and their interactions with other agents 2135 and with users, through user interface 2140. In some embodiments, agents 2135 encoded with both declarative and procedural knowledge and can therefore learn by means of exploration of knowledge and imitation of other agents, for example, by leveraging aggregation of bottom-up and top-down modeling. In some embodiments, the agent system 2130 accepts an abstract workflow and converts it into an actual executable workflow, by for example, using contract and negotiation in multi-agent system 2130. The executable workflow may then leverage agents to run the actual workflow.

Furthermore, embodiments using multi-agent system 2130 coordinate the actions of the agents 2135 to cooperate to achieve common objectives, and negotiate to resolve conflicts, which allows for adaptability, flexibility, and organizational relationships. The transformation of heterogeneous knowledge and content into homogeneous knowledge and content is an important trait of the multi-agent system to provide interoperability. The multi-agent system 2130 operates to achieve its goals while still interacting with agents, including agents outside of the multi-agent system 2130 (not shown) and users at a higher degree of flexibility.

As a practical example, in some embodiments, a multi-agent system 2130 can be utilized to efficiently validate theoretical improvements to processes for detecting certain conditions, such as improvements to processes for determining likelihood of sepsis, described herein. In this example, input may be received, including patient information 2110 (described below) and one or more sets, thresholds, or ranges of variables, from parameters 2120 (described below), such as for example blood pressure, blood oxygen, temperature, or other variables used in the process for detecting sepsis described herein. Such variable sets, threshold(s), or range(s) may be received from one or more health care providers or from an agent, and, in some embodiments, may be specified in one or more content tables 2124 (described below). In some embodiments, the received variable set(s), threshold(s), or ranges may differ based on differing opinions, strategies, or condition-detection theories of the health care providers, or based on differences in the patient information 2110 available to each health care provider.

Continuing the example, in embodiments using multi-agent system 2130, for each of the variable set(s), range(s) or threshold(s), an agent 2135 may be invoked for determining likelihood of a condition, including conditions or other clinical decision support event(s), or for monitoring the patient for likelihood of the condition or event. In some embodiments the agents work in parallel, such that each agent operates with different set, range, or threshold values, thereby resulting in multiple evaluations for the likelihood of the condition or event being carried out. In some embodiments, the results of the evaluations by the agents are compared to determine which set(s), range(s), or threshold(s) performs better for determining likelihood of the condition or event. Further, in some embodiments, multi-agent system 2130 learns the set(s), range(s), threshold(s) or other parameters 2120 and patient information 2110 that are more likely to result in an accurate diagnosis or detection of the condition or event. In some embodiments, the particular set(s), range(s), threshold(s), or other parameters 2120 which yield a more accurate determination of likelihood of the condition or event are weighted, biased, or otherwise noted for future use in evaluating a patient for risk of the condition or event. Similarly, the particular process followed by the agent, for diagnosis or detection of the condition or event, which led to a more accurate result, is also noted. In this way, potential improvements in the condition detection processes (described herein, below) can be determined by experimentally modifying the input variable set(s), range(s), threshold(s), and other parameters 2120. In some embodiments, the agent responsible for implementing an improved detection process can be simply swapped with the agent handing the existing detection process.

In some embodiments, these agent(s) and processes, including learned processes, are embodied as clinical condition programs, or condition programs, which may be used for evaluating patient information to determine a patient's likelihood or risk for having or developing a particular clinical condition or decision support event. Further, in some embodiments, an agent, which may be a dedicated agent, facilitates handling and operation of a condition program including applying it to a set of patient information, evaluating it, and updating it when needed. In some embodiments, agents may dynamically construct a clinical condition program for a particular patient, based on the state of the patient. (For example, briefly referencing the patient condition state machine shown in FIG. 7A, a patient at a particular location or state of the state machine, which may correspond to multiple concurrent, overlapping conditions, may have a specific condition program generated for determining conditions risk scores, risk factors, and clinical information relevant to the condition(s).)

In some embodiments, agents 2135 continually monitor events to proactively detect problems and leverage reasoning to react and dynamically alter a plan. Practical reasoning involves managing conflict resolution where the relevant considerations are provided by the agent's desires about what the agent believes. This involves deliberation by deciding what state of affairs the agent wants to achieve using intentions and by means-end reasoning which is how to achieve those desires using plans. By way of background, an intention is stronger than a desire and planning achieves designated goals. Thus in one embodiment, a basic planning module consists of goals and intentions to be achieved, actions that can be performed, and a representation of the environment. These plans can thus handle priorities, uncertainty and rewards to influence the actual plans. An agent has its own thread of control which promotes the concept of autonomy. Additional information about the capabilities and functionality of agents and distributed multi-agent operating systems, as they relate to our invention, is provided in U.S. patent application Ser. No. 13/250,072, filed on Sep. 30, 2011, which is herein incorporated by reference in its entirety.

Continuing with FIG. 1C, system 2130 is communicatively coupled to patient information 2110 and parameters 2120 data stores, which may be embodied as storage 121, and user interface 2140. Patient information 2110 and parameters 2120 data stores are illustratively depicted in FIG. 1C as comprising two data stores for conceptual purposes, but it is contemplated that patient information 2110 and parameters 2120 may be stored across multiple records systems, including different EHR systems and in different networks or locations or may be on a single data store, as described below.

System 2130 performs processing on patient information 2110 and parameters 2120. In some embodiments, including the practical example described above, system 2130 includes one or more agents 2135, which process patient information 2110 using parameters 2120 to determine goals, plans, patient actions, orders, patient conditions and recommended treatments, or invoke other agents, such as agent solvers, to perform these determinations. In a further example, system 2130 may receive patient data 2111 in the form of a natural language narrative, such as a physician's note, and invoke a data-extraction agent, from solvers library 2122, to extract discretized data from the note. In some embodiments, an agent or routine of system 2130 may determine clinical concept code(s) associated with the discretized data and store these codes in the patient's health record. System 2130 may then use the discretized data, or coded concepts, and content tables 2124 to instantiate and apply another solver agent, such as a type of healthcare agent, from solvers library 2122 to determine a patient's condition and recommended treatments. In some embodiments, a similar process is applied by system 2130 to other unstructured clinical data sources, such as studies and literature, patient provided information, raw patient data from monitors or sensors, population studies and demographic information or other data sources. In so doing, unstructured clinical data from a variety of sources can be mapped into a standard or preferred clinical concept nomenclature. Additional details relating to agent-driven data mapping processes are provided in the embodiments discussed in connection to FIG. 3A.

Upon determining a patient's condition and recommended treatments, system 2130 might invoke an expert rules engine(s) using rules 2121, which may be embodied as other agents, to determine specific actions to take or a disposition for the patient, based on the determined conditions and recommended treatments, in an embodiment.

System 2130 is executed by or resides on one or more processors operable to receive instructions and process them accordingly, in one embodiment, and may be embodied as a single computing device, such as computing device 120 of FIG. 1A, or multiple computing devices communicatively coupled to each other. In one embodiment, processing actions performed by system 2130 are distributed among multiple locations such as a local client and one or more remote servers or in one embodiment computing devices or EHRs associated with different health entities. In one embodiment, system 2130 resides on a computer, such as a desktop computer, laptop, tablet, or mobile or smart phone computer. Other example embodiments of system 2130 reside on a desktop computer, a cloud computer or distributed computing architecture, a portable computing device such as a laptop, tablet, ultra-mobile P.C., a mobile phone, wearable computer, or a combination of such devices.

Example environment 2100 shows multi-agent system 2130 communicatively coupled to user interface 2140. In an embodiment, user interface 2140 comprises provider/clinician interface 142 of FIG. 1A. In some embodiments, user interface 2140 includes functionality for providing a presentation capability and user interface to facilitate communication with users. For example, a user may view determined results about a patient or provide additional information such as patient information, in one embodiment. User interface 2140 may be a single device or a combination of devices and may be stationary or mobile. In some embodiments, a user interface on display device takes the forms of one or more presentation components such as a monitor, computing screen, projection device, or other hardware for displaying output. In some embodiments, a user interface 2140 takes the form of one or more presentation components with user input components, such as a remote computer, a desktop computer, laptop, PDA, mobile phone, ultra-mobile PC, computerized physician's clipboard, or similar device. In some embodiments, data elements and other information may be received from user interface 2140. Queries may be performed by users through user interface 2140; additional orders, tests, feedback or other information may be provided through the display device to user through user interface 2140.

As described above, Environment 2100 includes data store 2110 which includes patient information and data store 2120 which includes parameters. In some embodiments, data stores 2110 and 2120 comprise networked storage or distributed storage including storage on servers located in the cloud and may me embodied as storage 121 of FIG. 1A. Thus, it is contemplated that for some embodiments, the information stored in data stores 2110 or 2120 is not stored in the same physical location. For example, in one embodiment, one part of data store 2110 includes one or more USB thumb drives or similar portable data storage media. In one embodiment, data stores 2110 and 2120 are distributed at multiple locations including locations of a plurality of medical organizations 206, 208, and 210 or FIG. 2. Additionally, information stored in data stores 2110 and 2120 can be searched, queried or analyzed using system 2130 or user interface 2140, which is further described in connection to FIGS. 6A-6D.

As shown in environment 2100, data store 2110 comprises information specific to a patient, which in some instances includes incomplete, outdated, uncertain, overlapping, and conflicting information. In an embodiment, data store 2100 may represents a patient health record, which may be embodied as a longitudinal person record. Moreover, the information might come from a variety of sources and/or exist in a variety of formats including for example, narratives and discretized data. Examples of sources can include patient data from different data sources (Data source 1-N) of FIG. 3A, such as different medical entities, traditional hospitals, walk-in clinics, urgent care facilities, other locations that render medical services, as well as in-home patient monitors and patient-wearable sensors or monitors. In one embodiment, patient information includes one or more of patient data 2111, patient records 2112, previously determined analysis or disposition 2113, which are associated with the patient, recommended treatments 2115, previously determined patient conditions 2116, and past actions 2118 performed for the patient. In some embodiments, patient data 2111 can include lab results, real time or near real time information such as data provided by a physician, including information based on observation or a patient's explanation, information provided by a sensor (for example, blood pressure or heart rate), or other patient data. In some embodiments, patient records 2112 can include electronic medical records ("EMR"), health information exchange ("HIE"), personal health record ("PHR"), patient claims, and other health records associated with a patient.

In some embodiments, the component pieces of patient information included in patient information 2110 may be logically stored together in a complete patient record, or may be logically connected by reference pointers or addresses to one or more different patient records. In an embodiment component portions of a health record that are determined to be probably matches to a particular patient are provisionally linked to the patient record. In an embodiment, the provisional linkage may be confirmed by auditing. In an embodiment, patient information 2110 is encoded into clinical concepts using a standard or preferred nomenclature, and may associated with a master patient index (MPI).

Continuing with patient information 2110, previously determined analysis and dispositions 2113 include information relating to previous analyses performed on a patient and previous dispositions determined for the patient, including previous analyses and dispositions determined by way of the multi-agent system, in some embodiments. Multiple-agent system 2130 may handle a complex problem, such as determining patient conditions or recommended treatments. Each of the agents 2135 may generate multiple analyses and/or disposition for the patient. For example, as described above, agents operating in parallel and using different input parameters 2120, and in some instances different patient information 2110, may determine a patient's likelihood of having a condition(s) or other decision support event(s). In some embodiments, a degree of statistical certainty about a determined disposition of analysis may be arrived at by correlating or otherwise comparing each of the separate analyses and/or dispositions. More specifically, if separate agents 2135 each determine substantially the same analysis or disposition using different levels of patient information from a single patient or from a multiple patients having similar clinical information relevant to the determination, then there may be a higher degree of confidence that the analysis or disposition is accurate, given the available patient information. In some embodiments, if the analysis or disposition of the separate agents ends up being a false positive for detection of a condition, then those agents can be designated or otherwise associated as having less effective determination capabilities. Similarly, where agents are more effective (i.e., more accurate and/or more efficient, such as agents able to perform in less time or with less input information) at detecting a patient's condition, then those agents can be designated or otherwise associated as having more effective capabilities. In some embodiments, the most effective agent may be swapped into (or invoked for) the condition detection process. For example, in determining a patient's likelihood of having a particular condition, the most effective agent may be invoked. In some embodiments, it is conceivable that performance or effective capability of an agent may be dependent on the specific patient information 2110. For example, in circumstances where a set A of patient information 2110 is available, agent A-prime may have the best performance, but where patient information 2110 is different, such as if a set B of information is available, then agent A-prime is less effective. But another agent, such as agent B-prime, may be more effective. Therefore, an association can be established of which agent is more effective, based on the specific patient information 2110 that is available for a given patient. In one embodiment, another agent handles this association and invokes the most capable agent based on the available patient information 2110. In another embodiment, this association is encoded as a logic rule or rules engine. In this way, system 2130 learns and also adapts to be more effective, based on the circumstances (such as the available patient information 2110). In some embodiments, feedback information is provided to a user or health care provider as to which agent or which patient information 2110 and/or parameters 2120 provide the most accurate determination. In some embodiments, the feedback is provided to a supervisor agent, which manages other agents. This feedback information facilitates the streamlining of care for future patients and facilitates determining effective treatment care plans or actions. For example, if the feedback information indicates that a high probability of detection of a condition or event, can be determined based on variables V1 and V2 alone, where the range of variable V1 should be RX-RY for a certain patient type and within a specified time window, and the threshold of variable V2 should be T1, and that variables V3-V5 are unnecessary, then accordingly, only patient information regarding variables V1 and V2 are needed. In an embodiment, variables V1 and V2 may be determined as risk factors for the condition, and may be specified in a condition program associated with the condition. Thus, for a given future patient, a health care provider only needs to specify tests or otherwise provide information for variables V1 and V2. The health care provider might be able to forego expensive testing for determining variables V3-V5.

In some embodiments, a health care provider might suggest a set of ranges or thresholds for variables (as parameters 2120) or a range or threshold that is different from what is typically used. After agents using the different ranges of thresholds complete analyses, such as determining likelihood of a particular condition, system 2130 can provide information to the health care provider, via user interface 2140, for example, as to whether the suggested ranges or thresholds were more effective or less effective at diagnosing the patient's condition.

Recommended treatments 2115 include currently and previously recommended treatments for a patient. In one embodiment, this information includes time-related or near realtime data associated with the time that the recommended treatment was determined, as well as an indication of whether the recommended treatment has been acted upon. In one embodiment, recommended treatments 2115 also specify how the recommended treatment was determined, including for example, available patient information, the type of solver that was applied, and the resulting patient conditions, thereby enabling a health care provider to query the recommended treatments to see how a particular treatment was determined or to generate a report.

Past actions 2118 include previous actions determined by the multi-agent system 2130. Similarly to what is described above in connection to recommended treatments 2115, past actions 2118 may include time information associated with the time that the action was determined or executed, or may also specify how the action was determined or executed.

Data store 2120 comprises parameters and information associated with the multi-agent system 2130. Although depicted as working with a multi-agent system, in one embodiment, data store 2120 works with single-agent system parameters and information, or non-agent system parameters and information. In one embodiment, data store 2120 includes rules for a rules engine 2121, and solvers library 2122. Rules for a rules engine 2121 include a set of rules or library of rules. In one embodiment, rules 2121 are usable by an expert rules engine, such as an agent 2135 in multi-agent system 2130. Alternatively, in a non-agent embodiment, rules 2121 include a library of rules usable by non-agent processes. One example application of rules 2121 by an example rules engine or agent includes determining actions or dispositions associated with a patient from a number of determined conditions or recommended treatments. Another example includes the mapping clinical concept codes across multiple clinical nomenclatures and identifying contextual ontologies by determining sets of frequently associated clinical concept codes.

Solvers library 2122 includes one or more solvers, which can include non-agent solvers, agent solvers (discussed below) or both. In some embodiments, solvers, which may also be referred to as "resolvers," are applied to determine one or more conditions or recommended treatments for a patient. A finite state machine solver may be used to determine the conditions and recommended treatments of a patient suffering from a number of conditions including congestive heart failure. Solvers, including solver agents, may also invoke or apply other solvers or agents. Continuing this example, the finite state machine agent solver may invoke a linear solver, such as a mixed integer linear solver, to evaluate each state in order to determine the patient's condition risk score in a scenario where the patient has multiple conditions. In one embodiment, the finite state machine returns the actual state for each clinical condition of the patient, which is then passed on to the mixed integer linear solver as parameters, to apply the mixed integer solver based on the clinical state, and content tables 2124. The solvers library 2122 can be updated as new solvers are available. Another example solver is the data-extraction solver, which is described in further detail below. A data-extraction solver is a type of solver that is applied to unprocessed patient information, such as a physician's narrative or patient results data, in order to generate discretized data that is usable for other solvers. Another example solver is for imputing values for missing or delayed clinical values for a particular patient, wherein the imputed values are based on values of patients with similar clinical conditions or similar clinical variables, such as determined by a frequent/relevant itemset mining solver. Yet another example solver is a patient clinical events trajectories mining solver, for identifying patterns or sequences of clinical events for patient, which may be compared to the patterns or sequences of other patients to find similar patients. Additional details about sequence and/or trajectory mining solvers are described in U.S. Provisional Application 61/798,123, filed Mar. 15, 2013, which is herein incorporated by reference in its entirety.

Additional solvers are provided in FIG. 1E, by way of example only and not limitation. With reference to FIG. 1E, a number of example runtime or near solvers are shown on the right-hand side of the table shown in FIG. 1E. (Although the term "runtime" is used, it is contemplated that the solvers shown may be used in realtime (or near realtime) patient-treatment scenarios or used offline or non-realtime scenarios.) Additional details regarding Tanimoto distance matching are discussed in connection to FIGS. 7B and 7C, and further discussed in U.S. Provisional Patent Application, 61/886,457 filed Oct. 3, 2013, which is herein incorporated by reference in its entirety. Additional details regarding the chronbach alpha solver are described in U.S. application Ser. No. 13/269,279, filed Oct. 7, 2011, which is herein incorporated by reference in its entirety.

Turning back to FIG. 1C, in some embodiments, agents 2135 facilitate solving problems including the problems described above by employing one or more solvers from solvers library 2122 and/or using rules 2121. Furthermore, where existing rule systems may utilize forward chaining, backward chaining and combination, agents 2135 can integrate these rule capabilities as well as other traditional and heuristic techniques. These agents 2135, which may be referred to as agent solvers, can also leverage the best techniques for the problem at hand. In some embodiments, these agent solvers comprise health care agents. In some embodiments the agent solvers implement a clinical condition program.

In some embodiments, the agent solvers can register their abilities or responsibilities to the overall system and coordinate and communicate with other agents, users, or the overall system, to solve problems based on their current capabilities. Still further and as described above in the condition-detection examples, new or improved solvers, which may be introduced at future times, are able to be leveraged by swapping out current agents with new agents dynamically and without the need to recompile or reconfigure the system. Thus embodiments using multi-agent system 2130 can provide advantages, in some scenarios, over single-agent systems and non-agent systems. By analogy, a single celled organism is analogous to a single-agent system, while a complex multi-celled organism is analogous to the multi-agent system. Accordingly, the "reasoning" capabilities of multi-agent system 2130 are superior to the "reasoning" exhibited by a single-agent system, and the multi-agent system 2130 is not constrained at design time and has the ability to grow and adapt over time based on future needs not anticipated at the time of instantiation or design.

In some embodiments, agents 2135 provide enhanced decision support by using multi-agent properties like collaboration, persistence, mobility and distributed operation, autonomy, adaptability, knowledge and intelligence, reactive and proactive capability, reuse, scalability, reliability, maintainability, security, fault-tolerance, trust, and other primary properties. In addition, numerous secondary properties of multi-agents in embodiments of our invention may facilitate decision support, including: reasoning, planning and learning capabilities; decentralization; conflict resolution; distributed problem solving; divide-and-conquer strategies for handling complex problems; location transparency; allowing for competing objects to be represented; goal-driven or data-driven including agent-to-agent or user-to-agent; time-driven; support for multiple layers of abstraction above services thereby providing flexibility, adaptability, and reuse and simplification; negotiation; hierarchies having dynamic self-organization; abilities to spawn and destroy agents as needed; utilization of transient and persistent data; abilities to address uncertain, missing or inconsistent data; sensitivity to resource and time constraints; ontology-driven functionality; flexible run time invocation and planning; obligations; ability to act to achieve objectives on behalf of individuals and organizations; organizational influence; and other secondary properties. Examples of agents, which may be used by the multi-agent systems of embodiments of our technologies, include: Interface agents; planning agents; information agents; adapter wrapper agents; filter agents; discovery agents; task agents; blackboard agents; learning agents, including supervised learning, unsupervised learning, reinforcement learning, for example; observer agents; inference agents; communication agents; directory agents; administrator and security agents; facilitator agents; mediator agents; and agent solvers. Agent solvers can include, for example: Markov decision processing; approximate linear programming; natural language extraction solvers (e.g., nCode, NLP, or MLP solvers); fuzzy-neural networks, logistic and linear regression; forward-chaining inference (e.g., data-driven); backward-chaining inference (e.g., goal-driven); inductive inference; genetic algorithm; neural network including with genetic algorithm for training; stochastic; self-organizing Kohenen map; Q-learning; quasi-Newton; gradient; decision trees; lower/higher bound search; constrain satisfaction; Naives Bayes fuzzy; LP-solver including mixed integer multi-variable min/max solvers; Finite State Machine and HFSM; temporal difference reasoning; data mining for classification, clustering, learning and prediction; K-means; support vector machines; K-nearest neighbor classification; Tanimoto distance; C5.0; a priori; EM, simulated annealing, Tabu search, multi-criteria decision making, evolutionary algorithm, and other such solvers known by one skilled in the art.

In some embodiments, where particular types of agent solvers are more efficient at handling certain patient scenarios, a planning agent may invoke the particular type of agent solver most appropriate for the scenario. For example, a finite state machine agent solver and a linear solver agent solver may be invoked by a planning agent, in a scenario involving a patient experiencing congestive heart failure. Similarly, a planning agent might invoke one or more agent solvers for determining likelihood of sepsis, based on patient information 2110 available and/or the effective capability of the agent solver(s). In some embodiments, agent solvers invoke other agent solvers as necessary.

Continuing with FIG. 1C, some embodiments of multi-agent system 2130 employ decision making for applications including, for example, searching, logical inference, pattern matching and decomposition. A subset of solvers library 2122 includes decision-processing solvers 2123. Decision processing solvers 2123 are a special set of solvers used for decision making, although it is contemplated that in some embodiments any solvers of solvers library 2122 or solver agent maybe used for decision processing. Examples of agent decision procession applications include: searching, including heuristic and traditional searching; list; constraint satisfaction; heuristic informed; hill climbing; decision tree; simulated annealing; graph search; A* search; genetic algorithm; evolutionary algorithm; Tabu search; logical inference; fuzzy logic; forward and backward-chaining rules; multi-criteria decision making; procedural; inductive inference; pattern recognition; neural fuzzy network; speech recognition; natural language processing; decomposition; divide-and-conquer; goal tree and subgoal tree; state machine; function decomposition; pattern decomposition; and other decision-processing applications. In some embodiments, agents designed or instantiated with a particular decision-processing application may be swapped out, in a more seamless and transparent manner than with non-agent systems, with another agent having more advanced decision processing functionality as this becomes available or is needed.

Solver content-parameters 2124, which is also referred to as "content tables" 2124, include parameters used for instantiating and applying the solvers. Content tables 2124 provide parameters that specify information regarding conditions, drugs, contra-indications, treatments, orders or other actions, and other parameters used in conjunction with patient information to determine conditions and recommended treatments. In some embodiments, content tables 2124 include information for instantiating condition program agents including instantiating agents to construct a specific condition program for a given patient.

In one embodiment, content parameters 2124 are formatted as independent tables, which might take the form of a matrix, which can be maintained, updated, or swapped out with other tables, by health care providers, physicians, or experts independent of patients. For example, a content table may specify parameters relating to diabetes including what factors in patient information indicate that the patient is in hypoglycemia, what factors in patient information indicate that the patient is in hyperglycemia, contra-indications, treatments such as drugs and drug dosages that should be administered, or additional testing that should be ordered. In another example, content tables specify the set(s), range(s), and/or threshold(s) of variables for detecting likelihood of a condition, such as sepsis. In some embodiments, rows of a content table correspond to different sets, ranges, or thresholds of variables such that a first agent can perform its analysis using content specified in a first row A, and a second agent working in parallel (or the first agent at a later time) can perform its analysis using content from a row B. Further, in some embodiments, the results of analyses can be entered into the rows or associated with the rows. Thus, where multiple agents are running analyses in parallel, with each agent using a different set of parameters specified in one row, the results of the row that correspond to the most effective analysis may be provided to the health care provider or otherwise published to the outside world as the result of the determination for whether the patient has the condition, even though in fact there may be multiple separate results from the different analyses, in some embodiments. This is because in many instances, the health care provider only desires to know whether the patient has a particular condition, and doesn't care about a bunch of different agent-generated results coming from diverse parameters 2120, some of which are more accurate and some of which are better than others.

In some embodiments, content tables 2124 and patient information 2110 provide the information necessary for a solver to determine patient conditions and recommended treatments. Content tables may be updated independently, as new information, treatments, or drugs become available.

Goals 2126 include objectives which guide the system, such as embodiments of a multi-agent, single-agent, or non-agent system 2130, in the selection of a plan and, ultimately, the determination of what actions to take place as a result of incoming patient data. Therefore in some embodiments, goals are based on incoming patient information. For example, a goal may specify "determine if patient has diabetes," "manage conditions for sepsis," "manage conditions for CHF while keeping other patient conditions stable," or "minimize the cost of patient treatment." In some embodiments, goals are used to motivate agents 2135. Specifically, agents 2135 operate under guidance of a goal that is consistent with patient information when deciding what actions to take, plans to select and execute, or which solvers to invoke. Thus, any plan selected and executed will be consistent with the determined goals 2126, which are based on patient information 2110. Moreover, as patient information 2110 changes, such as when newer or additional patient information 2110 becomes available or a patient's condition changes during the course of treatment, goals 2126 may be changed or replaced. In some embodiments such as multi-agent systems operating under the belief-desire-intention ("BDI") model, a goal is analogous to a desire. Accordingly, in one embodiment, agents 2135 may act to fulfill a desire that is based from a set of agent beliefs or facts determined from available patient information 2110. In some embodiments, goals 2126 can be organized in one or more sets, groups, tables, databases, or libraries with, in some embodiments, subgroups related to similar goal-objectives; for example, a subgroup of goals may relate to handling patient treatment costs or treating cancer.

Plans 2128 include, in some embodiments, specific executable algorithms, instructions, schedules, or the similar plans for carrying out a specific objective that is consistent with a determined goal 2126. For example in some embodiments, a clinical condition program may be implemented as a plan. In some embodiments, plans 2128 may specify intention or an intended outcome to be achieved that is consistent with a determined goal 2126. Plans 1228 can include sets or libraries of plans, which in some embodiments are associated with certain goals 2126. For example, for the goal of "manage conditions for sepsis while keeping other patient conditions stable," plans associated with this goal may specify actions for determining a patient's condition by examining patient information including blood pressure and blood oxygen. The plan may further specify recommended treatments, orders, or other plans to be executed. In some embodiments, plans 2128 also include planning agents, which can assist in the selection and execution of a plan. For example, a planning agent may select a plan, which in some embodiments may also be an agent, for treating sepsis based on patient information that indicates sepsis; the plan may specify using solvers such as logistical regression on the patient information to determine the patient's condition and recommended treatment, in one embodiment.

In another example, a specific condition program plan under the condition-detection goal, may specify using a data-extraction agent for extracting discrete data items from a physician's note written in natural language, and then instantiating one or more solver agents, which carry out the processes for determining likelihood of the condition or of risk factors that may be present, which are used to determine the likelihood of the condition. In one embodiment rather than specifying a specific solver or set of solvers to use (e.g., data-extraction and finite state machine solvers), a plan may specify an intention, (e.g., determine patient's condition when patient information indicates sepsis), and invoke an agent 2135 to select the best solver applicable based on the available patient information 2110. Under the BDI model, a plan is analogous to an intention; thus a plan is sort of like an intention to process the goal with which the plan is associated. The plan 2128 is executed to meet the goal 2126, or partially meet the goal. In one embodiment, a planning engine is used for determining plans 2128 consistent with goals 2126. The planning engine, which could be an agent, non-agent rules engine, a decision tree, or other decision process, selects a plan.

Figure 1D:
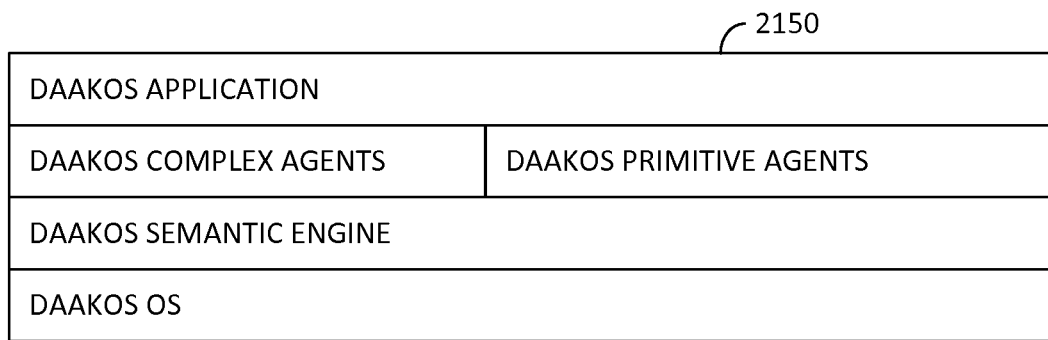

Turning to FIG. 1D, an illustrative example is provided of a framework suitable for implementing a multi-agent system, such as computing system 2130 of FIG. 1C, and is referenced generally by the number 2150. In some embodiments, framework 2150 is suitable for supporting stack 125 of FIG. 1A. In some embodiments, stack 125 is built on framework 2150, and in some embodiments stack 125's services operate as software services on framework 2150. Furthermore, in some embodiments using multi-agent computing system 2130, these services are carried out using one or more agents.

As shown in FIG. 1D, example framework 2150 has a layered architecture. At the lowest level depicted in the example embodiment shown in FIG. 1D, framework 2150 includes the Distributed Adaptive Agent Knowledge Operating System ("DAAKOS"). In an embodiment, DAAKOS includes a decision-support framework. In an embodiment, DAAKOS is a multi-agent framework with heuristic, adaptive, self-optimizing and learning capabilities and the ability to decompose complex problems into manageable tasks to assist clinical decision making at point of care. For example, caregivers and other users can leverage this intelligent agent system to detect a change in personal health or to leverage up to date knowledge about medical conditions, preventive care, and other relevant interests. Accordingly, in one embodiment, DAAKOS can be thought of as an intelligent, self-learning agent system using a cloud metaphor.

Specifically, DAAKOS utilizes multi-agents 2135 that collaborate with each other and interface with external systems, services and users and has the ability to monitor changes and incorporate past knowledge into decision making in order to generate and evaluate alternative plans or adapt plans to handle conflict resolution and critical constraints. A multi-agent virtual operating system provides efficient means to build complex systems composed of autonomous agents with the ability to be reactive, persistent, autonomous, adaptable, mobile, goal-oriented, context aware, cooperative and able to communicate with other agents and non-agents. In some embodiments, intelligence is achieved within agents by way of support provided by a rich ontology within a semantic network. For example, a multi-level of collaborating agents 2135 allows low-level agents to transform data so that it can be passed on to another agent, and to continue the data transformation until the data has been completely transformed from bits of data which may sometimes represent incomplete, outdated, or uncertain data, to form a usable collection of data with rich meaning. In this example, when it becomes necessary to attack complex problems, the agent 2135 is permitted to constrain and narrow its focus at an individual level to support decomposition. Domain specific agents can be leveraged in some embodiments to use an ontology to manage local domain-specific resources.

The DAAKOS operating system layer handles process management, scheduling, memory, resource management, Input/Output ("I/O"), security, planning, as well as other processes traditionally handled by operating systems, and in some embodiments includes memory, which may include short, intermediate, and/or long-term memory, I/O, internal agent blackboard, context switching, kernel, swapper, device resource management, system services, pager, process managers, and logging, auditing, and debugging processes. In some embodiments, the DAAKOS operating system layer is a distributed virtual operating system.

In an embodiment, The DAAKOS layer is built upon a multi-agent framework layer such as JADE. In other embodiments, frameworks such as Cougaar, Zeus, FIPA-OS, or an open-agent architecture, or other suitable architecture may be used. In an embodiment, such as the example embodiment depicted in FIG. 1D, DAAKOS includes a multi-agent framework.

In some embodiments, the multi-agent framework includes the following properties: FIPA compliance; support for autonomous and proactive agents and loosely coupled agents; peer-to-peer communication; fully distributed architecture; efficient transportation of asynchronous messages; support for white and yellow page directory services; agent life-cycle management; agent mobility; subscription mechanism for agents; graphical tools for debugging and maintenance; support for ontology and content languages; library for interaction protocol; extensible kernel for extensions to build customized framework; in-process interface for launching and control; support for running agents on wireless mobile devices; integration with various Web-based technologies; and pure Java implementation.

JADE, which is an acronym for Java Agent DEvelopment framework is a middleware software development framework that is used for facilitating implementation of multi-agent systems. Specifically, the JADE platform includes functionality which facilitates the coordination of multiple agents, and functionality for facilitating the distribution of agent platforms across multiple machines, including machines running different operating systems. Moreover, JADE further includes functionality for changing system configuration at run time by moving agents from one machine to another, as required.

On top of the DAAKOS operating system layer, in the embodiment illustratively provided in FIG. 1D, is the DAAKOS Semantic Engine, which provides the platform for DAAKOS agents 2135. DAAKOS agents 2135 include complex agents and primitive agents. On top of the agents' layers are DAAKOS Applications. These include, for example, DAAKOS agent solvers such as a finite state machine instantiated and executed to determine a patient's conditions and recommended treatments, transactions knowledge engines, and other applications leveraging DAAKOS agents 2135.

Figure 2A:
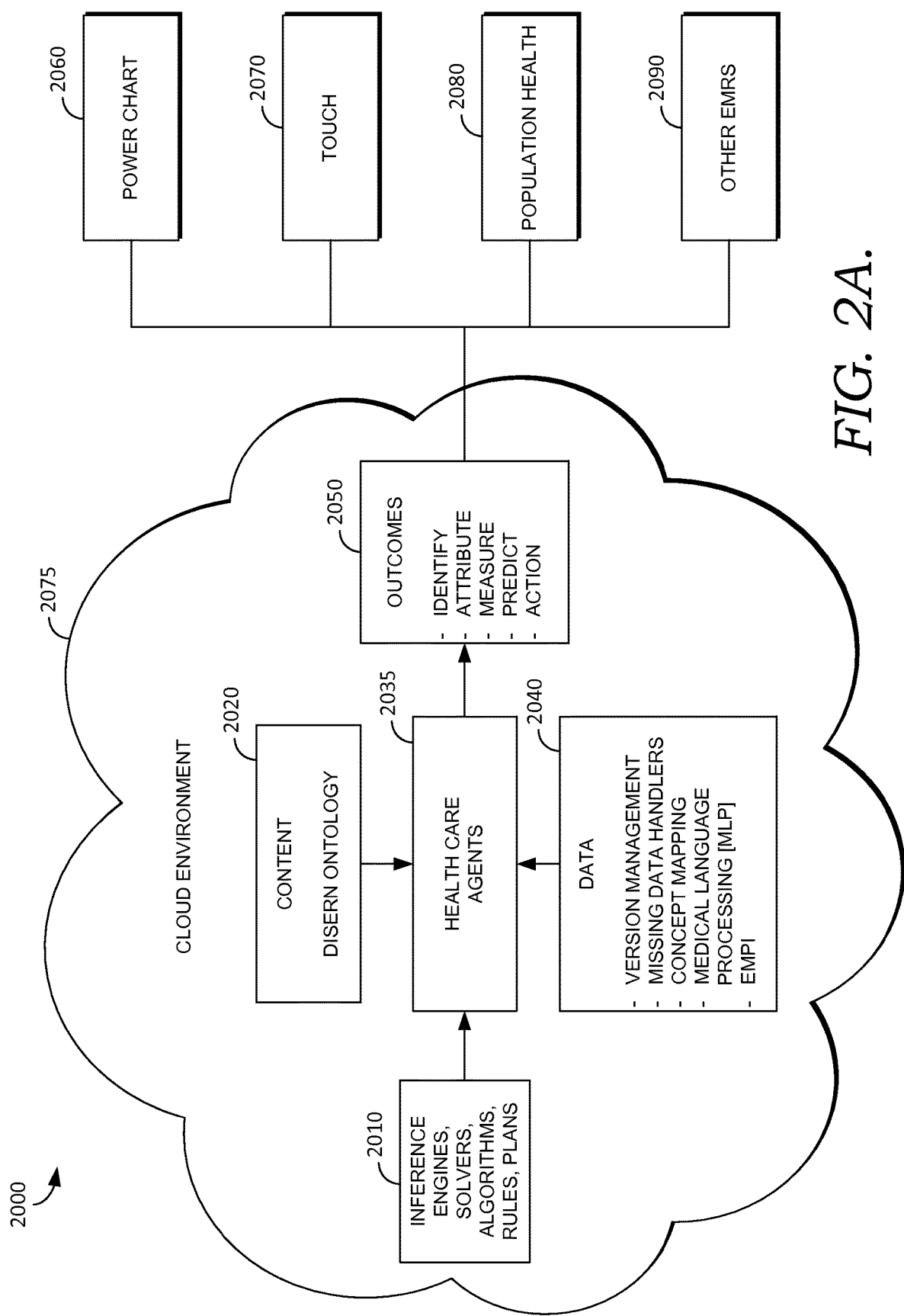
FIGS. 2A-2D depict block diagrams of an exemplary systems for facilitating clinical decision support in accordance with embodiments of the present invention.

Turning now to FIG. 2A, a block diagram of an exemplary system for facilitating clinical decision support is provided and referred to generally as system 2000. Decision support system 2000 supports multiple platforms such as Power-Chart 2060, MPages (not shown), Touch 2070, Population Health 2080, and other EMRs 2090, for example. In some embodiments, system 2000 comprises many agents, including healthcare agents 2035 and other agents (not shown) collaborating together to enable a practice-driven workflow.

For example, in some embodiments, using inference engine(s), solver agent(s), algorithm(s), rule(s), or plan(s) 2010 ("solver agent(s) 2010") which include traditional rules-driven decision components and machine learning algorithms or agents, the healthcare agents 2035 determine outcomes 2050 to facilitate decision support such as enabling a caregiver to identify, predict, attribute, measure, or act. The outcomes may be presented to care providers at appropriate points in time along with data that is relevant to the current context, as described further below. Drawing data 2040 from multiple sources, such as HIE, EMR, Claims, and PBM databases, the agents arrange a longitudinal person record, as further described in connection to FIGS. 3A and 3B.

Figure 2B:
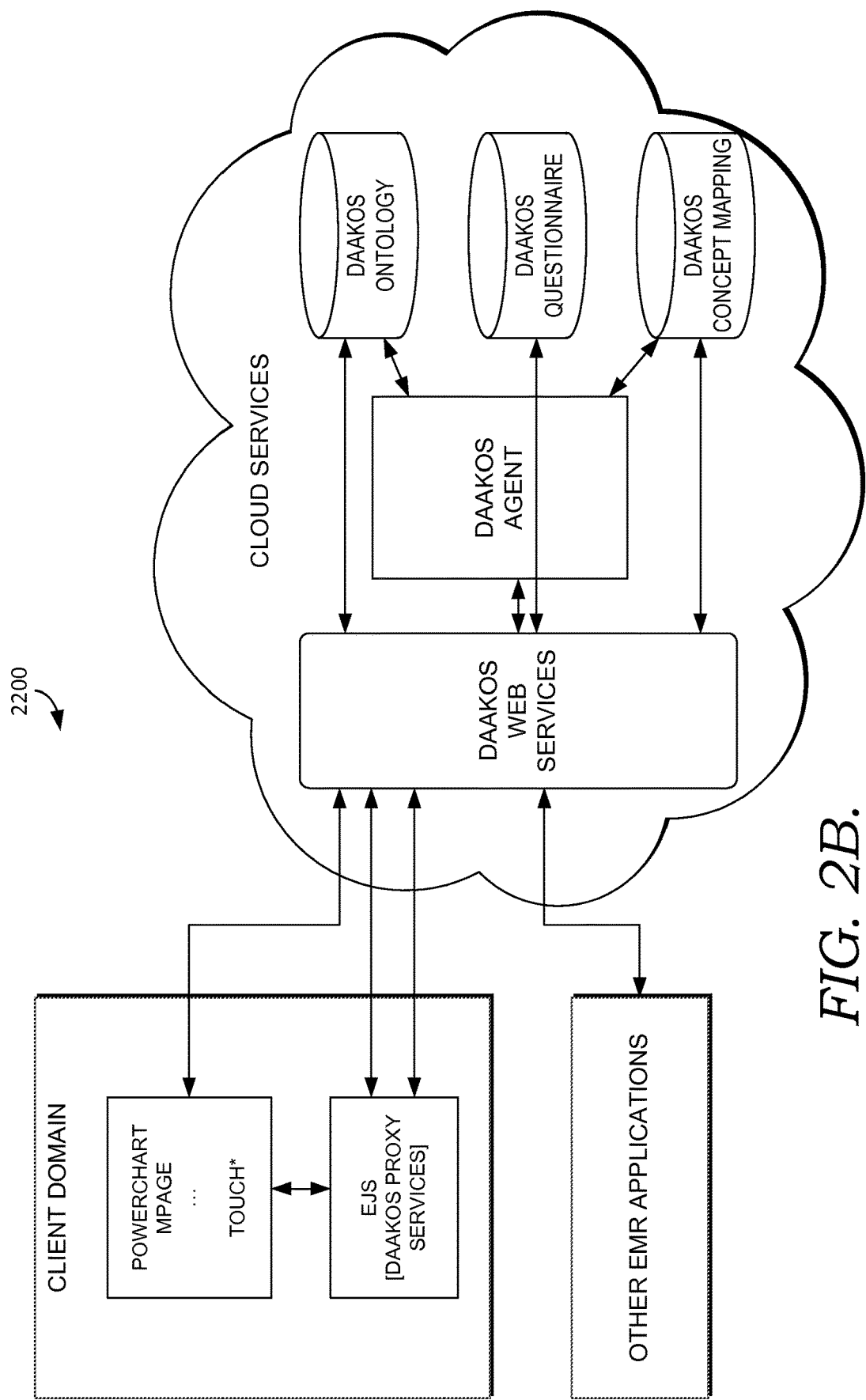

With reference to FIG. 2B, a block diagram of another aspect of an exemplary system for facilitating clinical decision support is provided and referred to generally as system 2200. The system of FIG. 2B shows cloud services including web services and DAAKOS agents (health care agents), which interact with ontology, questionnaire, and concept mapping data stores. The interaction with the questionnaire (or dynamic assessment) is further described in connection to FIG. 5E. Agent interaction with ontology and concept mapping is further described in connection to FIGS. 3A, 2D, and 3B. Web services also accesses questionnaire data store for generating patient assessments, as shown in FIG. 5E. On the client side, EMR applications (such as third party applications, patient health chart applications, including PowerChart® and Cerner's MPages™ platform, and proxy services access the cloud services.

Figure 2C:
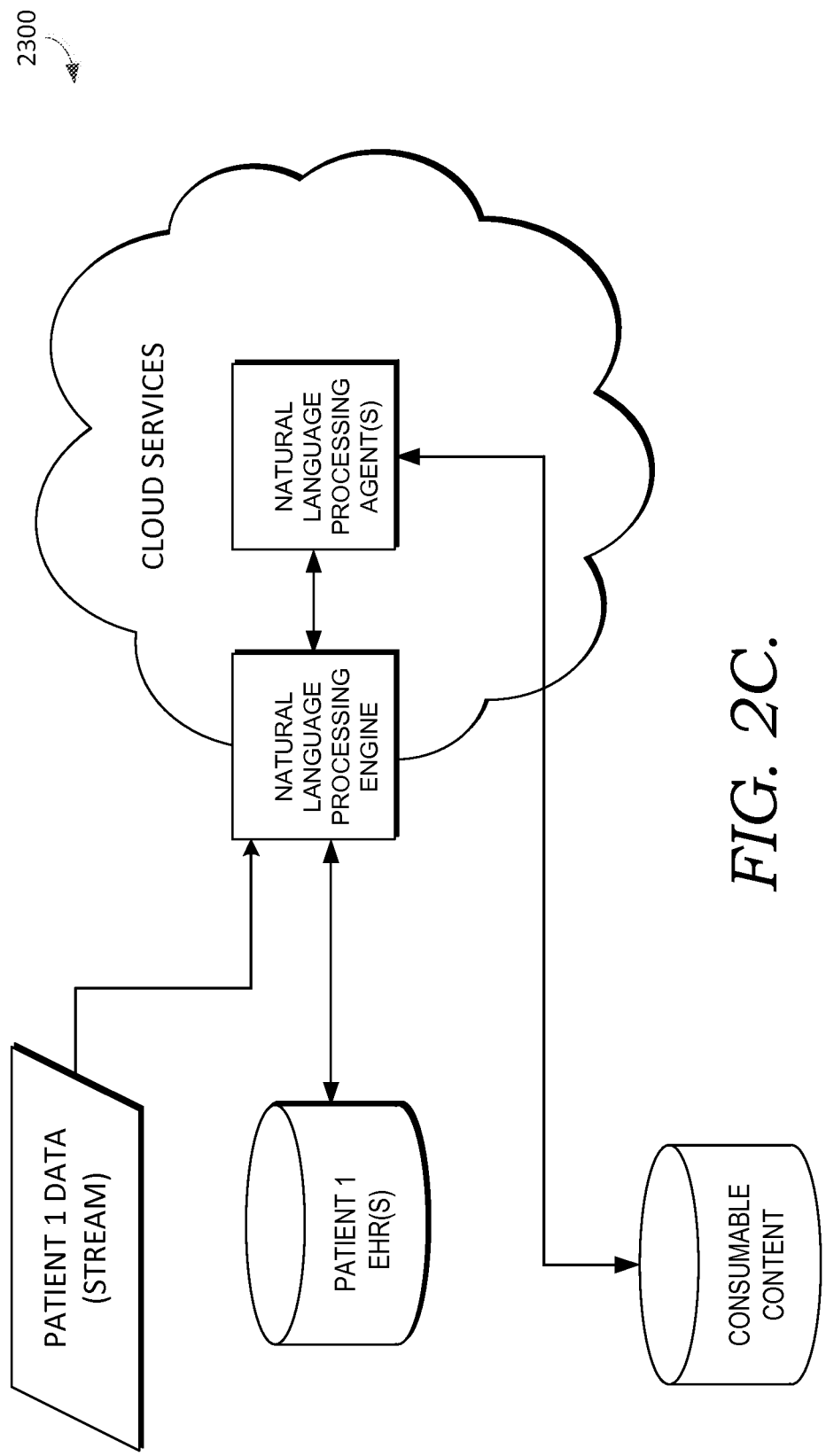

With reference to FIG. 2C, a block diagram of an aspect of an exemplary system for processing and mapping patient data into consumable content is provided and referred to generally as system 2300. In this example, a natural language processing engine received patient information (such as from one or more patient EHRs or a data stream, which may be provided by a patient sensor or provided each time a patient is assessed by a caregiver. Natural language processing engine may use one or more natural language processing agents to process the received patient information into consumable content, which may be used by decision services discussed in connection to FIGS. 4A through 4K. In some embodiments, the consumable content is de_identified. In some embodiments, the patient information is encoded into one or more clinical concepts, which may be translated or "mapped" to a standard or universal nomenclature, as described in connection to FIG. 3A, thereby rendering the content consumable by the other decision support services, applications, features, and agents described herein.

Figure 2D:
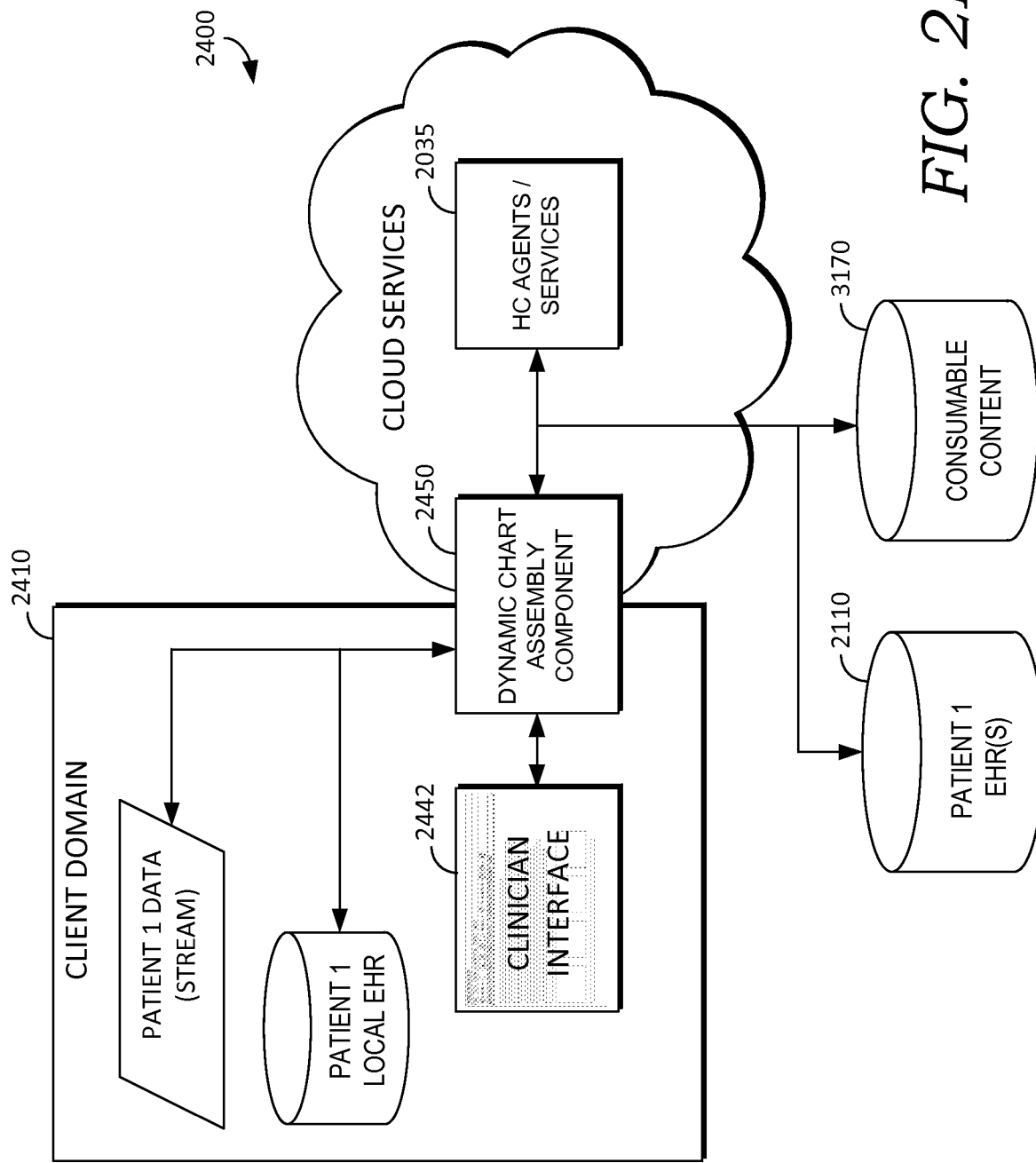

With reference to FIG. 2D, a block diagram of another aspect of an exemplary system for facilitating clinical decision support is provided and referred to generally as system 2400. System 2400 illustrates one example of embodiments for a decision support application and user interface discussed in connection to FIGS. 5A-6D. In particular, in some embodiments, clinical interface 2442 comprises user interface 5142, which by be embodied as provider/clinician interface 142 of FIG. 1A. System 2450 also shows assembly component 2450, which assembles information used by interface 2442. In some embodiments, assembly component 2450 operates as a web server and may assemble information into a markup language format for delivery to a client (not shown) in the client domain 2410 that presents interface 2442, such as via a web browser. In some embodiments, assembly component 2450 facilitates the flexing and contextualization of information presented in interface 2442, and the presentation of assessment(s), as described further in connection to FIG. 5A-5F, by interpreting the outcomes received from health care agents/services 2035 and generating corresponding instructions for interface 2442 to display the appropriate information. In some embodiments, assembly component also facilitates translation between nomenclatures, such as by invoking a concept mapping agent or mapping/translation routine when information is received from the client domain that is in a proprietary clinical nomenclature, before providing the information to agents/services 2035, other cloud services (not shown); or when information being communicated to the client is in a clinical nomenclature that is not used by the client. In some embodiments, assembly component 2450 also facilitates the dynamic features of interface 2442 (or user interface 5142), such as facilitating dynamic updating of at-risk conditions, risk scores, risk factors, or other presented information, as it changes or becomes available. In embodiments, assembly component 2450 may comprise more than one component and may be located on the client domain, in the cloud or both.

Figure 3A:
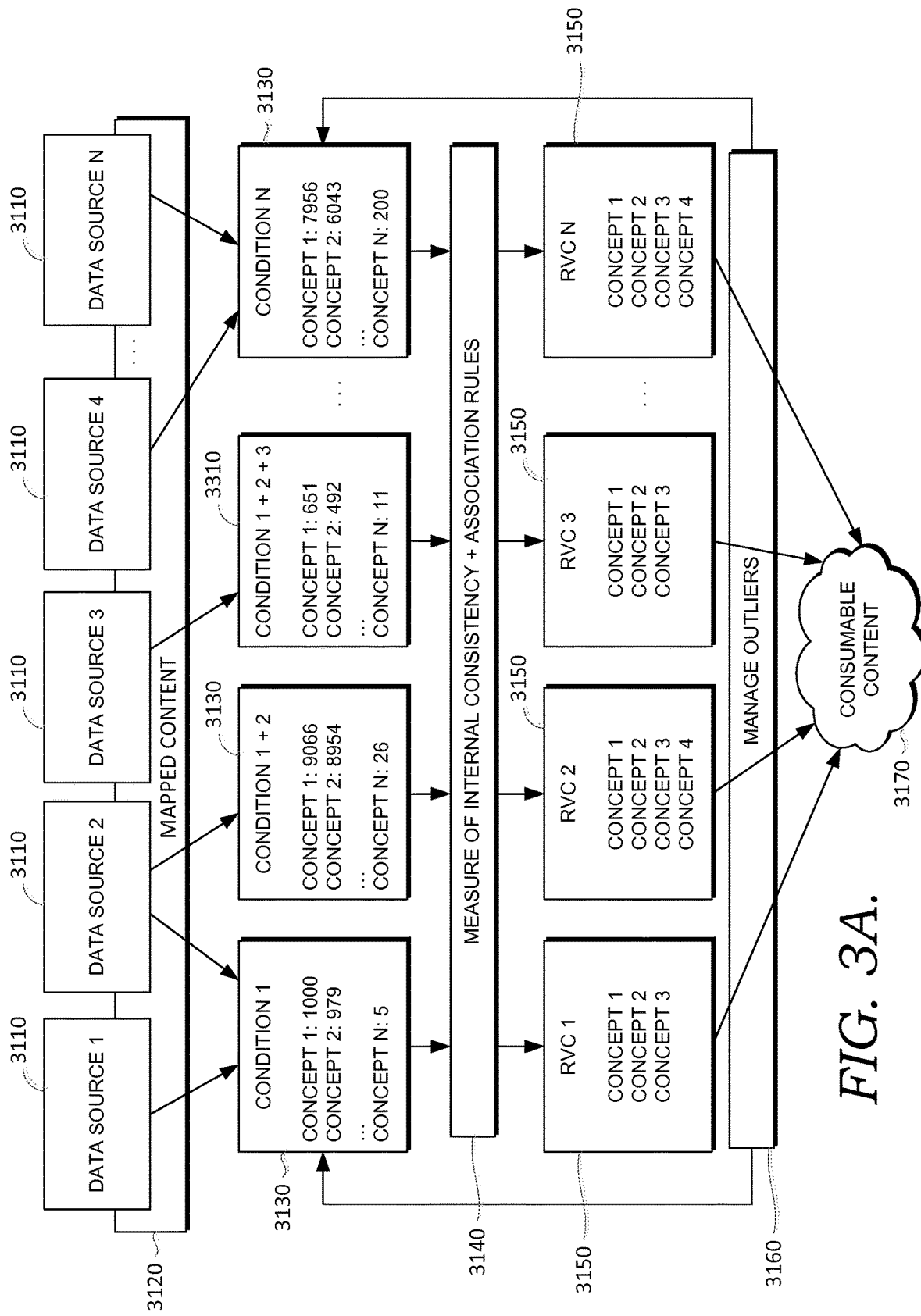
FIG. 3A illustratively depicts a block diagram showing an ontology framework in accordance with embodiments of the present invention.

Turning now to FIG. 3A, a block diagram of an exemplary concept mapping service (or module) 3100 is shown as part of an ontology framework for determining contextual ontologies and consumable content such as mapped population health information; mapped clinical nomenclatures or ontologies; derived knowledge such as newly identified clinical information including newly identified risk factors for a condition(s) or event, newly identified condition associations/patterns or event associations/patterns, effective/ineffective treatments, clinical ontologies; information regarding contextually relevant clinical data for a condition or decision support event; or other health-related information derived from data sources as described herein. In some embodiments, service 3100 is embodied as one or more agents.

By way of background and not limitation, discovery of new knowledge can be determined from data, which may come from various data sources, such as data source 1 through data source N and including diverse data sources of unstructured data. At a high level, embodiments of mapping service 3100 service facilitate discovery of new knowledge first by performing concept mapping on the data to determine structured data, which may be codified with a standard clinical nomenclature. In some embodiments, as described further in connection to FIG. 3B, patient records from different data sources or systems are determined to have a probability of being records for the same patient, based on clinical and demographic attributes. Based on this probability, patient records are matched using a record linkage algorithm or agent thereby generating an inner-operable longitudinal patient record, which may be identified or de-identified depending on the usage context.

Mapping service 3100 receives data from one or more data sources 3110 and determines mapped content 3120. Examples of data sources 3110 include EHRs such as EHRs 160, 162, and 164 of FIG. 1, literature, clinical studies or trials, historical data, government records, arrest records, financial, income, and spending information, demographic information, patient provided data, patient records including labs or test results, claims, HIE, EMR, PMB databases, other clinical records, clinical trials, information from visits to a caregiver or treatment facility, patient behavior-pattern information, caregivers behavior pattern information, questionnaires or forms, or other source of clinical data. This list is not intending to be limiting and includes any source of information which may be used for purpose of providing clinical decision support. In one embodiment a data source may provide data in real-time or near real-time. The data may be structured or unstructured. In an embodiment, unstructured data is processed using natural language processing or other data extraction and formatting processes to create structured information. In an embodiment, this is facilitated by one or more agents. In one embodiment, service 3100 stores the structured data as mapped content 3120. In one embodiment, the mapped content is mapped to a common clinical nomenclature and may be aggregated with mapped data from other data sources.

In one embodiment, concept recognition services, which may be embodied as one or more software services or agents operating on multi-agent system 2130, are utilized for discovering and mapping concept synonymies and other processes to produce mapped content 3120. Additional details about the capabilities and functionality of concept recognition as they relate to embodiments of our invention is provided in U.S. patent application Ser. No. 13/569,781, filed on Aug. 8, 2012, which is herein incorporated by reference in its entirety.

In one embodiment, concept mapping service 3100 enables aggregation of data by a user using clinical terminologies that are well defined and well understood by the health care domain. By way of example, in one embodiment, proprietary codes specific to an EMR or EHR are mapped to an appropriate industry-understood clinical terminology. Unstructured content in the form of text, clinical documents, recordings, sensor data, or other formats is discretized or parsed using a medical language process and codified.

In some embodiments, the aggregated mapped data is de-identified for use in research purposes such as population health databases. In some embodiments, using the aggregated, mapped patient data, which includes inner-operable longitudinal patient records, one or more conditions or concepts are targeted to find related concepts, such as other conditions frequently present when the targeted condition or concept is present in the patient data, as shown in blocks 3130. In some embodiments, additional attributes such as patient demographic information, treatment information such as the caregiver or health entity treating the patient for example, may also be combined with the targeted condition(s) or concept(s) to increase the specificity of the related concepts. For example, the targeted condition and demographic information could include African American males having diabetes under age 60. As another example, patients at least 3 months pregnant with income levels below poverty who are treated at a particular hospital and who are enroleed in a particular medication trial. In some embodiments, the targeted condition is multiple conditions, one or more decision support events, sequence(s) or pattern of events. For example, patients who showed diminished symptoms of a particular condition whose health records include a common set of clinical concepts such as common orders or sequence of orders, common caregiver, common demographic attributes, common co-condition or similar common clinical concepts.

At block 3140, in some embodiments mapping service 3100 performs a measure of internal consistency and association rules. In some embodiments this comprises performing statistical analyses on identified related concepts to determine measure(s) of association between a related concept and targeted condition or concept. In some embodiments, related concepts like insulin and diabetes can be processed at block 3140 using mathematical and machine learning algorithms or agents to find the concepts that are relevant and contextual to the point of care, shown at block 3150.

In some embodiments of service 3100, outliers are managed at 3860. Outliers can include identified related concepts occur below a statistical sample size to be determined statistical association, for example, or other outlying concepts. In some embodiments, managing outliers includes identifying outliers and providing them as input into the processes of service 3100 used to determine concepts or conditions related to a target condition, at block 3130.

At 3170, service 3100 provides consumable content, available to many of the services, systems, applications, and platforms described herein, that may be used at the point of care. In some embodiments, prior to providing content at 3170, the machine processed concepts are curated and/or verified by clinical experts to create consumable content.

In some embodiments, mapping service 3100 may be used to determine a contextual ontology, or language of concepts, about a particular condition, concept, including a risk, that both humans and machines can interpret. The contextual ontology may be developed using a supervised mathematical knowledge discovery engine, which may be embodied as an agent, routine, or set of agents or routines. The discovery engine enables service 3100 to provide consumable content that can be presented based on a caregiver's role, venue, patient condition, or other attributes, as determined in connection to 3140, and as described in connection to FIGS. 5A-5F.

In some embodiments, agent solvers 2010, from FIG. 2A, analyze years of de-identified health facts data to provide the health care agents with the knowledge needed to produce helpful conclusions. In this way, health care agents are capable of providing a caregiver with information at the right time including data that is relevant to the current condition and context. In some embodiments, missing information that would otherwise be helpful, such as clinical information needed to determine a condition risk, is highlighted for the caregiver. In some embodiments, an assessment is dynamically generated and provided to the appropriate caregiver to facilitate obtaining the missing information. In some embodiments, missing information for the patient is imputed using information from similar patients identified by consumable content 3100. In some embodiments, the imputed information may be statistically imputed using information from similar patients, and statistical processes such as Monte Carlo simulation. Further, in some embodiments, imputed patient information is highlighted, color-coded, presented with a notice, or otherwise presented to a caregiver so as to enable a caregiver to identify imputed patient clinical data from actual patient clinical data.

Additional details regarding aspects of embodiments of mapping service 3100 are provided in U.S. patent application Ser. No. 13/645,896, filed on Oct. 5, 2012, which is herein incorporated by reference in its entirety.

With reference to FIG. 3B, a block diagram of one example embodiment of a system for facilitating clinical decision support is shown and referred to generally as system 3200. Each block in example decision support system 3200 is intended to show a component or step for providing decision support services 3201, including point-of-care services, mapping services, natural language processing services, new knowledge discovery, described in connection to FIGS. 4A-8D.

At mapping component 3240, a supervised learning algorithm facilitates the process of standardizing proprietary codes so that all clinical information elements or concepts are coded to appropriate standards, such as described in connection to FIG. 3A. In some embodiments, mapping component 3240 uses solver(s), inference engine(s), algorithm(s), rule(s), or plan(s) 3230 ("solver agent(s) 3230") (such as described in mapping services 3100 of FIG. 3A) to process data from data sources including population health data such as Cerner Health Facts 3220, literature and published evidence 3210, or other data sources (not shown) including real-time and near real-time or streaming data sources.

At EMPI component 3250, patient records and patient information from different systems or data sources are matched using a record-linking algorithm, that uses both clinical and demographic attributes, in some embodiments, thereby creating a complete shareable or inner-operable patient record. In an embodiment, the complete patient record made shareable in that it is mapped from a proprietary or first nomenclature to a standard clinical coding nomenclature (second nomenclature). As described above in connection to FIG. 3A and patient information data store 2110 of FIG. 1C, the component pieces of patient record information may be logically stored together in a complete patient record, or may be logically connected by reference pointers or addresses to one or more different patient records. In an embodiment component portions of a health record that are determined to be probable matches to a particular patient are provisionally linked to the patient record. In an embodiment, the provisional linkage may be confirmed by auditing. Additional information regarding of embodiments of EMPI component 3250, including identifying and linking patient records as they relate to the invention, are provided in U.S. patent application Ser. No. 13/874,961 filed on May 1, 2013, and U.S. Provisional Patent Application, 61/886,457 filed Oct. 3, 2013, each of which are herein incorporated by reference in its entirety.

Using the longitudinal patient record alongside a contextual decision support ontology framework and mathematical models or other services used by solver agents 3230, health care agents produce the appropriate outcomes for decision support services 3201.

Figure 3C:
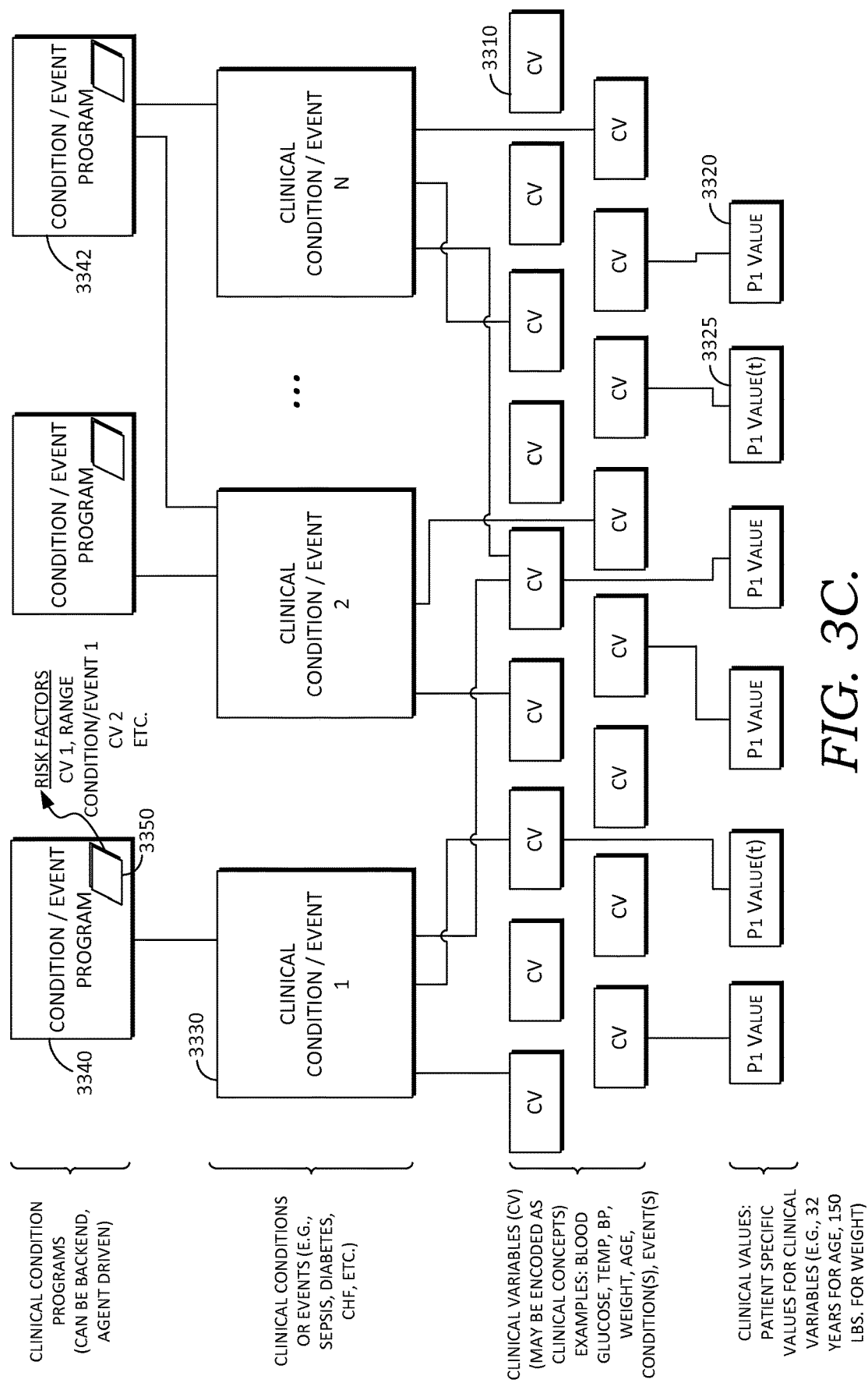
FIG. 3C illustratively depicts aspects of an exemplary operating environment suitable to implement embodiments of the present invention.

Turning now to FIG. 3C, an aspect of an exemplary operating environment showing an example of relationships between certain elements of decision support services is shown and referred to generally as environment 3300. Environment 3300 includes a plurality of clinical attributes/variables ("CV") 3310 (including demographic attributes), which may represent a category or type of clinical information about a patient such as BP, Respiratory Rate, weight, blood glucose, sex, age, condition(s), diagnoses, patient attribute, demographic, or other type of clinical information. A clinical variable 3130 may be associated with a clinical value 3220 or clinical value 3225, which may be a patient-specific value for a clinical variable, such as 132 lbs. for weight, 32 years for age, male for sex, or 120 SBP. In some instances, clinical value 3225 varies as a function of time. For example, a clinical variable for white blood cell may have clinical values that vary in time, which may be provided by a series of lab results. While a clinical value 3320 such as "male" or "female" for the clinical variable "sex" would not be expected to change for a patient. Clinical variables and clinical values may be associated with clinical concepts, and in some embodiments are capable of encoding into clinical concept codes.

Clinical variables 3130 may be associated with a clinical condition or event 3330. For example, the condition 3130 for diabetes may be associated with clinical variables 3130 for blood glucose and weight. In some embodiments, these associations represent discovered associations determined via mapping service 3100 of FIG. 3A. For example, new clinical variables associated with a "target" condition or event, in the form of "related concepts" are discovered, thereby forming newly identified relationships between a clinical condition/event 3330 and the clinical variable.

In some embodiments, condition/event program 3340 (condition program 3340) includes one or more plans (such as plan 2128 discussed in connection to FIG. 1C), algorithm(s), rules, courses, or guidelines for determining a patient's likelihood of having or developing one or more conditions or decision support events such as condition/event 3330. In some embodiments, condition/event program 3342 addresses multiple conditions or events, which may be concurrent and overlapping. In some embodiments, condition program 3340 (or 3342) may be considered associated with a particular state of the patient. For example, briefly referencing the patient condition state machine shown in FIG. 7A, a patient at a particular location or state of the state machine, which may correspond to multiple concurrent, overlapping conditions, may have a specific condition program for determining conditions risk scores, risk factors, and clinical information relevant to the condition(s). In some embodiments, the condition program is operated by an agent, which may be an agent dedicated to that particular condition program (such as a sepsis detection agent described in the example provided in connection to FIG. 1C), and in some embodiments, the condition program may be dynamically created or selected from a library, based on the particular state of the patient. For example, a specific condition program may be used for the pregnant patient with heart failure (shown in the state machine of FIG. 7A). In this manner, condition programs may be tailored to the particular patient, rather than the condition itself. Moreover, as described in connection to FIG. 1C, a condition program may be embodied as a learning, adaptive agent or agent-driven process. Specific condition programs may be evaluated and updated by swapping them out with superior performing programs.

Some embodiments of condition program 3340 (and 3342) identify a set of risk factors used for determining the particular condition(s) or event(s). Risk factors comprise a set of clinical concepts or clinical variables (with clinical values) that are determined to be relevant to a condition, including a decision support event, that may be used for determining a patient's likelihood for having or developing the condition. In some embodiments and scenarios, condition risk factors can include other conditions. For example, a condition program for determining a patient's likelihood of CHF readmission might include COPD and diabetes as risk factors. While both the diabetes and COPD risk factors might also have dedicated condition programs, applied to the same patient, for determining their likelihood, in some embodiments. As new risk factors are identified, such as by identifying concepts related to a targeted condition or concept, as described in connection to service 3100 of FIG. 3A, the condition program can be updated. In some embodiments, the updated condition program is effectively "pushed out" to client sites, such as point-of-care applications by caregivers to patients. For example, suppose a newly related concept, such as a particular clinical variable, is discovered to be statistically associated with diabetes via the process described in FIG. 3A. This concept related to diabetes (which may have its machine-determined relation audited or vetted, in some embodiments) may become a new risk factor for diabetes. A condition program for diabetes, or a content table 2124 (FIG. 1C) used by an agent dynamically assembling a condition program that includes diabetes, can be updated to include the new risk factor. Where the condition program is currently in use, such as at a particular client site, the program may be dynamically updated to include the new risk factor. In some embodiments, dynamic updating occurs when communication occurs between the client application (such as PowerChart or an application such as described in FIGS. 5A-5F) and backend services, such as cloud services of FIGS. 2B and 2D. The resulting update may cause a particular patient's risk score or probability for the condition to change or may result in prompting the caregiver to provide patient information related to the new risk factor, in some embodiments.

Figure 3D:
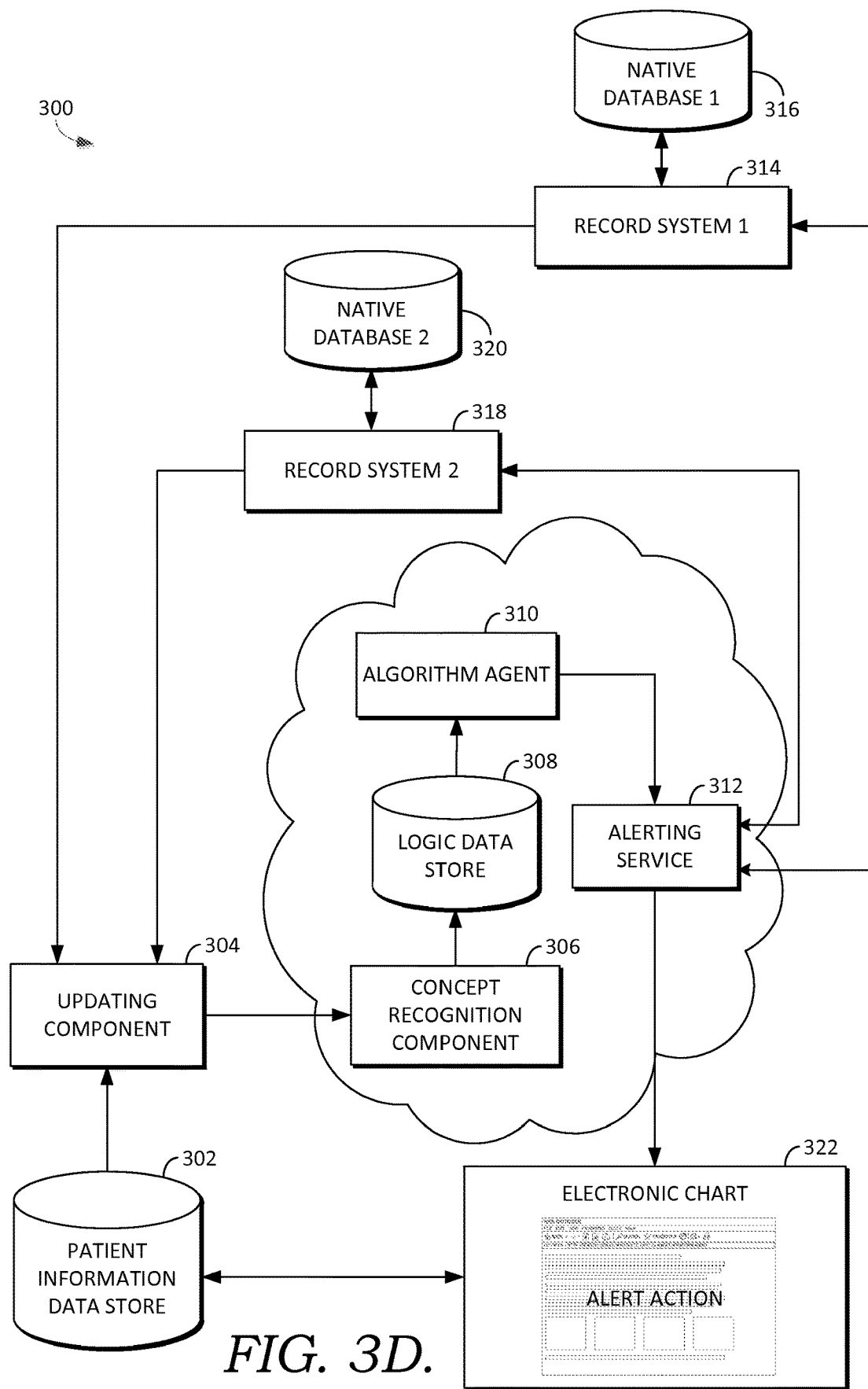
FIG. 3D depicts a block diagram of an exemplary systems for facilitating clinical decision support in accordance with embodiments of the present invention.

Turning now to FIG. 3D, with reference to FIGS. 1C, 1D, and 3A, a block diagram of an exemplary system 300 is shown for enabling multi-site data applications, such as monitoring or surveillance using data from separate data sources, and decision support for a patient's medical care. A patient information data store 302 is illustrated that stores information including patient records, such as electronic medical records (EMR) that can be accessed by various applications. For instance, a particular patient's EMR may be accessed by one or more providers associated with different medical organizations. In some embodiments, data store 302 includes the data store of patient information 2110 of FIG. 1C. Further, in some embodiments, a patient's EMR may not be accessed by a particular provider at a particular medical organization, but may be populated by patient information received from that provider at the medical organization. For example, multiple medical organizations, including hospitals, clinics, doctors' offices, etc., may treat the same patient at some point in time, but may not share a common medical record system, and thus may not all have access to the patient's EMR. Instead, these medical organizations may send patient information to a location that stores the patient's EMR so that this information can be populated into the EMR. This patient information may also be monitored and used to determine whether the patient is at risk of developing a particular disease or condition using an appropriate condition program.

The patient information can be returned by one of several methods. For instance, the updating component 304, in one embodiment, acts as a crawler and actually reaches into another medical organization's medial record system to pull relevant information for a particular patient who is being monitored or who may be monitored in the future for being at risk for a particular disease or condition. In some embodiments, functions of updating component 304 are facilitated by one or more agents 2135. The updating component 304, similarly, may query the medical organizations medical record system to obtain this patient information. Using this method, the crawler may include a program or application that tells it exactly what type of information to retrieve. Alternatively, the updating component 304 may not have the capability or permission to crawl for patient information, but may receive patient information such that it is the responsibility of the medical organization treating the patient to send the patient information to the updating component 304. Using either method, the updating component 304 eventually receives patient information for concept mapping. A concept recognition component 306 performs synonymic discovery and is generally responsible for reconciling terms used by the various medical organizations, and in some embodiments is facilitated by one or more agents 2135. For instance, if a first medical organization calls a white blood cell count test WBC and a second medical organization calls the same test WC, the concept recognition component 306 would have this information stored to determine that both terms are referring to the same test. In some instances, the concept recognition component 306 reconciles the test results themselves, such as if two different medical organizations use a different measuring system. In some embodiments, concept recognition component 306 is embodied as one or more software services operating on multi-agent system 2130. In some embodiments, concept recognition component 306 uses aspects of mapping service 3100. Additional information about the capabilities and functionality of such embodiments as they relate to our invention is provided in U.S. patent application Ser. No. 13/569,781, filed on Aug. 8, 2012, which is herein incorporated by reference in its entirety.

In some embodiments, a logic data store 308 stores logic, such as a condition program, or content table information for facilitating creation of a condition program by an agent, that is used to determine when a patient is at risk for a particular disease or condition and may also include information specifying when it is the appropriate time to alert one or more medical organizations, the patient, the primary care provider, etc., that the patient is at risk based on the patient information received from the multiple medical organizations. In some embodiments, logic data store 308 includes one or more components of parameters 2120, such as solvers library 2122, rules 2121, and or content tables 2124. The concept recognition component 306 may communicate patient identifying information to the logic data store 308, including an identification of the patient.

Algorithm agent 310 is responsible for executing algorithms or logic, such as the logic stored in the logic data store 308. In some embodiments, algorithm agent is an agent 2135, which may be a solver agent(s) or an agent that invokes other solver agents. Algorithms or logic may comprise algorithms and/or logic from solvers library 2122, rules 2121, and or content tables 2124, in some embodiments, and further may be handled by one or more dedicated agents. The algorithms or logic determines when, based on an array, a patient is at risk for developing a particular disease or condition. Algorithm agent 310 may additionally be responsible for updating the logic based on results of patient monitoring. For example, in embodiments wherein multiple agents are invoked to determine when a patient is at risk for developing a particular condition, agent 310 may swap out less-effective agents or agent 310 may facilitate updating the logic to indicate which particular agent should be used or which variable range(s) or threshold(s) should be used, based on the analysis results of the parallel-operating agents.

In some embodiments, algorithm agent 310 may include a multi-agent system that has knowledge as to whether patients for which alerts are sent are actually diagnosed with the disease or condition for which they are being monitored. If the percentage is low or otherwise unacceptable as to the patients being diagnosed, the criteria for being at risk for that disease or condition may be altered such that alerts and notifications are sent when a different set of criteria is met. Further, the individual medical organizations or health care entities may have individual criteria that they use to determine when a patient is at risk, and thus when it would like to receive an alert from the monitoring system. Accordingly in some embodiments, condition programs may be tailored to the specific venue (and patient information presented to a caregiver, flexed to the venue). An algorithm agent 310 (or a plurality of agents 310) may monitor this information to determine when it is appropriate to alert, notify, etc., one or more medical organizations or other parties involved in the medical care of the patient. For instance, each provider with document-patient contact during a period of time that the active risk assessment array has been active may be notified, in one embodiment.

Alerting service 312 receives input from algorithm agent 310 as to when and whom to alert or notify. In an alternative embodiment, the alerting service 312 is responsible for using inputs from the algorithm agent 310 to determine when and whom to alert or notify. The alerting service 312 may comprise one or more rules that allow the alerting service 312 how to determine when to communicate an alert, notification, including updated condition programs, risk scores, risk factors, sets of relevant clinical information elements, clinical determinations, recommendation, or other outputs (including health care agent outputs). In one embodiment, each medical organization or healthcare entity that has provided patient information to the monitoring system receives an alert, notification, or update when the criteria are met for the patient being at risk for a particular disease or condition, which may be determined upon obtaining additional information about the patient, or when an update to a condition program results in an updated condition risk score. Further, in some embodiments, the patient may be alerted or notified via a text message, a telephone call, a letter, an e-mail, etc., so that the patient can initiate a follow-up appointment with the primary care physician or another provider. Even further, the primary care physician, while he or she may not have provided any patient information that was used in the array to determine that the patient is at risk for a particular disease or condition, may be alerted or otherwise notified. In some embodiments, the notification or alert is displayed in an electronic chart 322 corresponding to the patient, such as an EMR so that it can be used for future reference by other clinicians. In some embodiments, alerting service 312 facilitates displaying alerts or notifications on a graphical user interface, such as an embodiment of interface 142 of FIG. 1A.

While in some embodiments, the monitoring system establishes the criteria for determining whether a patient is at risk for a particular disease or condition, such as specified by a condition program, in another embodiment, each medical organization may use different criteria for determining whether a patient is at risk for a particular disease or condition, which may be indicated in the same condition program or in a separate condition program associated with that particular medical organization or health care entity. For instance, a first medical organization may use a heart rate criteria of above 95 beats per minute (bpm) for a patient being at risk for developing sepsis. A second medical organization may use a heart rate criteria of above 98 bpm (clinical value associated with a clinical variable) for a patient being at risk for developing sepsis. When a patient's heart rate is at 96 bpm and other criteria are met for being at risk for developing sepsis, the first medical organization may receive an alert, notification, or update (such as a risk score update), but the second medical organization may not receive an alert, notification, or update, in some embodiments. In these embodiments, the second medical organization may receive a notification indicating that the first medical organization received an alert, notification, or update (such as a risk score update) based on its criteria for sepsis. This may prompt the second medical organization to take a closer look at the patient's medical information to determine whether it needs to take action. While there are many different ways of implementing an alerting service 312, the previous examples are provided as illustrations as to how the alerts and notifications may operate and do not limit embodiments of the present invention. Other scenarios not specifically mentioned here are contemplated to be within the scope of the present invention.

As shown, alerting service 312 can notify the medical organizations (or other healthcare entity) by communicating a notification to the medical record system used by each medical organization. For instance, the first medical organization may utilize record system 1 (item 314), which has a native database 1 (item 316) that stores patient information including EMRs for each of the medical organizations with which it operates. The notification may be communicated to record system 1 (item 314), and then the alert is sent to the particular medical organization or clinician within that medical organization. Similarly, the notification may be communicated to record system 2 (item 318), which has a native database 2 (item 320) for storing patient information including EMRs for each of the medical organizations with which it operates. The alert or notification may appear on the patient's EMR, or may be sent directly to the clinician responsible for treating the patient. As shown in FIG. 3D, the medical record systems send patient information to the updating component 304. This patient information may be used, such as specified by a condition program, to determine whether a patient is at risk for a particular disease or condition. While the patient information comes from individual medical organizations or health care entities, each medical organization may utilize a particular medical record system, and thus when the practitioner enters patient information into the patient's EMR at the medical organization (e.g., hospital, urgent care, doctor's office), the patient information is sent to the medical record system where it is stored. The alert sent from the alerting service 312 may take many forms, including, for exemplary purposes only and not limitation, an email, text message, telephone call, pager message, fax, or the like. Even further, the alert or notification may comprise a recommended care plan for the provider based on the patient information received.

As shown in the embodiment of FIG. 3D, the concept recognition component 306, the logic data store 308, the algorithm agent 310, and the alerting service 312 are in the cloud. In some embodiments these components, services, and data store are implemented on a cloud-computing platform. Cloud computing generally refers to a way for on-demand network access to a shared pool of configurable computing resources, including, for instance, networks, servers, storage, applications, or services. As such, the components listed above in the cloud are accessible by way of the Internet or other network 175 of FIG. 1A. While these components are shown in the cloud, other components may also be in the cloud, although not shown in FIG. 3D.

Figure 3E:
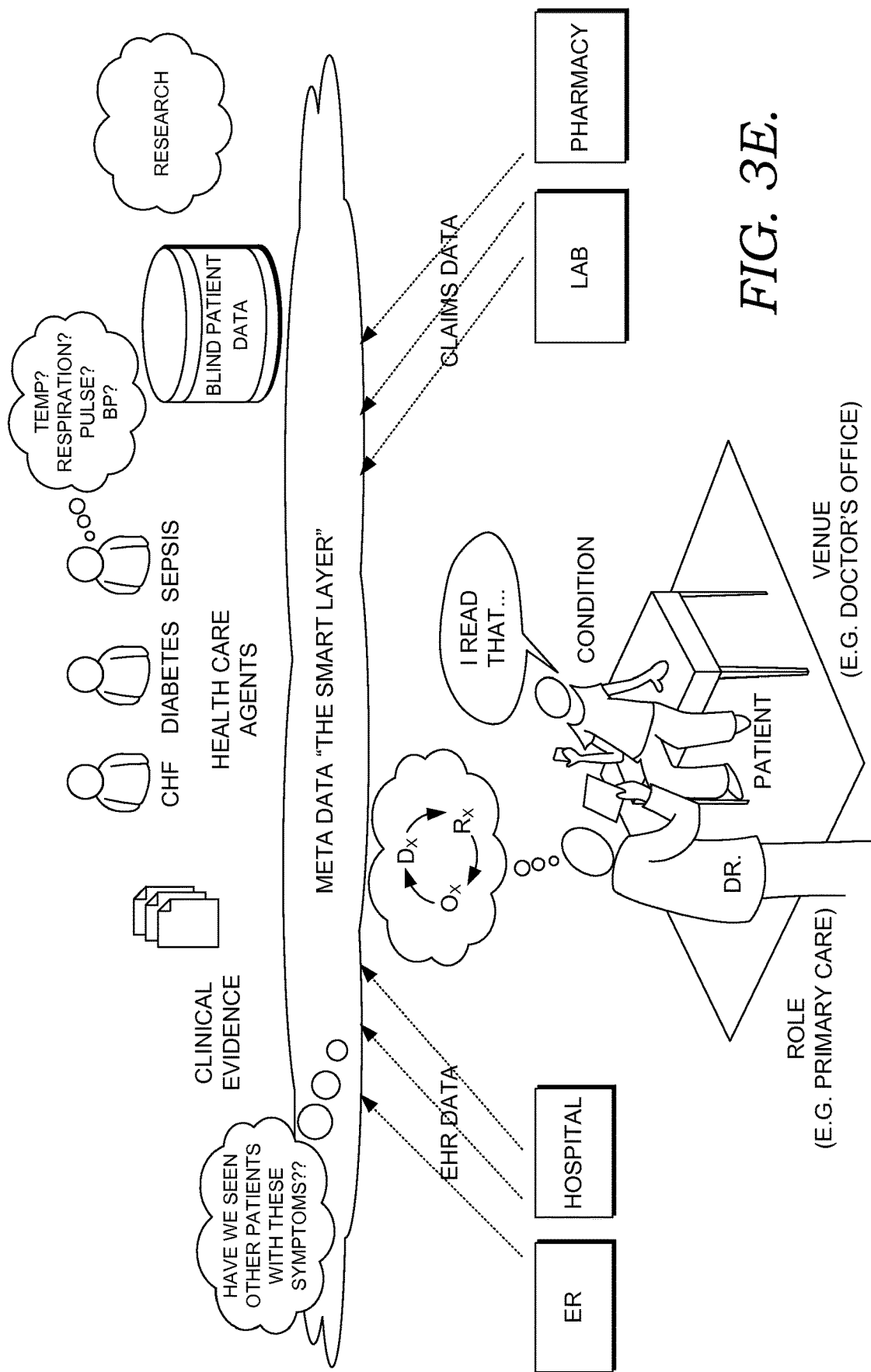
FIG. 3E depict aspects of an exemplary operating environment suitable to implement embodiments of the present invention.

With reference to FIG. 3E, aspects of an example operating environment are shown. FIG. 3E is intended to provide another example of an illustrative overview of how various aspects of the embodiment described herein (such as in connection to FIGS. 4A through 5F) operate in a health care environment, such as shown in FIG. 3B. As shown in FIG. 3E, a patient is being treated by a caregiver (labeled "DR"). The patient has a condition, the venue is the doctor's office, and the role of the caregiver is a primary care physician, in this example. The role venue and condition (RVC) establish a context for evaluating the patient and determining treatment including order, recommendations, determinations, and the like (e.g., Ox, Rx, and Dx). FIG. 3E shows information from patient health records (EHR data) and also claims data entering a "metadata smart layer" which may be facilitated by the processes described in connection to FIG.

3A. In some embodiments, once the information is part of the smart layer, where it has been mapped to a standard nomenclature, indexed, made searchable, able to be queried, it is useable by services, applications, and/or agents, such as the health care agents shown. For example, an agent or service (or routine) may determine what other patients have been seen with symptoms like the patient shown in FIG. 3E. Some agents are dedicated to particular conditions, such as the Sepsis, CHF and Diabetes patients shown, and may use information from the smart layer, research (which may be implemented as rules 2121, content parameters 2124, goals 2126, or plans 2128 of FIG. 1C, for example), clinical evidence, and blind patient data to determine patient risk for the condition. In an embodiment, some of the information in the smart layer is de_identified (i.e. patient-identifying information is removed and in some cases, clinical values are altered so as to preclude or make it difficult to determine the identity of a particular patient) and stored as blind patient data.

Turning now to FIGS. 4A-4K, flow diagrams are provided illustrating exemplary methods of providing clinical decision support and services. The methods use embodiments of systems and services described herein, such as concept mapping services, condition programs, and healthcare agents, for example. Some embodiments of these methods facilitate decision making by dynamically displaying patient information based on treatment session context, such as the role of the caregiver or caregiver specialty (e.g., cardiologist, urologist, social worker, etc.), the treatment venue, such as a research hospital, walk-in clinic, emergency room, and one or more conditions or clinical decision support events associated with the patient. Accordingly, in some embodiments, the information presented flexes or changes based on this context. For example, a cardiologist treating a heart-attack victim in an ER may be shown a particular type of patient information such as patient vitals, medications, and previous heart condition diagnoses; while an endocrinologist treating a diabetic patient at a research hospital may be shown clinical studies in which the patient is enrolled and patient compliance with prescribed condition management regimens, for example. Further, it is contemplated that in some embodiments, information presented flexes based on user-caregiver preferences. For example, a particular caregiver may always prefer to see patient vitals. Still further, in some embodiments, user-caregiver interaction with an application, such as described in connection to FIGS. 5A-5F, is received and processed to determine preferences associated with particular contexts, including role, venue, and condition. Thus, for example, a first-time user endocrinologist may be presented with information based on the learned preferences of other endocrinologist or further, based on the preferences of other endocrinologist treating similar patients in similar venues. In this manner, embodiments of the system are made to be adaptive and capable of learning. In some embodiments, this data mining of user interactions is facilitated by an agent or software routine.

Figure 4A:
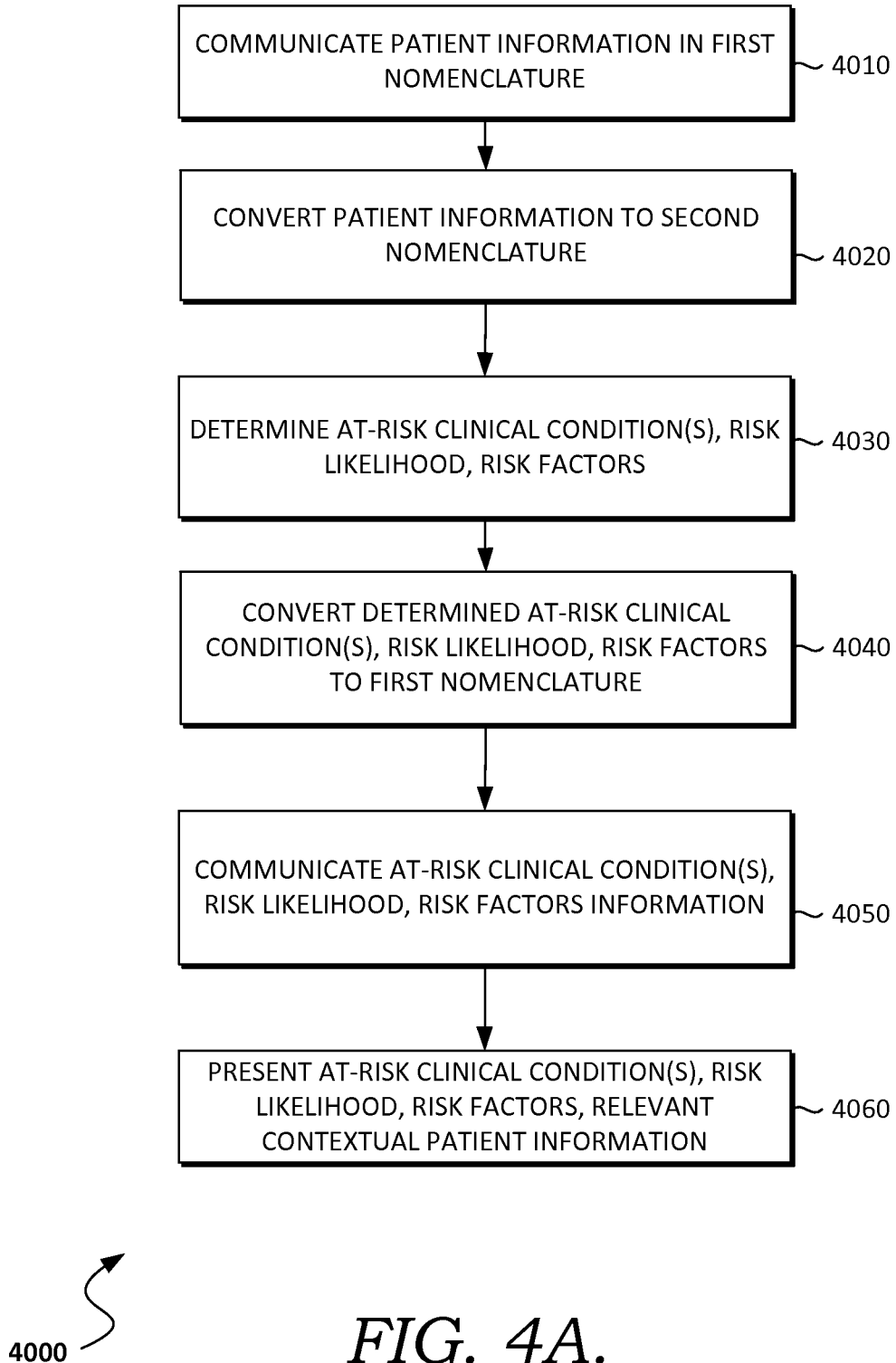
FIGS. 4A-4K depict flow diagrams illustrating exemplary methods of providing clinical decision support and services in accordance with embodiments of the present invention.
Figure 5A:
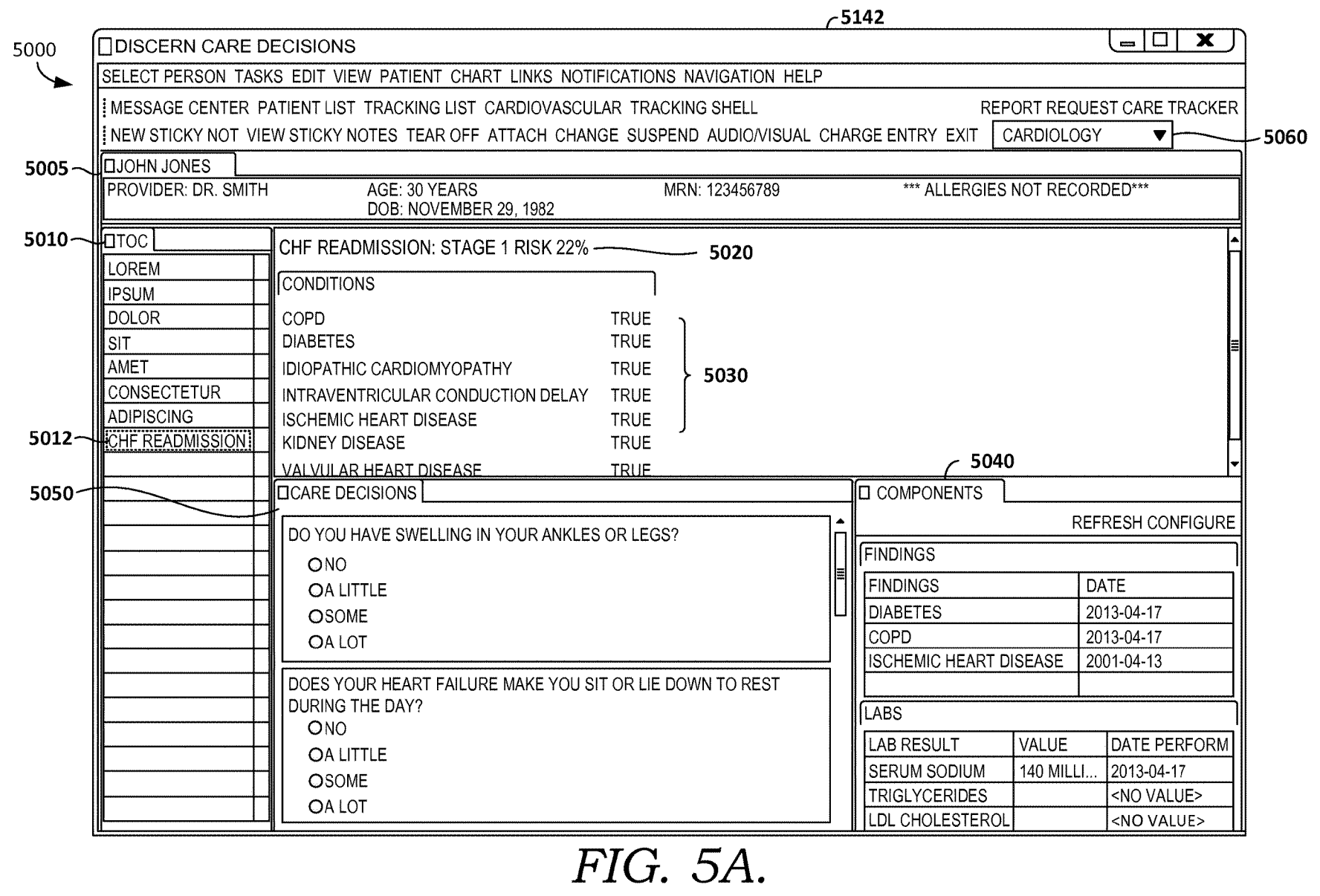

With reference to FIG. 4A, a first flow diagram is provided which depicts an embodiment of a method for facilitating clinical decision support through a user interface, such as shown in FIG. 5A, which is generally referred to herein as 4000. Method 4000 comprises, at step 4010, communicating a portion of patient health data, the portion of patient health data including a set of clinical concepts for a patient encoded in a first nomenclature associated with a healthcare entity. In some embodiments, the communicated data may be received by a backend server or agent, and may include receiving in the first nomenclature: (1) one or more clinical conditions for the which the patient may be at risk; (2) a computed likelihood of the patient having each of the one or more clinical conditions; (3) information identifying a set of risk factors associated with each of the clinical conditions relevant to the patient's risk for each of the clinical conditions, each risk factor corresponding to one or more clinical concepts. At a steps 4020 through 4040, at-risk clinical condition(s), computed likelihood, and set of risk factors are determined based on converting of the portion of patient clinical concepts or health data from the first nomenclature to a second nomenclature (step 4020); utilizing a condition program to determine (1), (2), and (3) in the second nomenclature (step 4030); and converting information representing (1), (2), and (3) from the second nomenclature to the first nomenclature (step 4040). At a step 4050, the determined information is communicated to the client or application at the point of care. At step 4060, the determined information is presented to an end user-caregiver, such as through provider/clinician interface 142 or FIG. 1A, using a graphical user interface, such as shown in FIG. 5A. In some embodiments, step 4060 comprises presenting a clinical conditions menu (or table of contents ("TOC")) presenting one or more clinical conditions for which the patient may be at risk; and presenting a condition risk area, responsive to selection of one of the one or more clinical conditions for which the patient may be at risk, the condition risk area comprising: a computed likelihood of the selected condition; a set of risk factors for the selected clinical condition, and a clinical value for at least a portion of the risk factors, such as shown in FIG. 5A. In some embodiments, it is contemplated that method 4000 is carried out on a single device at the point-of-care location.

In some embodiments of method 4000, clinical concepts comprise lab results, test results, patient conditions, patient health history, patient demographic information, or other discretized health-related information; clinical conditions include a disease, diagnoses, medical issue, or medical event; the computed likelihood is a calculated probability that the patient has or will develop the condition based on the clinical concepts for the patient; risk factors comprise one or more clinical variables of health data (e.g., clinical variables and associated clinical values) from population of patients that are determined to contribute to the likelihood that a given patient has or will develop the condition; and a clinical information element (or component) comprises specific lab results, tests, health-related findings, patient conditions, patient history, or other clinical-information component of a patient's health data.

In some embodiments, steps 4020-4040 are carried out by a software agent operating on a distributed computing platform. In some embodiments, the presented computed likelihood of the selected condition and set of risk factors are dynamically responsive to changes in the condition care program.

Some embodiments of method 4000 further comprise presenting a clinical information area for displaying a set of clinical information elements from the patient's health data and associated with the selected condition. Some embodiments of method 4000 further comprise presenting a condition assessment area for presenting a contextually-driven assessment based on patient information relevant to diagnosing or treating the condition, and for receiving patient information in response to presenting the assessment, wherein the received information includes one or more clinical concepts encoded in the first clinical nomenclature. And some embodiments of method 4000 further comprise presenting a condition assessment area for presenting a contextually-driven assessment based on patient information relevant to diagnosing or treating the condition and determining the patient information is absent or stale in the patient health data.

Some embodiments of method 4000 further comprise receiving patient health information relevant to the one or more clinical conditions for which the patient may be at risk; communicating a second set of clinical concepts corresponding to the received patient health information encoded in the first nomenclature; receiving in the first nomenclature an updated computed likelihood of the patient having each of the one or more clinical conditions; and responsive to receiving the updated computed likelihood, dynamically determining the computed likelihood of the selected condition presented in the condition risk area.

Some embodiments of method 4000 further comprise receiving an indication of a change in the set of risk factors for a condition; and based on the indication, dynamically updating the set of factors presented in the condition risk area.

In another embodiment, a variation of method 4000 comprises communicating a portion of patient health data, the portion of patient health data including a set of clinical concepts for a patient encoded in a first nomenclature associated with a healthcare entity. The method further comprises receiving: (1) computing instructions for determining a likelihood of the patient having one or more clinical conditions; and (2) information identifying a set of risk factors associated with each of the clinical conditions relevant to the patient's risk for each of the clinical conditions, each risk factor corresponding to one or more clinical concepts, the information encoded in the first nomenclature, wherein the computing instructions and information identifying a set of risk factors having been determined based on: (a) converting of the portion of patient health data from the first nomenclature to a second nomenclature; (b) utilizing a condition program to determine (1) and (2) in the second nomenclature; and (c) converting information representing (1) and (2) from the second nomenclature to the first nomenclature. Based on the received instructions, information identifying a set of risk factors, and the patient health data, the method further comprises determining a likelihood of the patient having each of the one or more conditions; presenting a clinical conditions menu presenting the one or more clinical conditions for which the patient is determined to be at risk; and presenting a condition risk area, responsive to selection of one of the one or more clinical conditions for which the patient is determined to be at risk, the condition risk area comprising: (i) the determined likelihood of the patient having the selected condition; (ii) the set of risk factors associated with the selected clinical condition, and (iii) a clinical value for at least a portion of the risk factors.

Figure 4B:
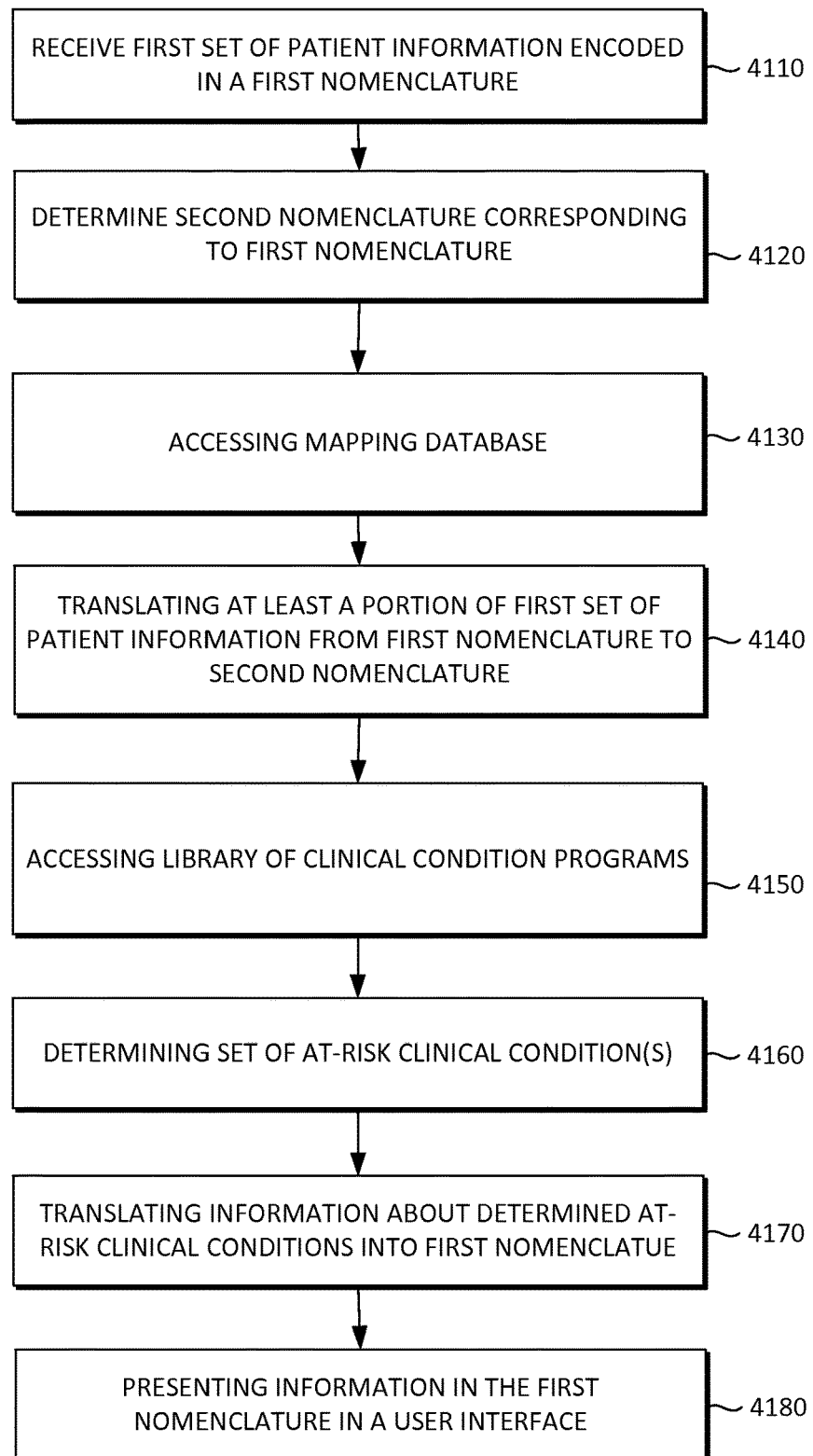

With reference to FIG. 4B, a flow diagram is provided which depicts an embodiment of a method for facilitating clinical decision support through a user interface, such as shown in FIG. 5A, which is generally referred to herein as 4100. Method 4100 comprises, at step 4110, receiving a first set of information about a patient, the first set of information including one or more clinical concepts encoded in a first nomenclature. At a step 4120, determining a second nomenclature corresponding to the first nomenclature. At a step 4230, accessing a mapping database of concept mappings between the first nomenclature and the second nomenclature. In some embodiments, a mapping database comprises a record or association of clinical codes of different clinical nomenclatures for the same clinical concept(s). At a step 4140, translating at least a portion of the one or more clinical concepts encoded in the first nomenclature into the second nomenclature thereby creating a second set of information about the patient including one or more clinical concepts encoded in the second nomenclature. At a step 4150, accessing a library of clinical condition programs, each clinical condition program associated with a set of clinical concept risk factors encoded in the second nomenclature. At a step 4160, determining one or more clinical conditions associated with the patient based on the second set of patient information and based on at least one of the clinical condition programs. At a step 4170, translating into the first nomenclature the determined one or more clinical conditions and set of risk factors associated with the condition program corresponding to each of the one or more clinical conditions. In an embodiment the same mapping database is utilized for the translating operation of step 4160. At a step 4180, presenting a user interface including a menu of condition items, each condition item corresponding to the determined one or more clinical conditions, wherein the conditions are presented using the first nomenclature. In some embodiments of step 4180, responsive to selecting an item in the menu, displaying a risk score for the patient having the condition corresponding to the item, and displaying a set of risk factors relevant to the risk score, wherein the risk factors are presented in the first nomenclature. In some embodiments of method 4100, mapping entries of the mapping database are determined by one or more software agents such as described in connection to FIGS. 1C, 2A, 3A, 3B, and 3D.

In another embodiment, a variation of method 4100 comprises receiving patient health data from a healthcare entity, the patient health data including a set of clinical concepts encoded in a first nomenclature. The method further comprises determining a second nomenclature corresponding to the first nomenclature; accessing a mapping database of mappings between the first nomenclature and the second nomenclature; from the first set of clinical concepts, determining a corresponding second set of clinical concepts encoded in the second nomenclature; and accessing a first clinical condition program which uses a subset of the clinical concepts in the second set of clinical concepts to determine a probability that the patient has a first clinical condition. Based on the first clinical condition program, the method further comprises determining that a patient has a probability for the first clinical condition; from the mapping database, determining a set of first-condition information including clinical concepts encoded in the first nomenclature and representing the first clinical condition, the determined probability that the patient has the first clinical condition, and the subset of clinical concepts used by the first condition program; and providing the first-condition information to the health care entity.

Some embodiments of method 4100 and the variation discussed above further comprise presenting in a user interface, a menu including the first clinical condition; and responsive to selecting the first clinical condition, presenting: (a) a condition risk score representing the determined probability that the patient has for the first clinical condition; (b) a set of risk factors corresponding to the subset of clinical concepts used by the first condition program; and (c) for at least a portion of the risk factors, a clinical value for the factor, the value determined information derived from the patient.

In some embodiments the first clinical condition program is implemented by a software agent and accessing a mapping database is facilitated by a software agent. In some embodiments at least one of the presented menu, the presented condition risk score, or the set of risk factors are dynamically responsive to changes in the first clinical condition program.

Figure 4C:
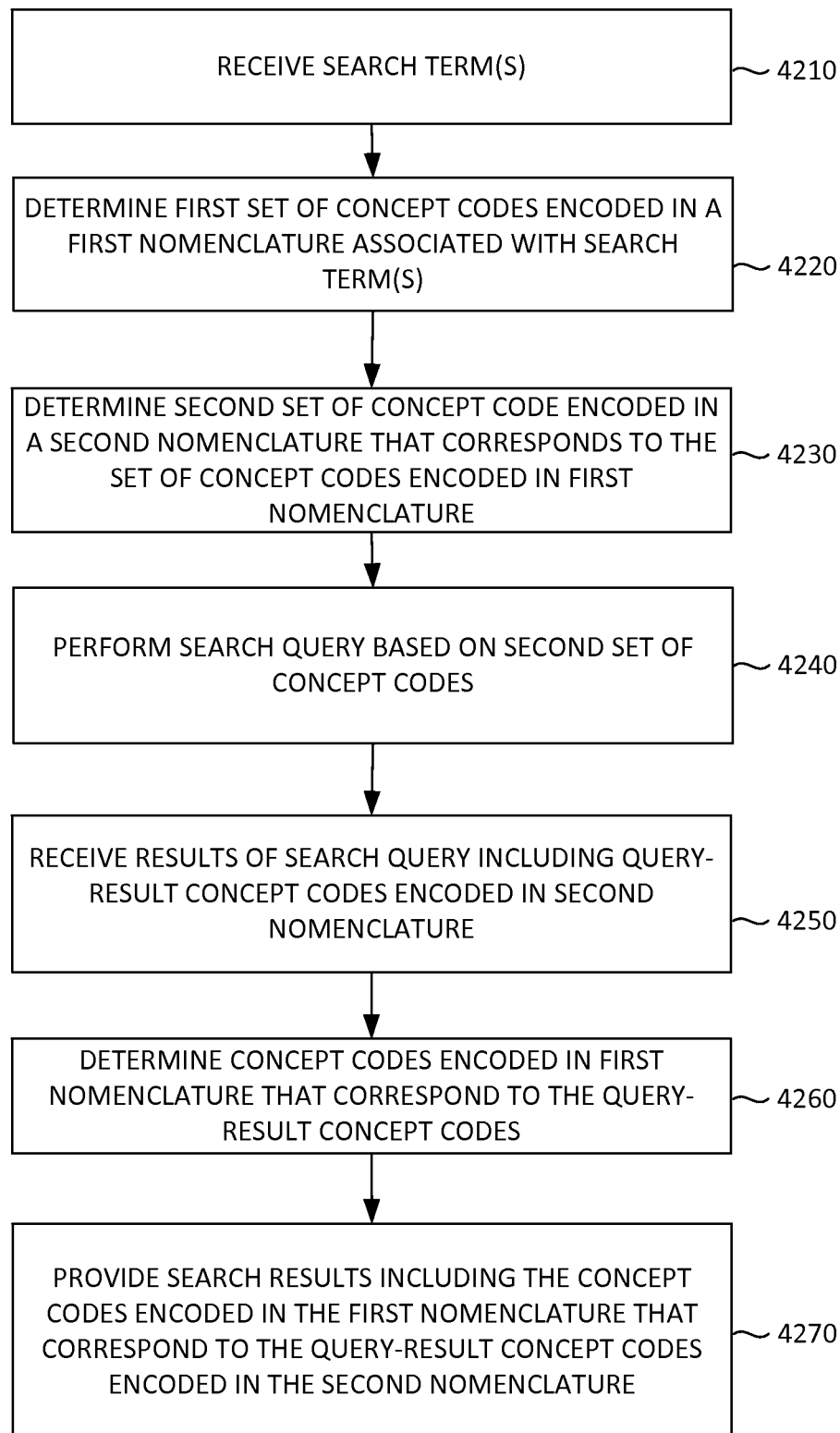

With reference to FIG. 4C, a flow diagram is provided which depicts an embodiment of a method for performing a search query of clinical information and providing query services through a user interface such as shown in FIGS. 6A-6D, in accordance with embodiments of the invention, and which is generally referred to herein as 4200. Some embodiments of method 4200 provide dynamic queries to users across data sourced from a plurality of records systems which may use different nomenclatures or ontologies, wherein the queries are provided in the local nomenclature or vocabulary (such as a proprietary nomenclature) used by a healthcare entity associated with the user, and based on the reverse code mapping of clinical concept codes such as described in connection to FIGS. 2A, 3A-3B, and 3D. In some embodiments, a local user can perform a search using a concept specified in his or her local vocabulary. The query is then performed on health information using a standardized concept code corresponding to the concept and query results are in the standardized concept code. The query results are then converted and displayed back to the user in the local vocabulary.

Method 4200 comprises, at step 4210, receiving one or more search terms for a search query. At a step 4220, from a first nomenclature of clinical concept-codes, determining a first nomenclature concept-code associated with each of the one or more search terms. At a step 4230, from a second nomenclature of clinical concept-codes, determining a second nomenclature concept-code corresponding to a first nomenclature concept code, for each of the determined first-nomenclature concept codes, thereby forming a set of second nomenclature concept-codes. At a step 4240, performing a search query based on the set of second nomenclature concept-codes. At a step 4250, receiving from the search query a set of search results including result concepts that are coded based on the second nomenclature of clinical concept-codes. At a step 4260, for each of the result concepts, determining a concept-code from the first nomenclature that corresponds to result concept code based on the second nomenclature. And at a step 4270, providing the set of search results including the result concepts, wherein the result concepts are coded based on the first nomenclature of concept codes.

In some embodiments of method 4300, a caregiver can initiate a query by selecting (such as right-clicking or holding-down on a touch surface) an item, such as a clinical element, presented on a graphical user interface, such as provider/clinician interface 142 of FIG. 1A. In some embodiments, a user can query on various alternative clinical decision events, actions, or courses of care for a patient. For example, using embodiments of the invention to identify patients having patient records with a target condition(s) and a set of concepts (including attributes) similar to a target patient, a caregiver for the target patient might perform a query to retrieve (1) the orders related to the condition that were issued for other patients; (2) information about which caregivers treated those patients; (3) how the patient condition was affected following the order; and/or (4) other future actions taken or events occurring with respect to the patients. Accordingly, in this manner, the caregiver is presented with information enabling the caregiver to choose an appropriate decision for the target patient, based on the orders issued for the similar patients and their outcomes.

In some embodiments, the query is received as a spoken command, such as a verbal request issued by a caregiver, patient, or other user. In some embodiments, concept mapping services, mapping agent(s), or synonymy agents are used for facilitating translation from a local (or first) nomenclature to a standard (or second) nomenclature.

Figure 4D:
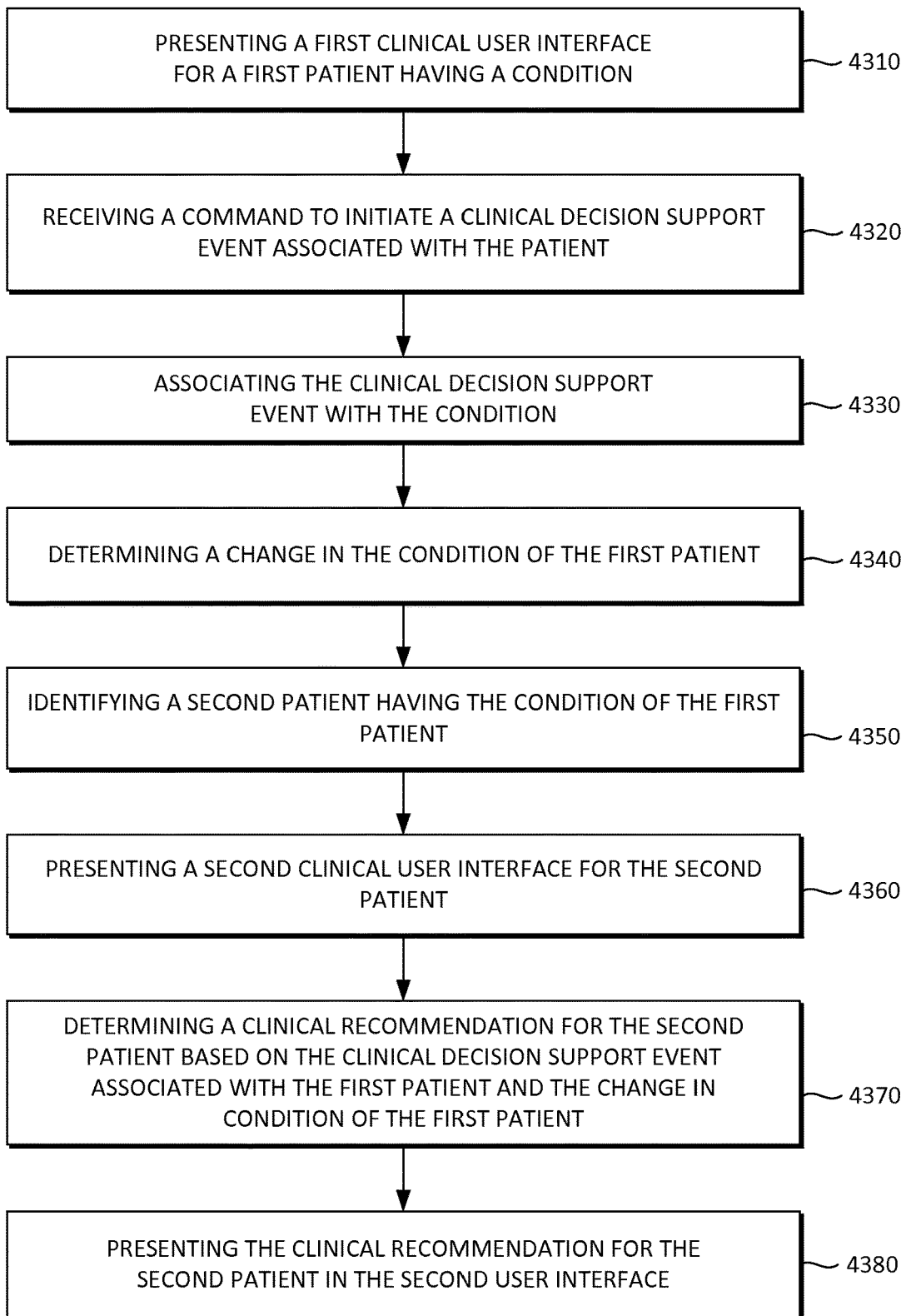

With reference to FIG. 4D, a flow diagram is provided which depicts an embodiment of a method for data-mining including identifying and mapping new knowledge, such as described in connection to FIGS. 2A, 3A and 3B, in accordance with embodiments of the invention, and which is generally referred to herein as 4300. In some embodiments, method 4300 includes machine learning from user-caregiver interaction of point-of-care user interfaces, such as the graphical user interfaces described in connection to FIGS. 5A-5F. In some embodiments, interaction-activity including queries, selections, recommendations, preferences, use-behavior, and patient information associated with the interaction is received and processed. In some embodiments, the received patient information is de-identified. In some embodiments, the processed information is structured or mapped, if necessary, such as by a mapping service 3100, and stored in a population health database, where it may be used for providing other services described herein, such as providing recommendations to a caregiver based on learned knowledge from data involving similar patients.

Method 4300 comprises, at step 4310, presenting a first clinical user interface associated with a first patient having a condition, the first clinical user interface including: (a) a clinical information area having a plurality of clinical information elements, at least a portion of the plurality of clinical information elements being populated with stored clinical information associated with the first patient; (b) a clinical recommendations area for presenting a clinical recommendation associated with the condition; and (c) a user-input area for receiving user commands. At a step 4320, receiving a command to initiate a clinical decision support event associated with the first patient. At a step 4330, associating the clinical decision support event with the condition. At a step 4340, determining a change in the condition of first patient. In some embodiments, this determination is performed based on monitoring the patient's condition, which may be facilitated by an agent. At a step 4350, identifying a second patient having the condition of the first patient. In some embodiments, a second patient (or a plurality of additional patients) having the condition similar to the first patient may be identified from consumable content 3170, using a process, such as described in connection to FIG. 3A, for identifying patients having patient records with the same condition(s) and set of concept(s), including attributes. At a step 4360, presenting a second clinical user interface associated with the second patient. At a step 4370, based on the clinical decision support event associated with the first patient and the determined change in the condition of the first patient, determining a clinical recommendation for the second patient. And at a step 4380, presenting the clinical recommendation for the second patient in the second user interface.

In some embodiments of method 4300, the clinical recommendation includes clinical concepts encoded using a local vocabulary or nomenclature, and in some embodiments, the received command is received in a first nomenclature and the clinical recommendation includes clinical concepts encoded in a second or standard nomenclature. In some embodiments, clinical concepts associated with the first patient are encoded in a first nomenclature and clinical concepts associated with the second patient are encoded in a second nomenclature.

In some embodiments of method 4300, identifying a second patient having a condition of the first patient comprises: determining a first set of clinical concept codes associated with the condition of the first patient; the first set of codes being encoded in a proprietary/first nomenclature; determining a second set of clinical concept codes that correspond to the first set of codes, the second set of codes being encoded in a standardized/second nomenclature; and searching patient health records to identify a second patient having clinical concept codes or patient information matching the second set of clinical concept codes.

Some embodiments of method 4300 further comprise determining a caregiver-user's response to the recommendation for the second patient and logging information indicating the user's response. In these embodiments, the caregiver's response may become a sensor or preceptor that determines a future epoch. In these embodiments, the patient's outcome following the caregiver's response may be used to weight or alter the recommendation for a third (and future patients) clinical concept codes or patient information matching the second patient.

Figure 4E:
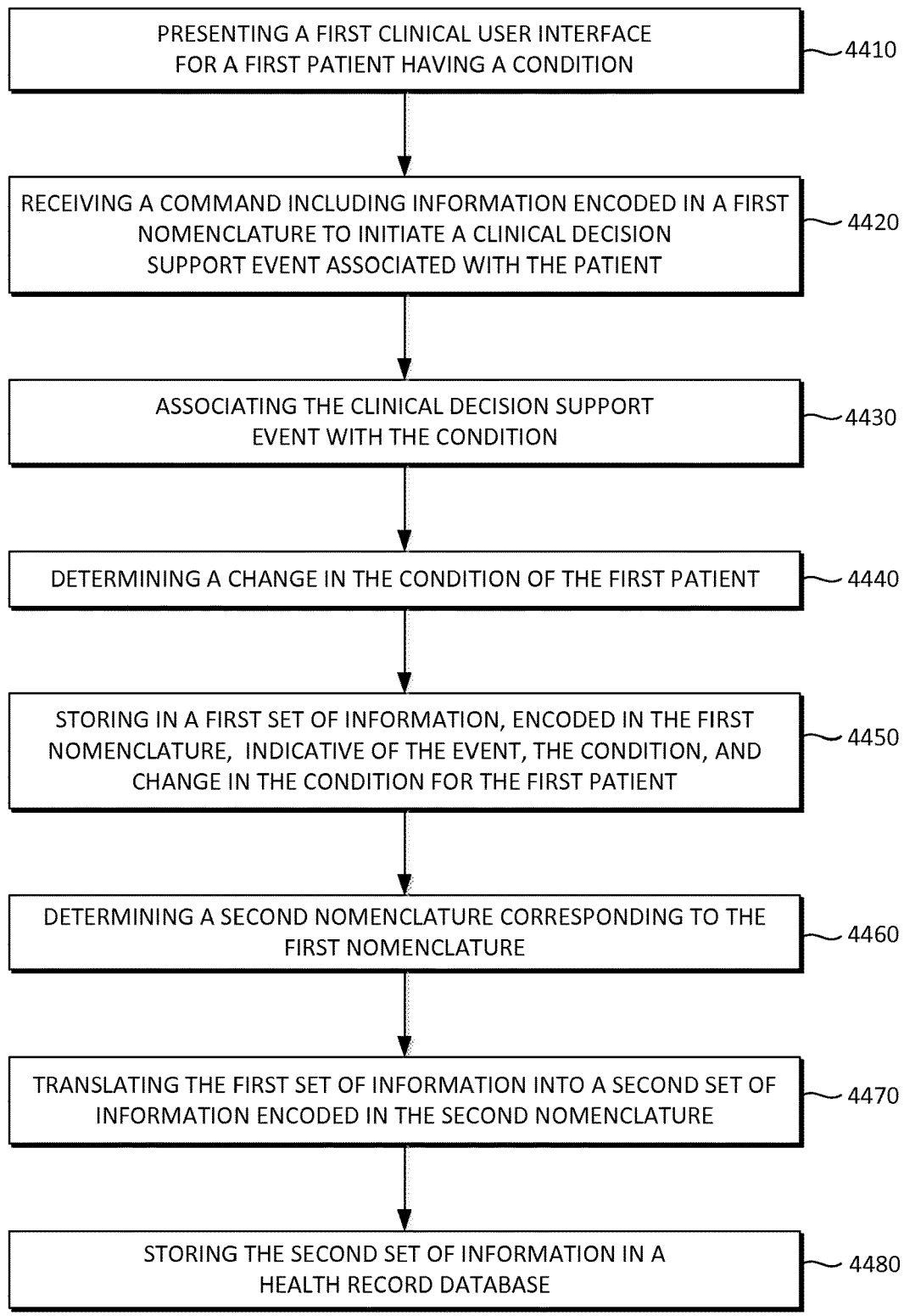

With reference to FIG. 4E, a flow diagram is provided which depicts another embodiment of a method for datamining including identifying and mapping new knowledge, such as described in connection to FIGS. 2A, 3A and 3B, in accordance with embodiments of the invention, and which is generally referred to herein as 4400. Method 4400 comprises at a step 4410 presenting a first clinical user interface associated with a first patient having a condition, the first clinical user interface including: (a) a clinical information area having a plurality of clinical information elements, at least a portion of the plurality of clinical information elements being populated with stored clinical information associated with the first patient; (b) a clinical recommendations area for presenting a clinical recommendation associated with the condition; and (c) a user-input area for receiving user commands. At a step 4420, receiving a command to initiate a clinical decision support event associated with the first patient, the event being encoded in a first nomenclature. At a step 4430, associating the clinical decision support event with the condition. At a step 4440, determining a change in the condition of first patient. At a step 4450, storing a first set of information for the first patient indicative of the event, the association with the condition, and the change in condition, the information encoded in a first clinical nomenclature. At a step 4460, determining a second nomenclature corresponding to the first nomenclature. At a step 4470, translating the first set of information encoded in the first nomenclature into a second set of information encoded in the second nomenclature. And at a step 4480, storing the second set of information in a health records database.

Some embodiments of method 4400 further comprise identifying a second patient having the condition of the first patient; based on the second set of information, determining a clinical recommendation for the second patient; and presenting the clinical recommendation for the second patient. In some embodiments of method 4400 the second set of information is stored as de-identified information.

In another embodiment, a variation of method 4400 may be used to determine a metric or rating associated with a particular caregiver. For example, a score indicating the effectiveness or efficiency of the caregiver at treating particular types of patients, a score reflecting an average cost or resource expenditure for treatments administered by the caregiver the caregiver, which may be normalized to other caregivers. The variation of method 4400 comprises identifying a first set of patients from other caregivers with similar sets of concepts; determining whether those patients got better or worse (e.g., cumulative number or average sum representing a change in status of a patient's condition); identifying a second set of patients from a target caregiver; determining an outcome associated with those patients, such as whether those patients got better or worse; comparing the target caregiver's patient outcomes to the outcomes of the reference set of patients, to determine a difference, and based on the difference, determining a score for the target caregiver. In some embodiments, the caregiver metric is based on treatment costs or use of resources by the target caregiver versus the costs or resource expenditure of the reference set of patients In some embodiments wherein machine learning services or agents are used to learn new knowledge, for scenarios where only little evidence is available (such as a limited number of patients) a higher weighting or priority is placed on recent information, rather than older or more stale information. Additional examples of providing priority for recent or newer learned patient information is described in U.S. Provisional Patent Application 61/798,123, filed on Mar. 15, 2013, which is herein incorporated by reference in its entirety.

Figure 4F:
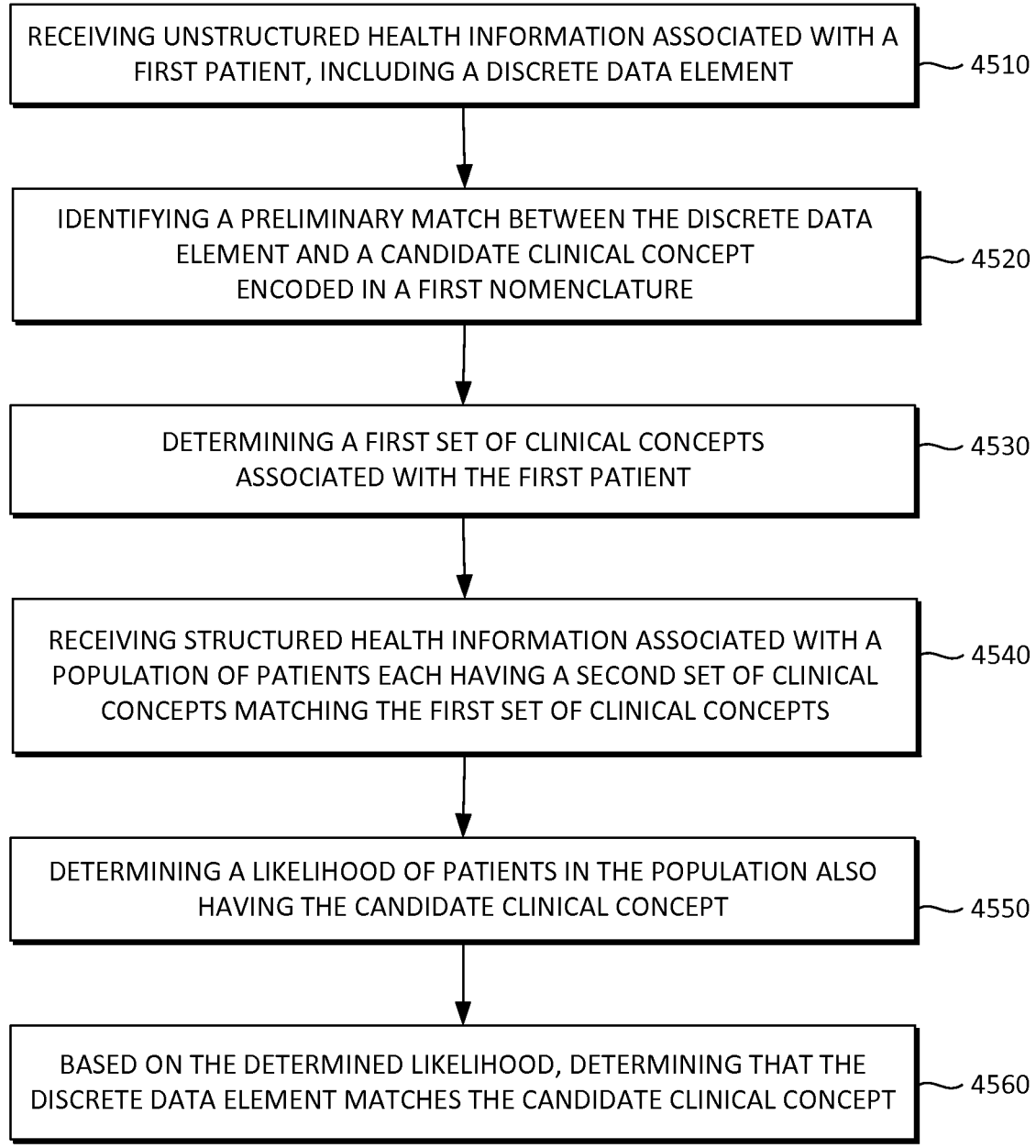

Turning now to FIG. 4F, a flow diagram is provided which depicts an embodiment of a method for providing natural language detection or processing (NLP), and which is generally referred to herein as 4500. In some embodiments and contexts, NLP may be referred to herein as medical language processing (MLP). Some embodiments of method 4500 provide enhanced NLP by correlating internal consistencies among patients, based frequently occurring associations of concepts, determined from the mapped content (e.g., consumable content 3170) of patient data. For example, suppose based on rudimentary NLP processing alone, a particular physician note appears to specify diabetes for a first patient. Embodiments of method 4500 identify other patients having sets of concepts in common with the first patient, and based on that association, confirm the outcome of the NLP processing. For example, if both the first patient and the other patients have insulin orders, and the other patients have diabetes, then it's likely that the first patient has diabetes.

Method 4500 comprises, at step 4510, receiving unstructured health-related data associated with a first patient, the health related data including a discrete element. In an embodiment, an NLP service, which may be embodied as a decoder program, software routine(s) or health care agent, is used in step 4510 to extract one or more discrete elements from the received unstructured health-related data. In an embodiment, the NLP service uses an open-source natural language processing system such as the Apache cTAKES (clinical Text Analysis and Knowledge Extraction System). In embodiment, the NLP service is modeled on the open-source UIMA (unstructured information management architecture) platform from IBM, the Open NLP natural language processing toolkit, or core NLP pipeline of the Open Health Natural Language Process (OHNLP) Consortium. In an embodiment, an NLP service is embodied as an agent 2135 or natural language processing agent, such as described in connection to FIG. 2C.

At a step 4520, identifying a preliminary match between the discrete element and a candidate clinical concept encoded in a first nomenclature. At a step 4530, determining a first-patient set of clinical concepts associated with the first patient. At a step 4540 receiving structured health-related data associated with a population of patients the structured health related data including, for each patient in the population, a set of clinical concepts matching the first-patient set of clinical concepts. At a step 4550, determining a likelihood of patients in the population also having the candidate clinical concept. And at a step 4560, based on the determined likelihood, determining that the discrete element matches the candidate clinical concept.

In another embodiment, a variation of method 4500 may be used to determine or identify a new ontology for a condition, which may include an emerging condition. At a first step, the variation of method 4500 comprises receiving unstructured patient health related data. At a next step, the method comprises performing natural language processing on the unstructured data to determine one or more clinical concepts from the unstructured data, wherein at least one of the concepts corresponding to a clinical condition of the patient, and the concepts are encoded in a first nomenclature. At a next step, associating the clinical concepts with each other, thereby forming a set of associated clinical concepts. At a next step, determining a second (or standardized) nomenclature corresponding to the first nomenclature. At a next step, translating the set of associated clinical concepts into the second nomenclature. At a next step, storing the set of associated clinical concepts in the second nomenclature. At a next step, from a database of health records, determining one or more similar sets of associated clinical concepts; and designating the clinical concepts as a contextual ontology for the clinical condition.

Figure 4G:
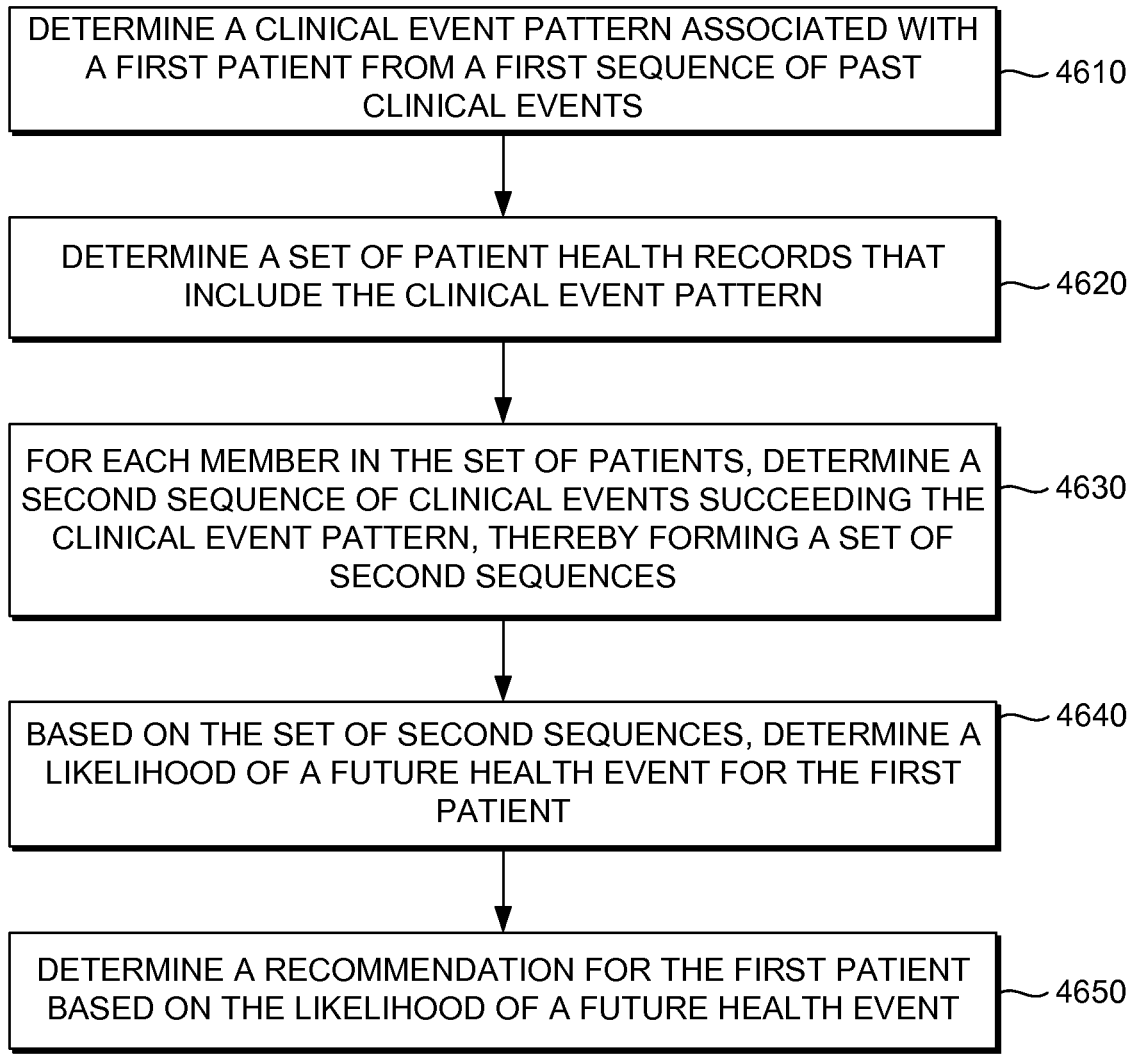

With reference now to FIG. 4G, a flow diagram is provided which depicts an embodiment of a method for providing decision support as it relates to directing the flow of care for a patient, such as provided in connection to FIGS. 7A-7D, and which is generally referred to herein as method 4600. In some embodiments of method 4600, a dynamic flow of care is provided (in contrast to the more rigid care plans or care pathways). For example, in some embodiments of method 4600, decision points in the course of care are identified and recommendations provided for next actions to take or avoid.

Method 4600 comprises at a step 4610, from a first sequence of past clinical events relating to a patient; determining a clinical event pattern associated with the patient. At a step 4620, from health record data associated with a population of patients, determining a set of patient health records that include the clinical event pattern. At a step 4630, for each member in the set of patient health records, determining a second sequence of clinical health events succeeding the clinical event pattern thereby forming a set of second sequences of clinical health events. At a step 4640, based on the set of second sequences, determining a likelihood of a future health care event for the patient. At a step 4650, providing a recommendation of a health care action to take based on the likelihood of the future event.

Some embodiments of method 4600 further comprise: for each member of the set of second sequences of clinical health events, determining a cost or resource expenditure associated with the sequence; determining a measure of improvement in the health condition at the end of the sequence as indicated by the health record associated with each sequence; and ranking the members of the set of sequences based on the measure of improvement and cost or resource expenditure. Some embodiments of method 4600 further comprise providing a recommendation of a care treatment sequence for the patient based on the ranking.

Variations of embodiments of method 4600 can provide identifying decision points (decision epochs or critical junctures) in care treatment, alerting caregivers that the patient is at or approaching a decision point, and providing a recommendation; anticipating likely future condition states, health-care resources needed, and costs associated with different treatment courses for a patient; and determining a recommended sequence of care based on learned outcomes from other patients having similar concepts and other patient information (including resources available to the patient).

Figure 4H:
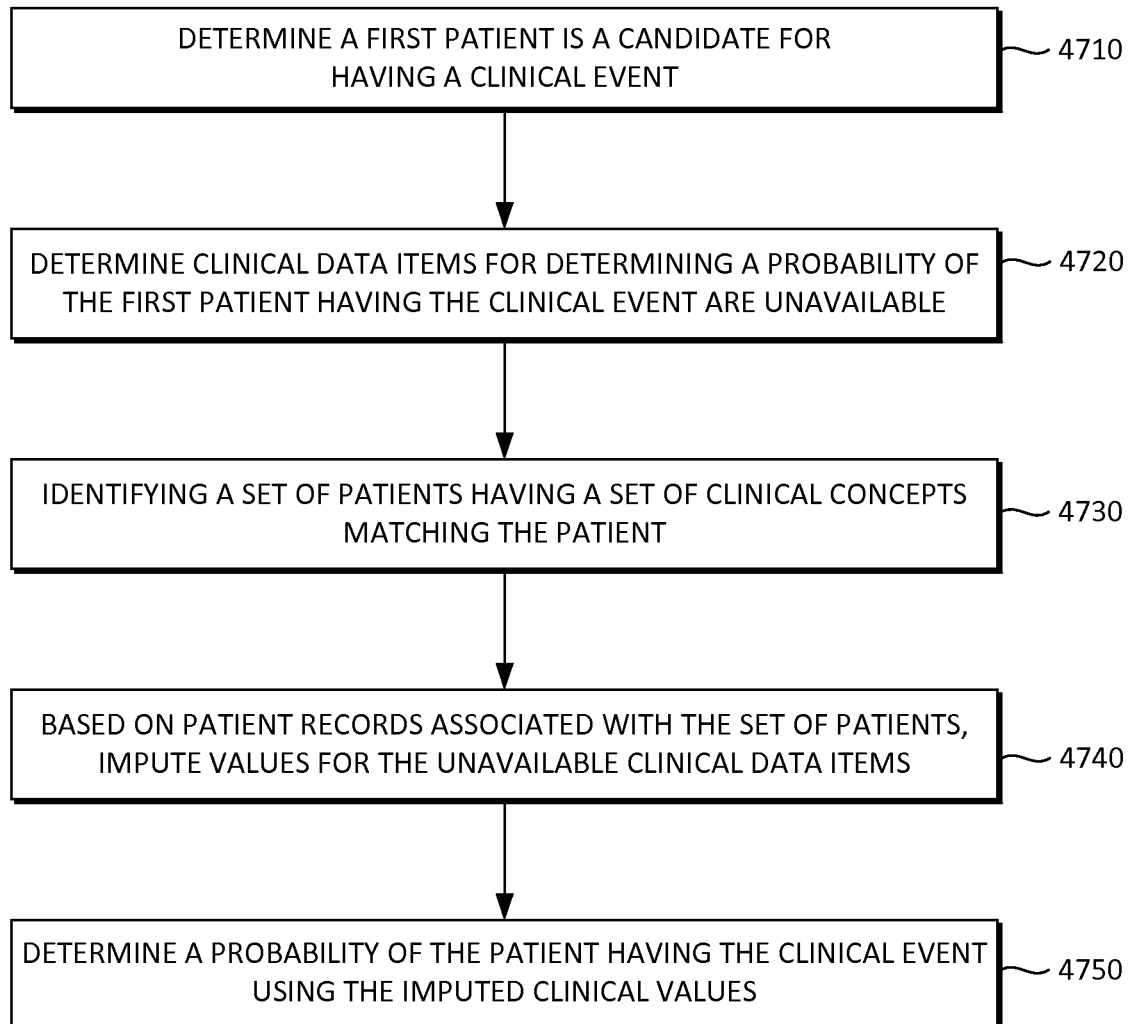

With reference now to FIG. 4H, a flow diagram is provided which depicts an embodiment of a method 4700 for providing decision support by imputing missing clinical patient data, such as patient data needed for determining a risk, test, or recommendation, for example, for a target patient, based on matching patient record information about the target patient to a set of similar patients having information related to the missing information. In some embodiments, the imputed patient data is presented in a manner so as to indicate to a caregiver that it is imputed and not actual patient data, as described above.

Method 4700 comprises at a step 4710, determining that patient has a probability for event (e.g., has a condition or risk for developing something). At a step 4720, determining that patient is missing clinical data needed for confirming the determined event probability, or for determining an increasing/decreasing probability. At a step 4730, determining that clinical information is not currently available for one or more of the clinical information elements relevant to the decision support event. At a step 4740, identifying a set of patients having similar clinical concepts associated with the condition. At a step 4750, imputing values for target patient's clinical data based on set of patients clinical data. And at a step 4760, using the imputed data to determine updated risk score/event. Some embodiments of method 4700 further comprise providing an indication of a difference in target patient's EHR between actual patient data and imputed data (e.g. color coding actual vs. imputed data).

Figure 4I:
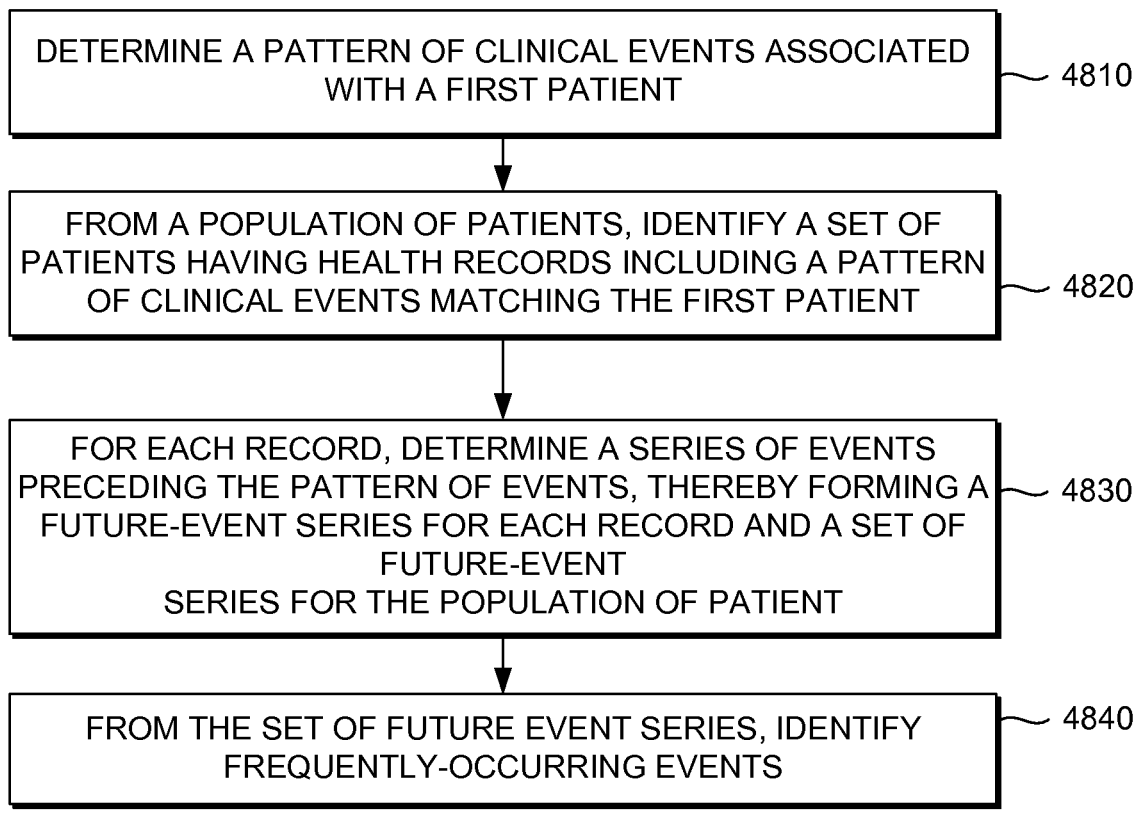

With reference now to FIG. 4I, a flow diagram is provided which depicts an embodiment of a method 4800 for providing decision support by identifying a decision point/epoch or critical juncture at future time for a patient, based on comparing event pattern information of the patient to event patterns of other similar patients. In some embodiments, an alert or notification is provided to a caregiver regarding an upcoming decision point.

Method 4800 comprises at a step 4810, for a patient, determining a pattern of clinical events. At a step 4820, from a population of patients, identifying a set of patient records with similar pattern of clinical events. At a step 4830, for each record, determining a series of events preceding the pattern thereby forming a "future event series" for each record. And at a step 4840, from the set of future event series, identifying frequently occurring events. In some embodiments, the identified events are designated as a "trigger" for starting a care program, or alerting a caregiver.

Some embodiments of method 4800 further comprise clustering the patient records by their change in condition (better, same, worse). Some embodiments of method 4800 further comprise for each cluster of records, determining a frequently occurring events among the future event series, thereby forming a frequently occurring set associated with each record cluster. In this manner a common step is identified for the "got-better", "same", or "got-worse" patients.

Some embodiments of method 4800 further comprise designating frequently occurring event a critical juncture, and some embodiments of method 4800 further comprise alerting caregiver of critical juncture thereby facilitating increased attention may be administered to patient.

Some embodiments of method 4800 further comprise obtaining additional information, such as spawning a dynamic assessment or prompting the caregiver for additional information to determine a next action to take regarding the patient's treatment. Some embodiments of method 4800 further comprise selecting care-pathway or future treatment program to implement for the patient. Some embodiments of method 4800 further comprise based on the frequently occurring events for each cluster, determining a recommendation for a target patient.

Some embodiments of method 4800 further comprise determining a degree of similarity between a target patient and the set of patient records; and based on the degree of similarity, which may include other clinical variables and patient attributes, determining a probability that the target patient will have one or more of the events in the future event series. Some embodiments of method 4800 further comprise determining a cost (costs include financial, risk including risks in compliance to quotas and expectations, and opportunity costs including resources expended) associated with each future event series. In some embodiments of this method two or more the records (of sets of records) are in different clinical nomenclatures.

Figure 4J:
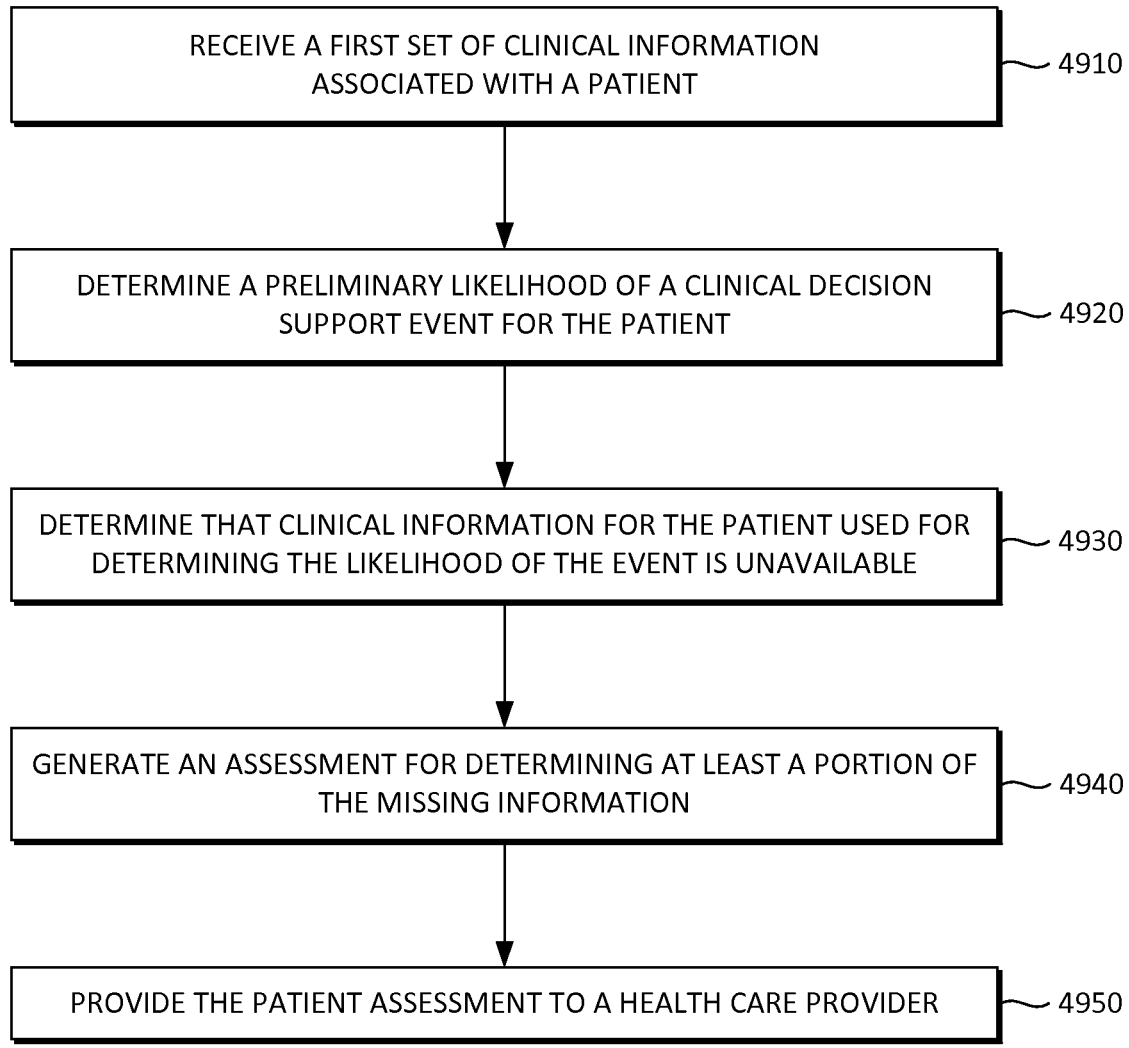

With reference now to FIG. 4J, a flow diagram is provided which depicts an embodiment of a method for providing decision support by providing an assessment to a caregiver to solicit additional information, such as described in connection to FIG. 5E, and which is generally referred to herein as method 4900. In some embodiments, an assessment is dynamically generated and may take the form of a context-based questionnaire. In some embodiments, branching logic is used (for example, additional questions are provided based on previously received answers), clinical order recommendations are provided in near-real-time, based on the answers, and the risk of the patient having a particular condition is updated in near-realtime based on the answers. In some embodiments, the questions may be determined from the mapped content of patient health records indicating concepts that frequently occur in association with a particular condition. In some embodiments, each question-answer pair corresponds to a coded clinical concept. In some embodiments, fuzzy logic is employed to determine questions.

Method 4900 comprises at a step 4910, receiving a first set of clinical information associated with a patient from a data store. At a step 4920, based on the first set of clinical information, determining a preliminary likelihood of a clinical decision support event being associated with the patient. At a step 4930, determining that additional clinical information is not currently available for one or more clinical information factors relevant to the clinical decision support event. At a step 4940, generating a patient assessment for determining at least a portion of the additional clinical information, wherein the patient assessment is generated based on a treatment-session context. And t a step 4950, providing the patient assessment to a health care provider treating the patient.

In some embodiments of method 4900, the clinical decision support event comprises a health condition; and the treatment-session context is determined based on at least one of the health care provider's clinical specialty, a clinical treatment-session venue, and the clinical decision support event.

Some embodiments of method 4900 further comprise receiving the at least a portion of the additional clinical information in response to providing the assessment, and updating the likelihood of a clinical decision support event based on the received additional clinical information. Some embodiments of method 4900 further comprise determining clinical advice based on the likelihood of a clinical decision support event. And some embodiments of method 4900 further comprise receiving the at least a portion of the additional clinical information in response to providing the assessment, and updating the determined clinical advice based on the received additional clinical information.

In some embodiments of method 4900, the assessment is provided via a graphical user interface such as depicted in FIG. 5E, and in some embodiments, the assessment comprises a series of questions, wherein an answer for a first question, received via the user interface, determines a subsequent question in the series of questions. In some embodiments of method 4900, the additional clinical information includes clinical concepts encoded in a first nomenclature. Some embodiments of method 4900 further comprise determining clinical advice based on the received answer to a first question and presenting the clinical advice in proximity to the first question.

In another embodiment, a variation of method 4900 comprises receiving a first set of clinical information associated with a patient from a data store. Based on the first set of clinical information, determining a likelihood of a clinical decision support event being associated with the patient. At a next step, accessing an assessment associated with the clinical decision support event, the assessment including a set of patient related questions. Determining from the set of questions a portion of the questions to include in a questionnaire, based on a treatment-session context and the first set of clinical information. At next step, generating a user interface for presenting the questionnaire; presenting the user interface to a user; and receiving a set of answers, via one or more clinical information elements of the user interface, in response to the portion of questions in the questionnaire.

Some embodiments of this variation further comprise based on the set of answers, determining an additional portion of questions from the set of questions to include in the questionnaire, and presenting the additional portion of questions. Some embodiments of this variation further comprise receiving a second set of answers to the additional portion of questions; determining clinical advice based on the first and second answers and the first set of clinical information; and presenting the clinical advice to the user. Some embodiments of this variation further comprise determining a clinical concept code associated with a first question and a first answer received in response to the first question; and storing the concept code in the first set of clinical information.

In some embodiments, the set of questions are determined based on health records for a population of patients, wherein each health record includes information corresponding to the clinical decision support event, and in some embodiments, the set of questions is further determined based on frequently occurring clinical concepts in the health records. In some embodiments, the set of questions is further determined by a health care software agent.

Figure 4K:
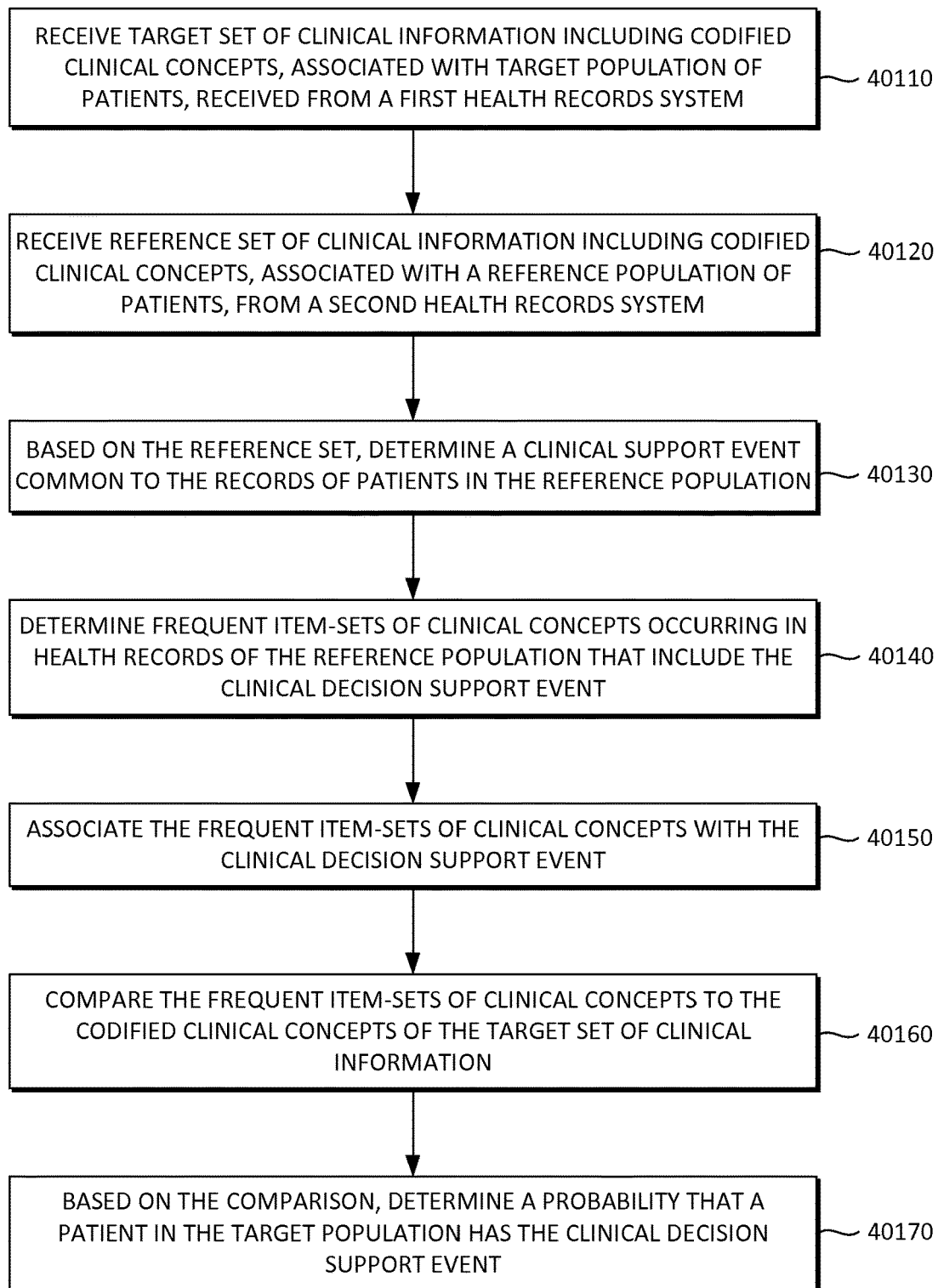

With reference now to FIG. 4K, a flow diagram is provided which depicts an embodiment of a method for learning new knowledge such as new related concepts, risk factors, treatments, and ontologies, such as described in connection to FIGS. 1C, 2A, 3A-3B, and 3D, and which is generally referred to herein as method 40100. In some embodiments, method 40100 facilitates discovering and validating latent relationships in a health care dataset or learning new concepts that are relevant to a particular clinical event, such as a health condition(s), based on utilizing the mapped or structured clinical data from patients having the same clinical event and/or frequently occurring related concepts. In some embodiments, the clinical event may include a health condition, multiple or concurrent conditions; one condition and a particular procedure or course of treatment; one condition, one procedure, and one medication; or similar combinations. Thus method 40100 may be used to determine new knowledge such as complex treatment procedures or sequences, that may be applicable to specific patients.

Method 41000 comprises at a step 40110, receiving a target set of clinical information associated with a target population of patients from a first set of records of a first health-records system, the target set of clinical information including one or more codified clinical concepts. At a step 40120, receiving a reference set of clinical information associated with a reference population of patients from a second set of records of a second health-records system; the reference set of clinical information including codified clinical concepts. At a step 40130, based on the reference set of clinical information, determining a clinical decision support event common to the records in the reference population of patients. At a step 40140, determining frequent item-sets of the clinical concepts associated with the reference population. At a step 40150, associating the frequent item-sets of clinical concepts with the clinical decision support event. At a step 40160, performing a statistical comparison between the frequent item-sets and the clinical concepts of the target set of clinical information to determining a statistical measure of association between the frequent item-sets and the clinical concepts of the target set. And at a step 40170, based on the statistical measure of association, determining a probability that the target population of patients includes the clinical decision support event.

In some embodiments of method 40100, performing a statistical comparison comprises: performing cluster-based matching of the frequent item-sets and the target set of clinical information to determine one or more clusters; determining at least one measure quantifying difference for at least one cluster; and determining a statistical measure of association based on the quantifying difference.

In some embodiments of method 40100, the clinical decision support event comprises a health condition, and in some embodiments, the clinical decision support event comprises a combination of health conditions or clinical procedures. In some embodiments of method 40100, the clinical concepts are codified using a standardized clinical nomenclature.

In another embodiment, a variation of method 40100 comprises receiving a reference set of clinical information associated with a reference population of patients from a plurality of health-records systems; the reference set of clinical information including codified clinical concepts. At a next step, based on the reference set of clinical information, determining a clinical decision support event common to patients in the reference population of patients. At a next step, from the reference set of clinical information, determining one or more sets of frequently-occurring clinical concepts. And at a next step, associating the one or more sets of frequently occurring clinical concepts with the clinical decision support event thereby forming one or more event indicators for the clinical decision support event.

Some embodiments of method 40100 or the variation further comprise receiving a set of clinical information associated with a first patient, the clinical information including codified clinical concepts; determining a number of the indicators in set of clinical information; and based on the number of indicators, determining a likelihood that the first patient has the clinical decision support event. Some embodiments of method 40100 or the variation further comprise presenting the determined likelihood to a user, and in some embodiments, determining a recommended clinical order for the patient based on the determined likelihood that the first patient has the clinical decision support event.

In some embodiments of method 40100 and the variation, the recommended clinical order is determined based on the reference set of clinical information associated with a reference population. Some embodiments of method 40100 or the variation further comprise accessing relevant clinical information from a plurality of data stores of different nomenclatures, and some embodiments further comprise using the learned set of risk factors for a condition program, which may include generating a condition program based on the set of risk factors. And some embodiments further comprise using the learned set of risk factors for diagnosing and predicting a patient's condition.

Figure 5B:
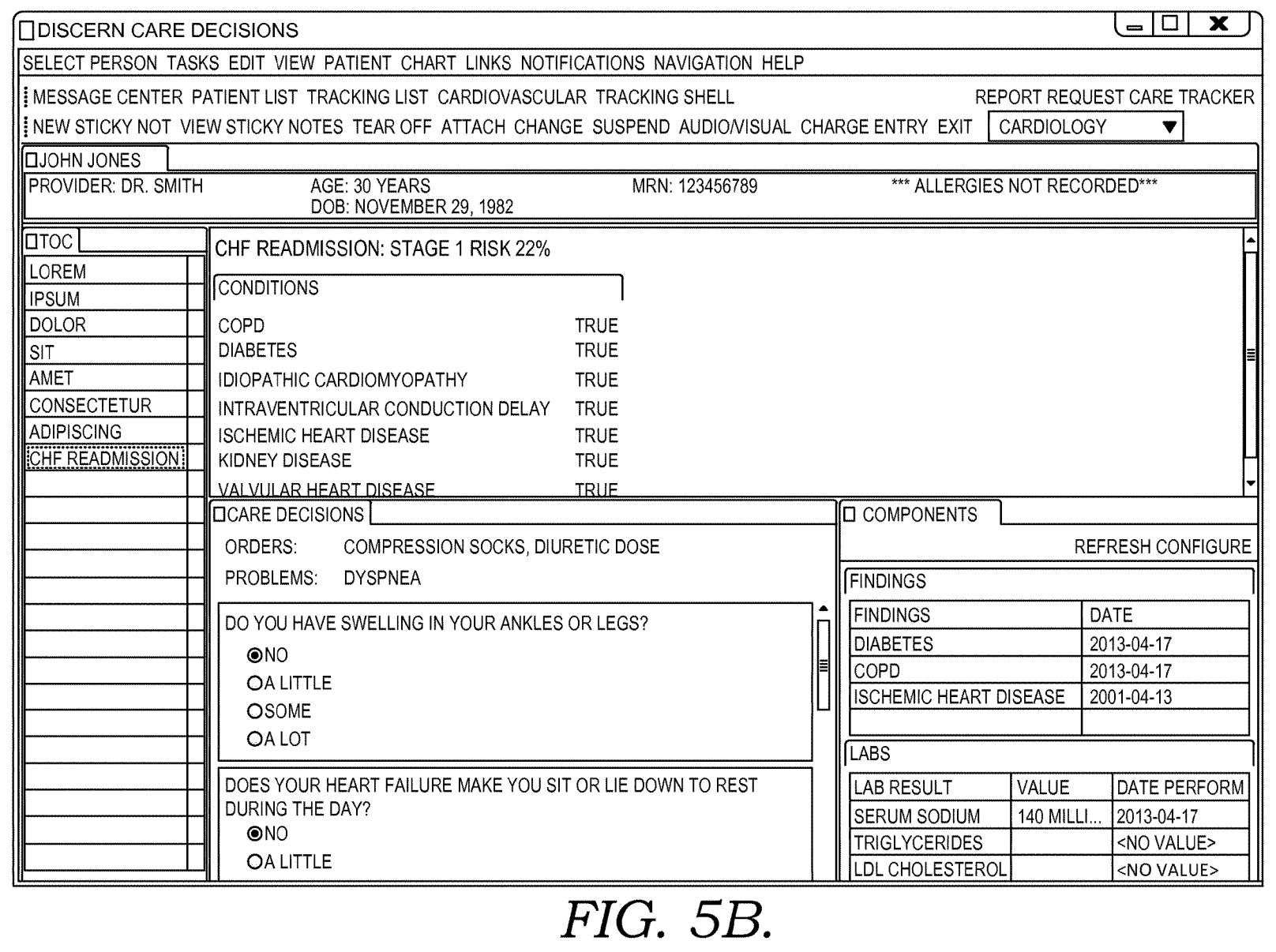
Figure 5C:
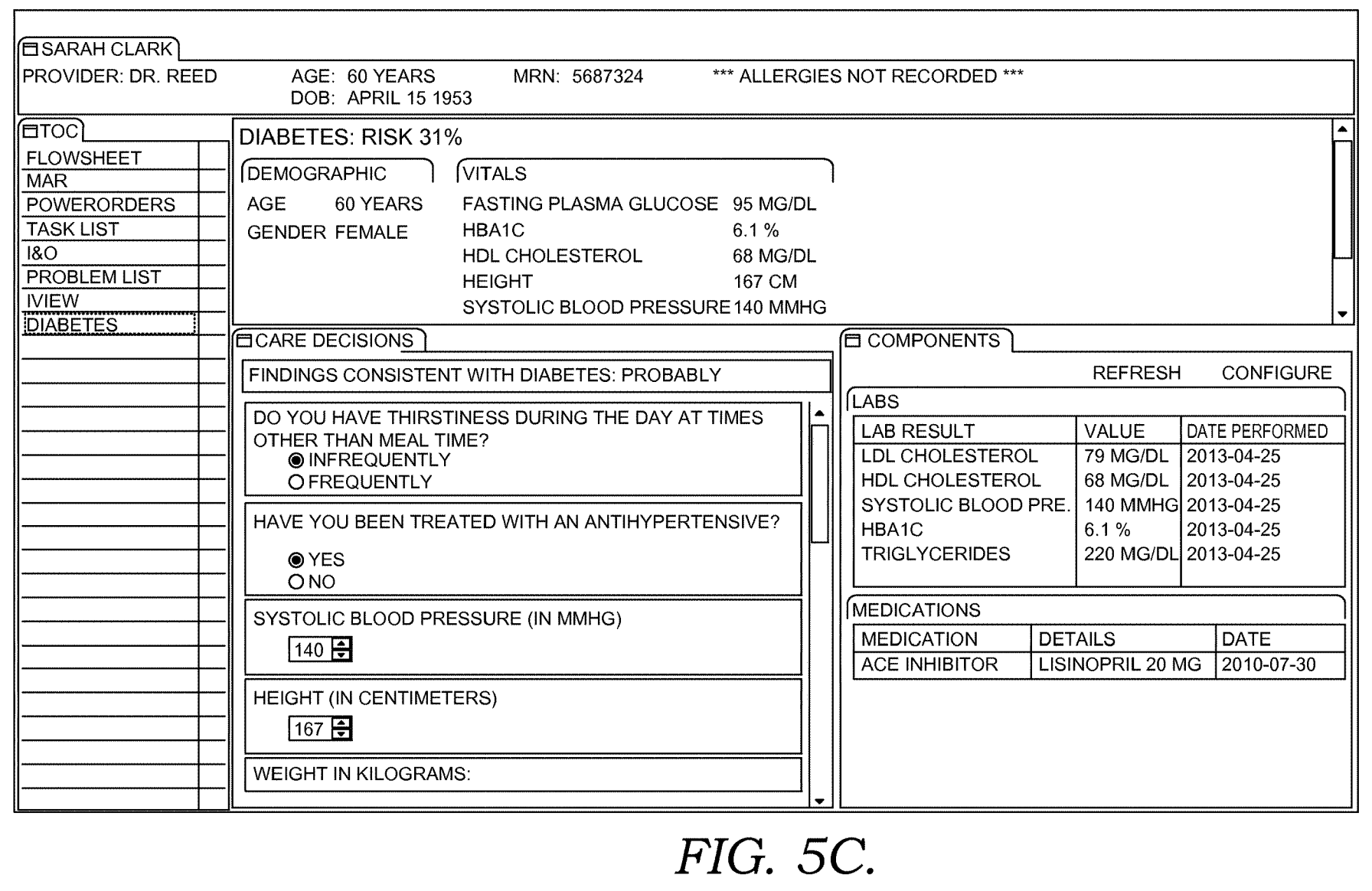
Figure 5D:
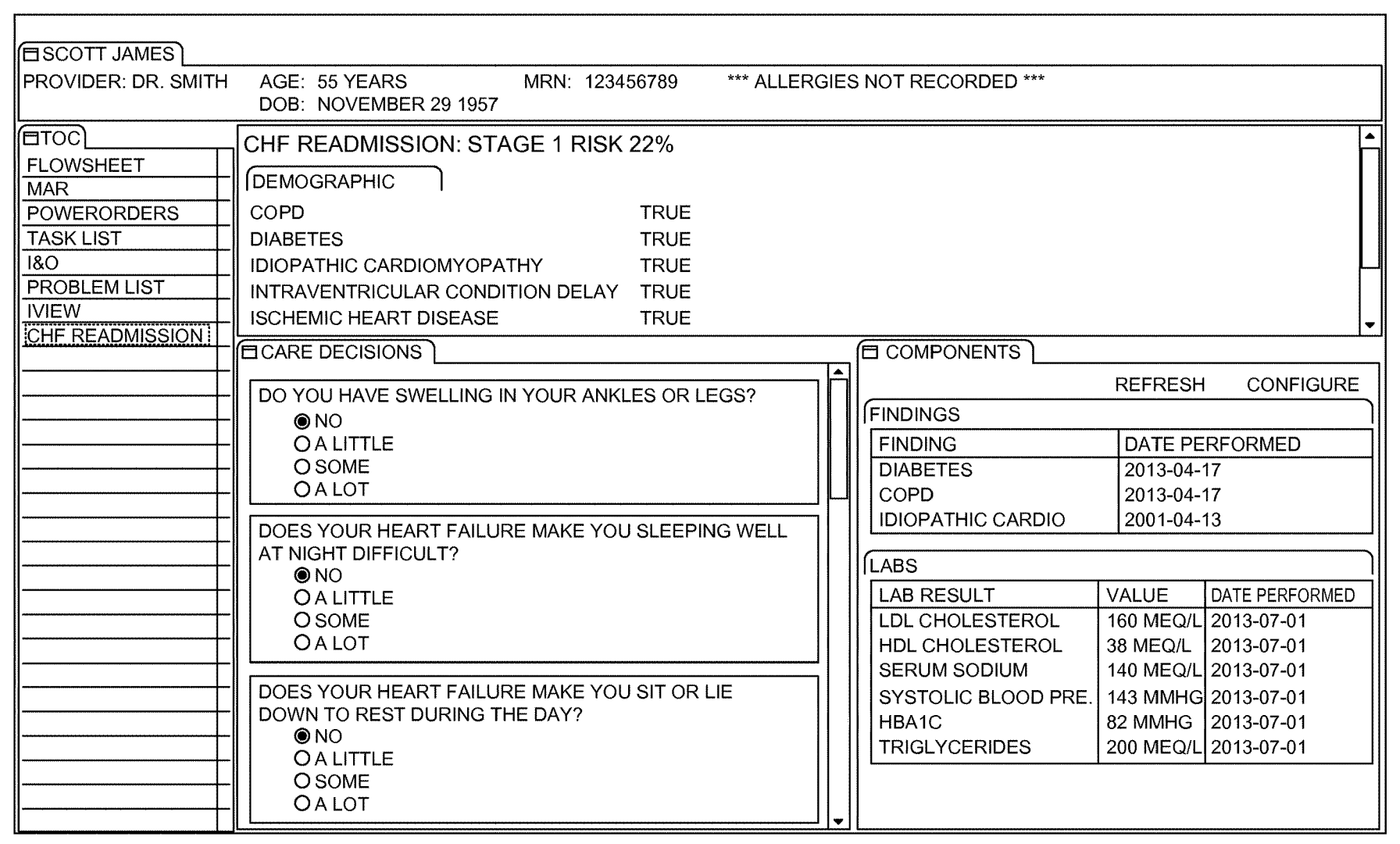
Figure 5F:

Turning now to FIGS. 5A through 5F, a series of screen displays are provided showing example graphical user interfaces for a decision support application in accordance with embodiments of the present invention. With reference to FIG. 5A, a first screen display 5000 is provided showing example graphical user interface 5142. In some embodiments, interface 5142 operates on a client device or client location, such as at a point-of-care. In some embodiments user interface 5142 comprises provider/clinician interface 142 of FIG. 1A. In some embodiments, interface 5142 comprises an interface for Cerner PowerChart or an electronic patient chart application interface.

Interface 5142 includes a patient component or tab 5005, for presenting information about a patient. Interface 5142 further includes a dynamic menu or table of contents 5010 of conditions for the patient, including at-risk conditions and decision support events. For example, here one of the conditions, indicated as item 5012 in TOC 5010, includes a risk for CHF Readmission. Interface 5142 includes an area for presenting a condition risk score 5020 associated with a condition selected from TOC 5010. Additionally, interface 5142 includes an area for presenting risk factors 5030 associated with the selected condition and used by a condition program, agent, or routine, for determining the patient's risk for having or developing the condition (e.g., the risk score). As described above in connection to FIG. 3C, in some embodiments an updated condition program may be "pushed out" to or dynamically updated on clients running the decision support application. Thus, the condition items listed in TOC 5010, the risk score 5020, and risk factors 5030 may vary dynamically or change in near-real time, in some embodiments.

Interface 5142 further includes caregiver-role indicator 5060, which indicates a role of the caregiver-user. In this example, the role indicates cardiology. The role indicator 5060 may provide information to a caregiver about the flexing (or tailoring) of the particular chart (or set of patient information) being presented, since some embodiments flex the information based on the role.

Interface 5142 further includes an area for displaying components 5040, which include clinical information element(s) such as lab results, findings, tests, studies, or other elements of clinical information. In some embodiments, the components or clinical information elements may be expressed as one or more clinical concept(s). As described previously, embodiments of decision support services determine which patient data to present based on a treatment-session context such as role, venue, condition, or other attributes, such as user-caregiver preferences. Accordingly, some embodiments of components area 5040 of interface 5142 present clinical information elements in a timely, contextual manner. In some embodiments, display component 5040 are made contextually aware through software agents or routines, thereby allowing the relevant labs, findings, medications, and procedures are presented to the caregiver flexed to caregiver's specialty, role (e.g., cardiology), venue, condition (e.g. diabetes), and other attributes powered solver agent(s) and facilitated via healthcare agents continually learning. For example, as described previously a cardiologist treating a heart-attack victim in an ER may be shown a particular type of patient information such as patient vitals, medications, and previous heart condition diagnoses; while an endocrinologist treating a diabetic patient at a research hospital may be shown clinical studies in which the patient is enrolled and patient compliance with prescribed condition management regimens.

In some embodiments, the determination of which clinical information elements or component to present is determined through the ontology framework described in connection to FIG. 3A.

Interface 5142 also includes assessment area 5050, which is further described in connection to FIGS. 5B and 5E. In some embodiments, assessment area presents the dynamically generated questionnaire described previously.

With continuing reference to FIG. 5A and reference to screen displays of 5B-5F, an example user session is described. In some embodiments, upon accessing a patient chart, the decision support application communicates with decision support software services such as agent/solver services 126 of FIG. 1A or cloud-based (or distributed) services and determines whether there are any new risks to manage. For example, as shown in the screen display of FIG. 5C, a highlighted (darkened) menu item in the conditions TOC on the left indicates that the patient is at risk for diabetes. As previously described, in some embodiments there are also other options for getting the caregiver's attention, such as direct messaging to the caregiver's inbox, SMS, or an icon on the task bar.

Continue with the example, upon the user selecting a particular at-risk condition, interface 5142 presents supporting details, including a risk score 5020 and the risk factors 5030 that contributed to the score. In some embodiments, this score can be calibrated based on the user-caregiver's own health system's historical activity and can be categorized into high, medium, or low risk level. In addition to this score and related factors, some embodiments display the clinical components 5040 that are relevant to the risk, role, and venue, using a list of meaningful concepts it built for this risk, which may be specified in a corresponding condition program, in some embodiments. In this example screen display of FIG. 5C, the presented components 5040 include related labs and meds. In some embodiments, these components and clinical factors within each component are further customizable based on user preferences, the provider, role, or specific need.

Continuing the example user session, a user-caregiver can access another patient's chart, such as the chart for patient Scott Myron shown in the example screen display of FIG. 5D. The screen display of FIG. 5D further illustrates how the decision support application flexes to present contextual, timely, and relevant, and other desired information to the caregiver. Upon opening the next patient's (Scott Myron's) chart, the application again uses the caregiver's role and venue and the patient's or person's information (such as patient information 2110 described in FIG. 1C) to see if there are new risks. (As described previously, the patient information may include local patient records, patient health records in the cloud, or distributed across multiple locations.) In the example screen display of FIG. 5D, the decision support application interface presents information indicating that the particular patient has a high risk of readmission for congestive heart failure. The corresponding CHF Readmission risk score and risk factors that contributed to this score are also presented. In this example embodiment, the relevant clinical findings and labs to present to the caregiver are dynamically and contextually determined.

Continuing the example, with reference to FIGS. 5D and 5E, in some embodiments, if the decision support application concludes that additional details might help complete the picture needed to provide appropriate care, it may provide the user-caregiver me a helpful questionnaire or assessment, as described previously. (In some embodiments, missing patient information might be imputed, as described previously.) In some embodiments, where a question answer already exists in the patient's record, it's pre-populated.

In this example user session, a user-caregiver indicates that the patient has some trouble sleeping (shown in box 2). In response, the application adds anxiety and depression as potential conditions to a problem list. In some embodiments, the question and answer pair are associated with an appropriate industry terminology standard, such as standard clinical concepts, which facilitates additional decision support-related actions, measurements or events to be triggered, in some cases dynamically and automatically. Upon submitting the answers (shown in box 4), an embodiment of the system sends notifications to appropriate clinicians and associated roles so they can continue care. For example, if based on information determined by the assessment or questionnaire, the application determines that the patient might have a risk for diabetes, then a notification may be provided to an endocrinologist and the patient's primary physician. In one embodiment, the endocrinologist receives an email, instant message, or notification with a link that enables the endocrinologist to access the particular patient's chart (such as presented in the example screen displays of FIGS. 5A-5F) by clicking on the link. In some embodiments, the particular chart presented to the endocrinologist is flexed based on the condition, venue, and specialty or role (endocrinology) as described previously. The endocrinologist and also the patient's primary physician represent caregiver-users with different roles, in the role-venue-condition context, and thus may be provided with a user interface that is flexed or tailored to their specialty, as described previously. In this manner, embodiments of the invention streamline patient care and reduce confusion or loss of knowledge during a patient handoff, as each caregiver is presented a view that is tailored or flexed to their role. Examples of caregiver roles are illustratively provided in FIG. 5F.

With reference to FIG. 5A, in some embodiments, the particular risk factors 5030 (which may be conditions) may be determined for a patient, based on a condition/event program, which may be selected, modified, or built, as described above. In some embodiments, the risk factors specify a clinical variable and clinical value, for example age (clinical variable) under one years (clinical value) might be a risk factor for a particular condition. In some embodiments, a risk factor is determined as positive or negative for a patient from a previous diagnoses indicated by the patient health record. For example, risk factors 5030 include kidney disease, which may have been diagnosed. In some embodiments, the risk factor determination is facilitated by an assessment, which may be presented in area 5050. In some embodiments determining whether a patient has risk factors is handled by the condition program, a subroutine, or handed off to a dedicated agent, and may include input from a caregiver(s) or soliciting input from one or more caregivers. In some embodiments, agent(s) or condition programs, or a caregiver may determine whether a patient has a given risk factor based on the patient's EHR (such as the presence of an ICD9 code for diabetes indicates that the patient probably has diabetes, where diabetes is a risk factor), based on pattern(s) in the patient's health record matching criteria indicating a likelihood for the risk factor or based on the clinical values of certain clinical variables present in the patient health record. For example, where diabetes is a risk factor, the risk factor may be identified in a particular patient, such as "gestational diabetes" for a pregnant patient having clinical variables indicating pregnancy and unstable blood glucose levels. In some embodiments, dedicated agents including healthcare agents or solver agents may be used to determine whether the patient has a particular risk factor.

In some embodiments, where particular patient information is missing, such as a risk factor or clinical variables used for determining a risk factor, the values may be imputed from the values occurring in records of similar patients, from consumable content 3170, as described previously. In some embodiments, the missing information prompts a dynamic assessment such as the questionnaire presented in area 5050.

In some embodiments the dynamic assessment takes the form of a questionnaire, but may also take the form of prompts to appropriate caregiver or the patient to provide needed information, or scheduling of or requests for tests, visits, orders, or other actions to facilitate obtaining the information. In some embodiments, the appropriate caregiver receives an email or notice soliciting the desired information or requesting a patient consultation to determine (and provide) the desired information. In some embodiments, a patient may have sufficient information for determining risk, but additional information is solicited or determined so as to facilitate making finer, more targeted decisions.

In some embodiments the assessment is contextual based on the role (or "actor type) of the caregiver. For example, in embodiments of a questionnaire, the specific questions provided when the caregiver is a cardiologist may be different than when the caregiver is an endocrinologist, a psychologist, nurse, or a social worker. Accordingly, in some embodiments the assessment also flexes based on the role, venue, and condition. In some embodiments, the assessment uses a model similar to the SCORM (shareable content object reference model) model used by the military, which includes contingent scripts, interactive dialogs or scropt components, and may be driven off of tables for questions. In some embodiments the questions are handled by agents, which may utilize solvers from solver library 2122, such as finite state machines or fuzzy logic for determining assessment questions and question orders.

In some embodiments specific questions or solicited information is based on known questionnaires or assessments used in health care, such as the University of Minnesota. In some embodiments, the questions are based on machine learning, such as learned related concepts from mapping service 3100, or from learned assessments or questions provided by other caregiver treating patients having similar condition(s) and related concepts. (For example, other patients of the same demographic as a target patient and also having condition X, as the target patient may have, typically have symptom Y. Does the target patient have symptom Y?)

Questions can also come from a tables or databases and use branch logic; for example, if caregiver is X and patient has Y, then ask Z. Similarly, some embodiments of the assessment ask specific additional questions based on the answers to previous questions. In some embodiments an agent assembles a questionnaire.

In some embodiments, as described above, question-answer pairs are codified as concepts of a clinical nomenclature. For example, as shown in FIG. 5B, the answer to the question regarding swelling in legs or ankles, the pair "some" and "swelling in ankles or legs" can be codified. In this manner, the answers can me inputted back into mapped health information (that is, the newly provided data is "structured" and ready for consumption). Similarly, the codified question-answers are machine-readable, interpretable, and actionable. For example, a particular condition program, such as the sepsis detection agent described previously, may be able to readily respond to the newly provided information because the newly provided information is machine accessible. In some embodiments, the information acquired by the assessment is fed into the condition program, which may result in revising a patient's determined risk score for conditions or decision support event(s). The information acquired by the assessment may also be fed into the ontology framework and concept mapping service described in connection to FIG. 3A, so that newly acquired information becomes part of the mapped content 2420 of heath information used to determine sets of concepts that are related to a target condition or concept, as described in connection to FIG. 3A. In some embodiments the questions are answered via radio buttons or check boxes or similar simple user-interface components, which can facilitate determining the codified concept for the question-answer pair. In some embodiments, the assessment application communicates with a backend service to determine the specific codes for the question answers.

In some embodiments, answers to questions result in specific recommendations, as shown in FIGS. 5B and 5E (boxes 2-4). Additional details describing recommendations provided in response to assessments and other embodiments of the present invention that determine a recommendation (including a care plan, further testing or diagnostics, treatment, dosage, or consultation, or other order or recommendation), such as a recommendation provided in response to a determined condition, determined possibility of a future condition, risk for a condition, are described in U.S. patent application Ser. No. 13/646,356, filed on Oct. 5, 2012, which is herein incorporated by reference in its entirety.

Figure 6A:
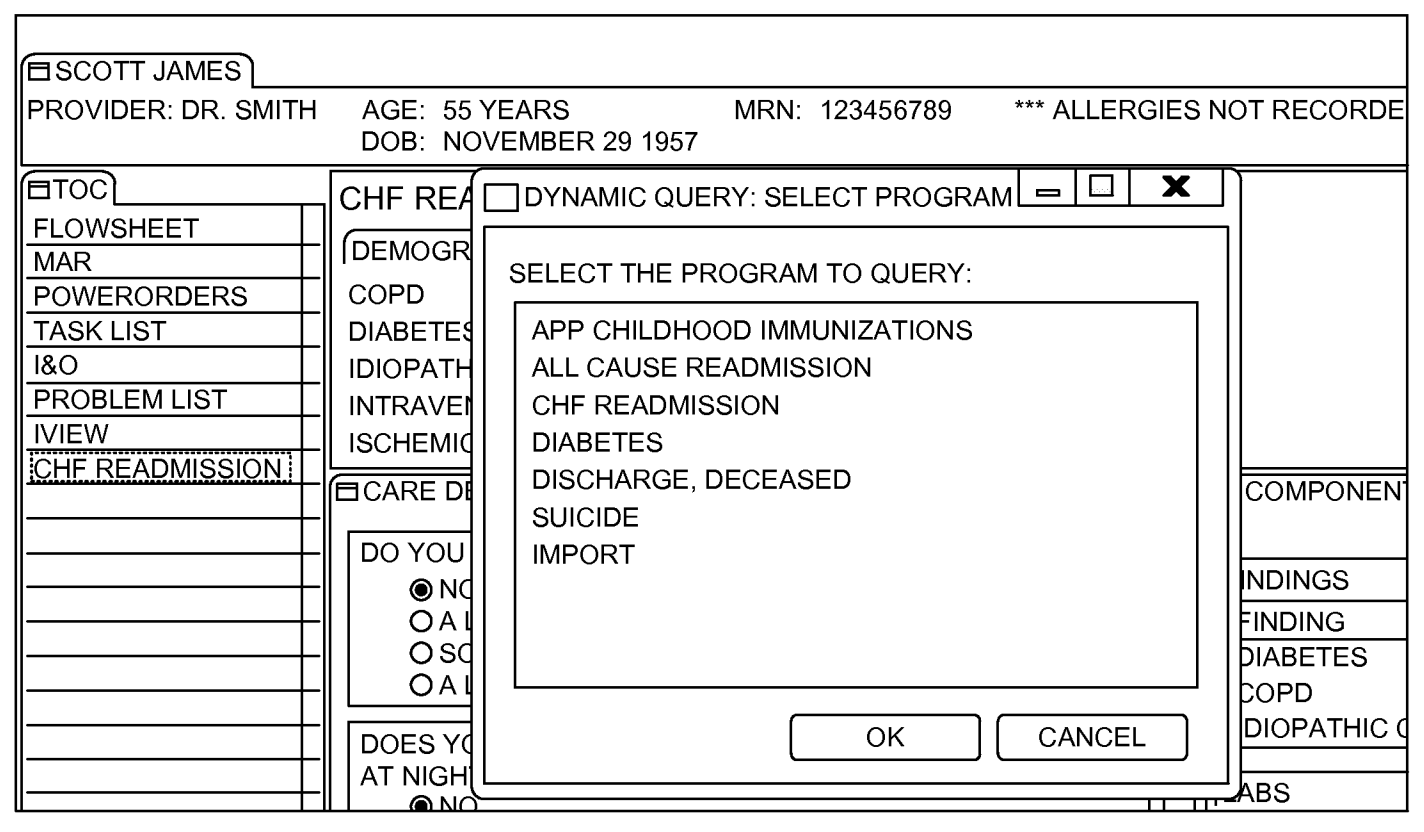
Figure 6B:
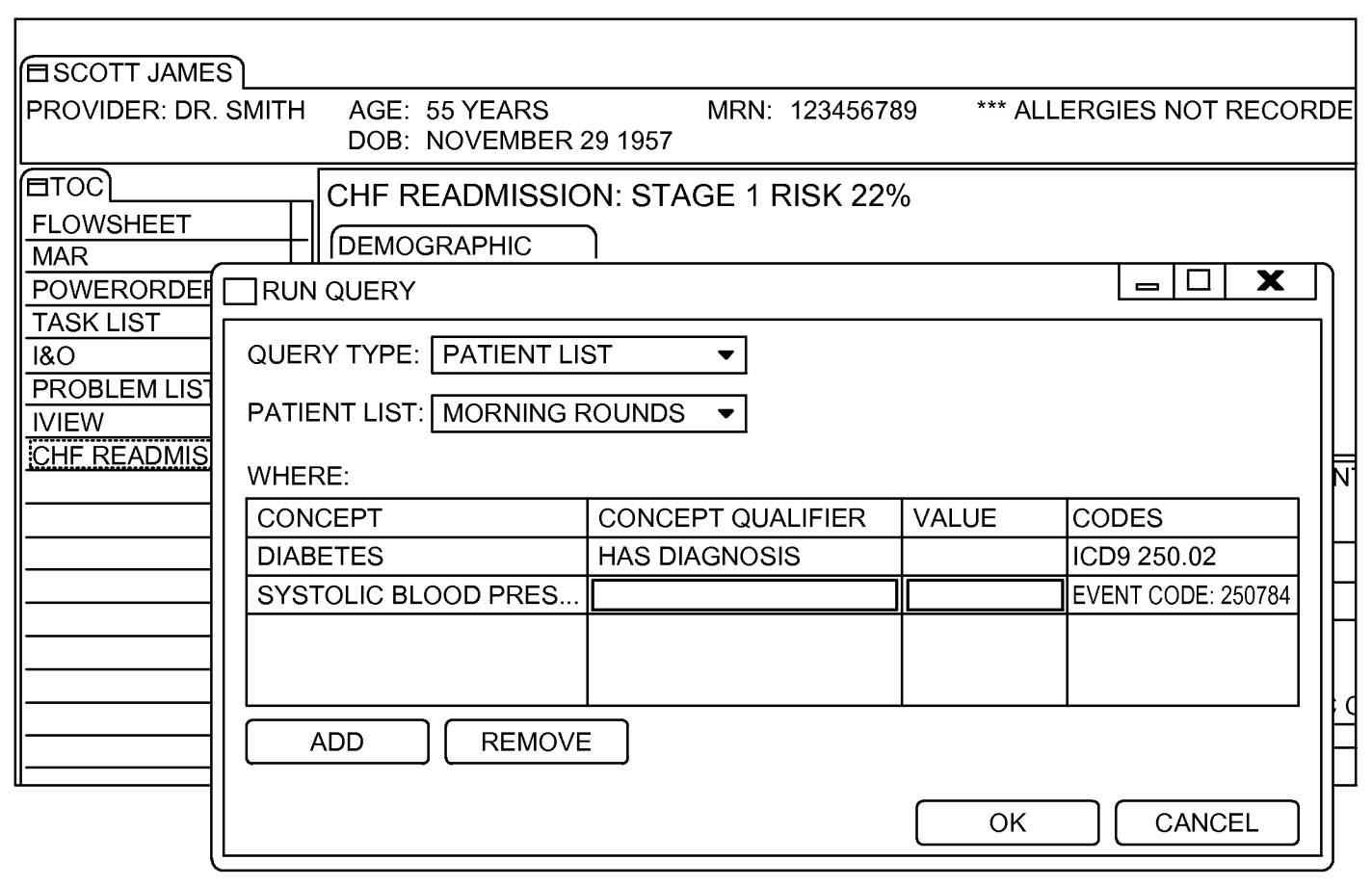
Figure 6C:
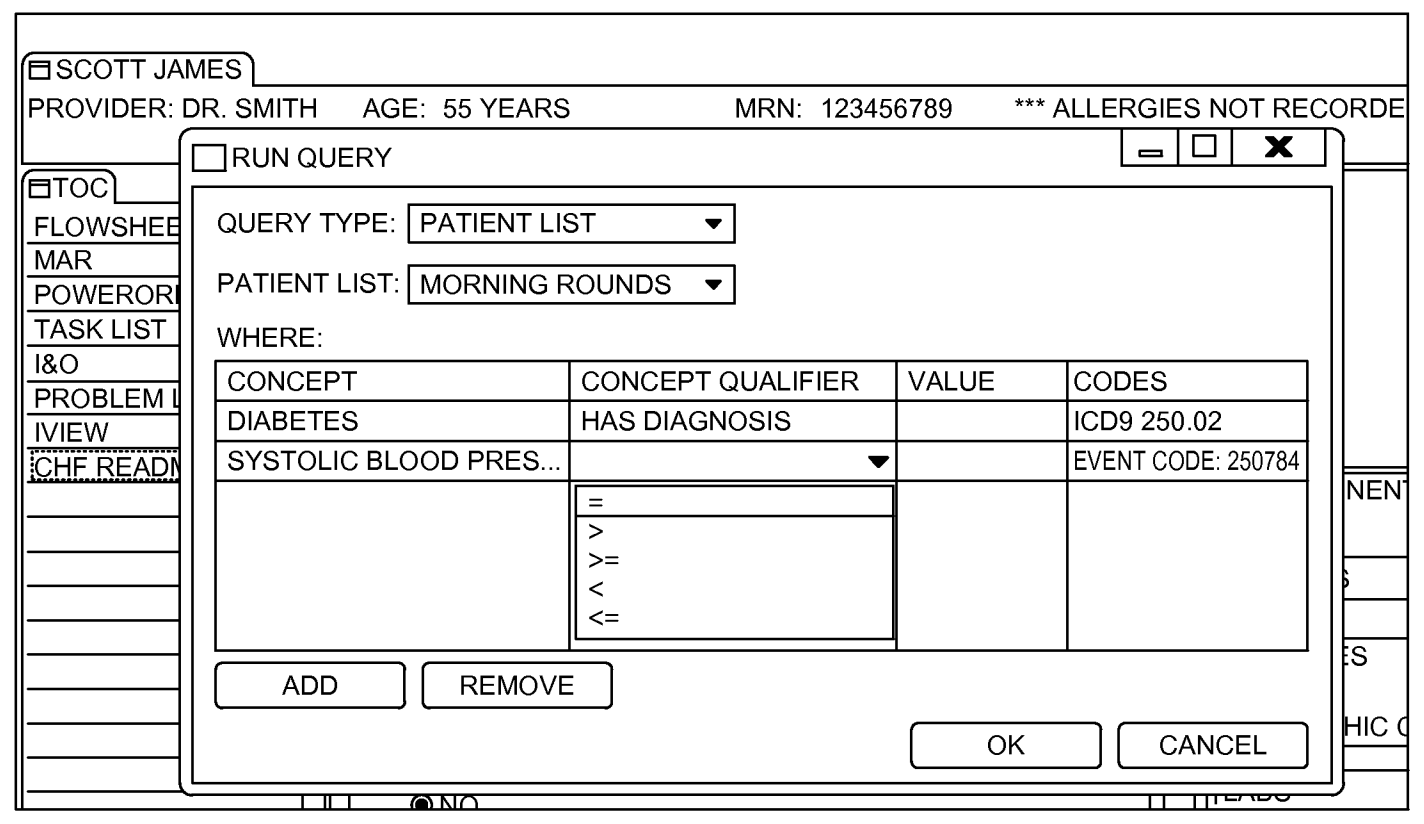
Figure 6E:
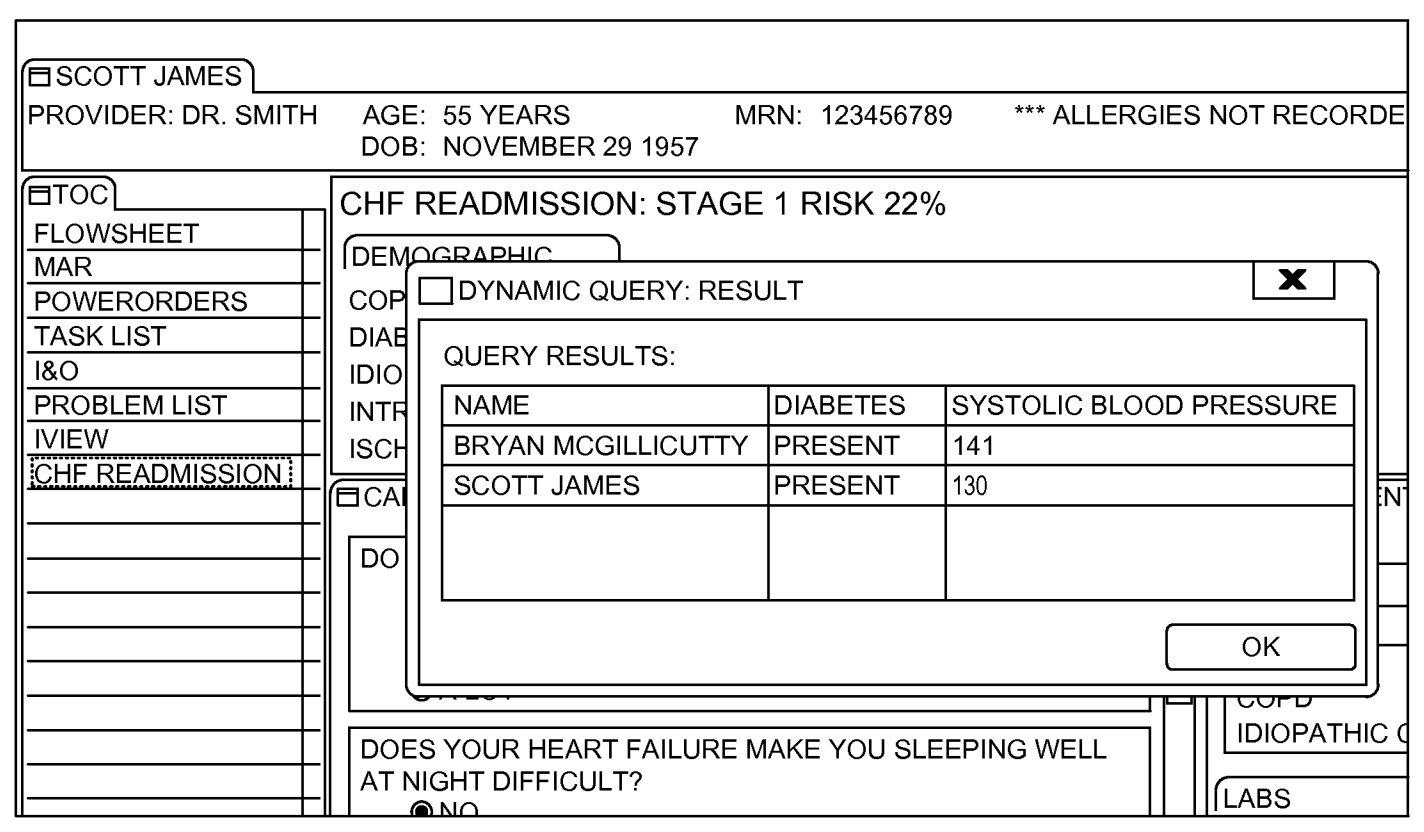

Turning now to FIGS. 6A-6G, a series of screen displays are provided showing aspects of query operations in accordance with embodiments of the present invention. Some embodiments of decision support application provide query services such as described in connection to FIG. 4C. In some embodiments, the ontology framework described in connection to FIG. 3A facilitates querying across mapped health care information or consumable content 3170. For example, with reference to FIG. 6A-6E, a user-caregiver is interested in finding how many of his or her patients have systolic blood pressure greater than 125 that are also diabetic within the scope of a potential CHF Readmission risk. The user-caregiver can access a dynamic query routine (FIG. 6A), (which may be embodied as a subroutine or separate application, and may be handled by an agent), as shown in FIG. 6A. Using the ontology created for CHF readmission, a local, or proprietary nomenclature, the user can specify the parameters (FIGS. 6B, 6C, and 6D) and receive the results (FIG. 6E) in near real-time. In some embodiments, the search parameters are provided in the local nomenclature and are first mapped to a standard nomenclature used by the pool of information being searched, such as the consumable content or health facts information. In these embodiments the search results are then mapped or translated back to the local (or proprietary) nomenclature and the results presented to the user in that local (or proprietary) nomenclature.

Figure 6G:
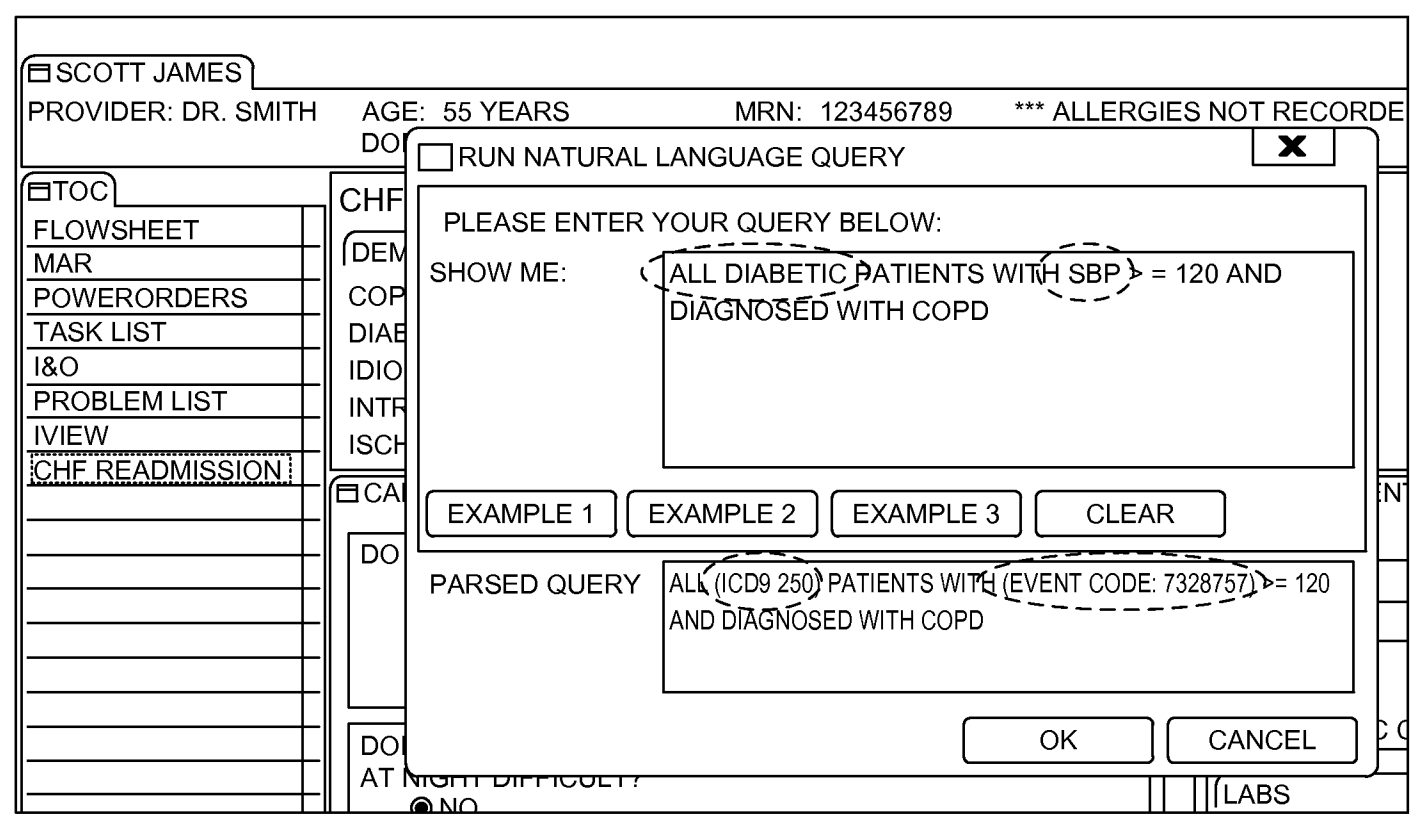

With reference to FIGS. 6F and 6G, an example query operation is illustratively provided. In this example, a natural language query is performed from a graphical user interface such as described in connection to FIG. 5A. In this example, a query is received (FIG. 6G) for "all diabetic patients with SBP >=120 and diagnosed with COPD." In an embodiment, the query is received via the graphical user interface by a caregiver. In an embodiment, the query is received by typing a query into the user interface, speaking the query, which may be converted to text, or selecting one or more clinical variables of the patient for which to query on. In an embodiment, a query is suggested to the caregiver based on the available clinical information for a patient such as clinical information elements or determined clinical conditions. In an embodiment, the received query is parsed into concept codes (such as shown in the lower window of FIG. 6G) wherein ICD9 250 corresponds to a concept code for diabetes, and the "event code: 7328757" represents systolic blood pressure. Accordingly, in one example embodiments for performing a query receive the query in an unstructured format, such as spoken natural language, then using a natural language processing service (such as described in connection to FIG. 4F) the query information is parsed and converted to clinical concept codes. A determination may be performed to identify the nomenclature of the query concept codes, and in an embodiment, the query concept codes are translated from a first nomenclature (for example, a proprietary nomenclature) to a second nomenclature or multiple nomenclatures (the nomenclatures of the data to be queried). The query is performed and the results are received. In an embodiment, the results are translated back into the first nomenclature and provided to the caregiver, such as via the user interface. Additional examples of querying operations are provided in connection to FIG. 4C.

Figure 7A:
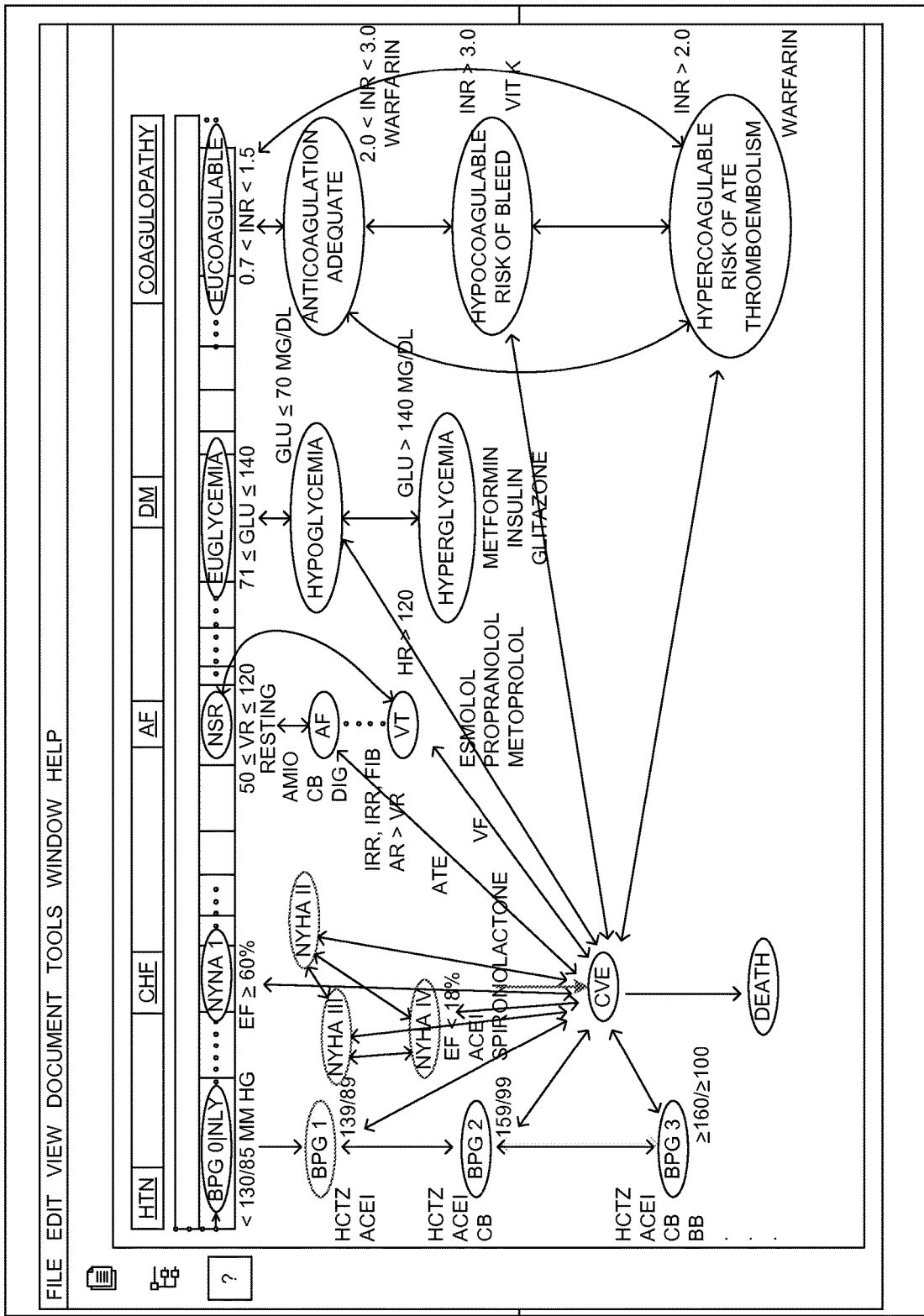
FIG. 7A illustratively depicts an example finite state machine solver specific to a patient and suitable for use to determine a condition or recommended treatment in accordance with embodiments of the present invention.
Figure 7B:
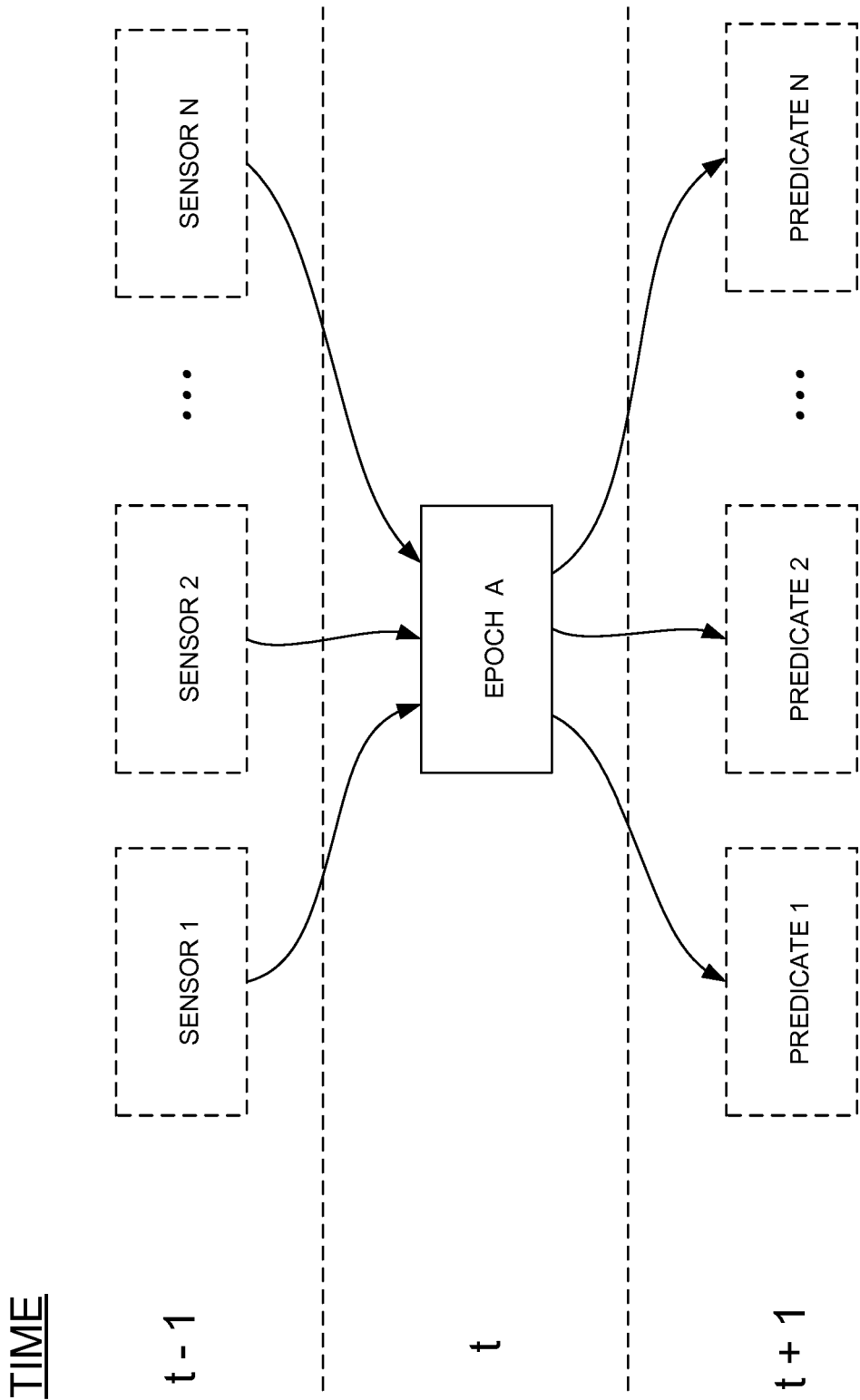
FIGS. 7B-7D illustratively depict past, present, and future potential patient states associated with clinical decisions for a patient.

With reference to FIG. 7A, an example finite state machine solver 700, is illustratively depicted, specific to a patient and suitable for use to determine a condition or recommended treatment in accordance with embodiments of the present invention. This example of an instantiated finite state machine solver is specific to a patient suffering from heart failure and other conditions. The finite state machine can be evaluated to determine the patient's specific condition and recommended treatment. In this example, content parameters, such as example content tables 2124, provide parameters specifying the transition conditions for each state of the finite state machine, while the discretized patient information, provides the states of the finite state machine. Accordingly, the states of the finite state machine correspond to conditions of the patient. Based on this, this finite state machine maybe traversed in order to determine the current state (i.e., condition, including epochs) of the patient. Based on determining the patient's state, an appropriate condition program can be selected or generated, in some embodiments via an agent. In an embodiment, each of the previous states associated with the patient comprises a sensor or preceptor that may determine the present state of the patient and each potential future state of the patient comprises an effector, such as discussed in connection to FIG. 1C.

In the example embodiment of FIG. 7A, each vertical column of the finite state machine corresponds to a different condition-type of the patient, and each state within each column corresponds to a specific condition. For example, one of the columns of the finite state machine corresponds to a DM (diabetes) condition-type. Within this column, three states are present: euglycemia, hypoglycemia, and hyperglycemia. Adjacent to each state are transition parameters specifying conditions necessary to transition to another state. For example, a patient will be in the Hyperglycemia state when the discretized patient information indicates that "GLU ≥140 mg/dL." In some instances, evaluating each state of the finite state machine may require invoking another solver, such as a mixed integer solver—a type of linear solver. The output of the evaluation of the finite state machine of FIG. 7A is a determined condition or recommended treatment for the patient, and may be used for determining or creating a condition program for the patient.

Figure 7C:
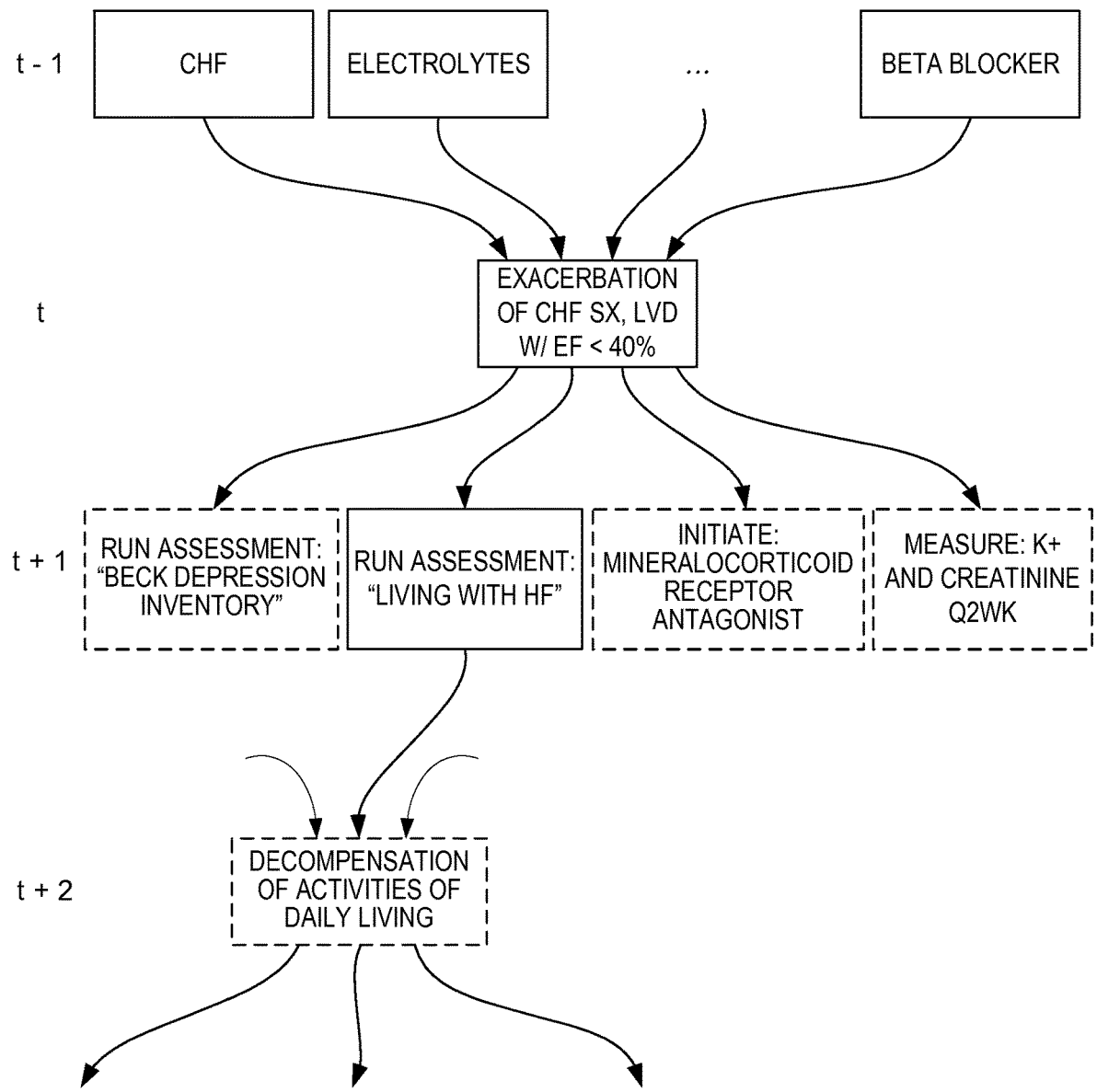
Figure 7D:
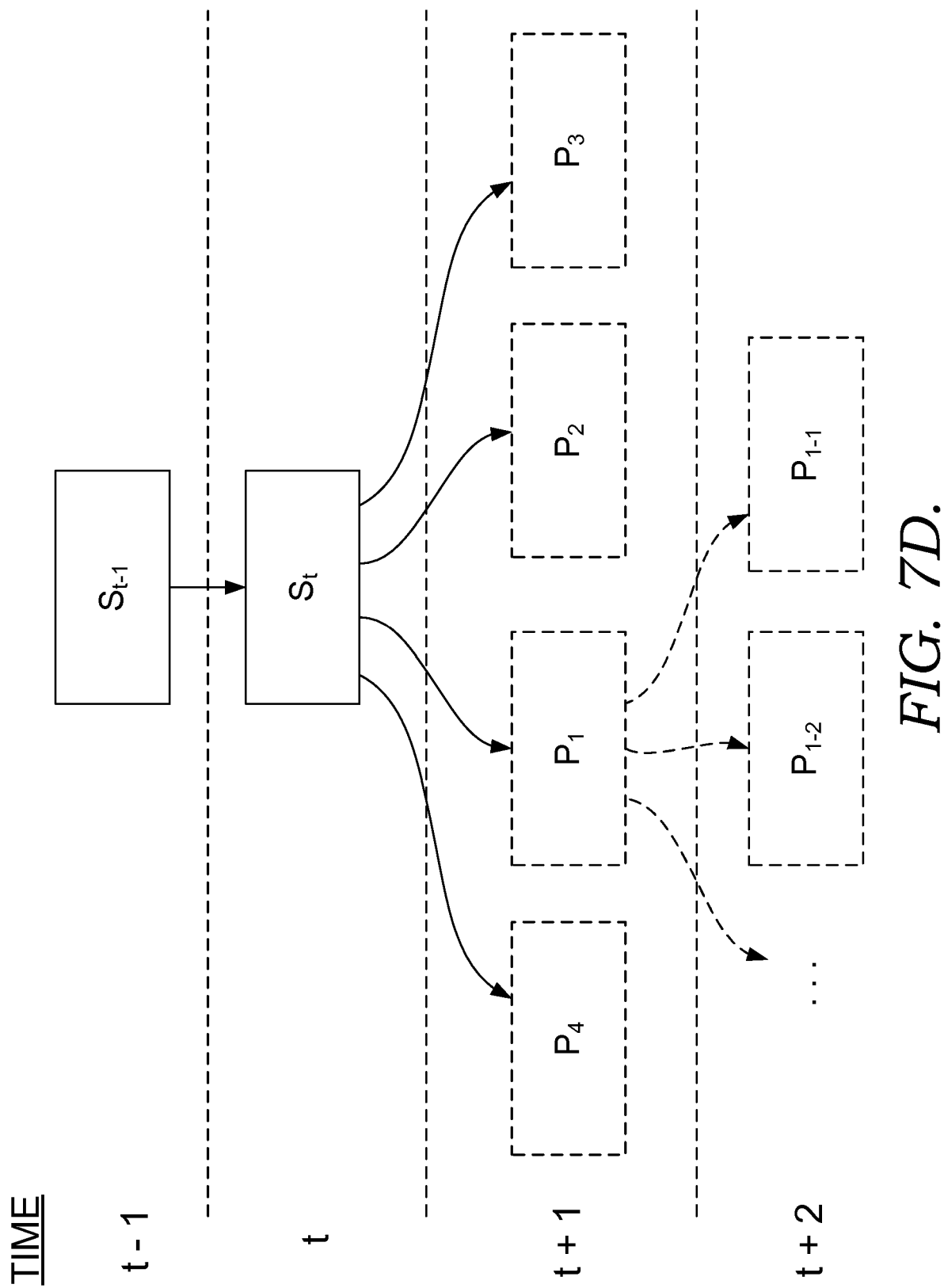

FIGS. 7B-7D illustratively depict past, present, and future potential patient states associated with clinical decisions for a patient. These depictions are intended to provide examples of patient event sequences, including past, current, and potential future decision support events, for determining next (or future decision support events associated with the patient. Additional details are provided in connection to FIGS. 4G-4I.

With reference to FIG. 7B, a set or vector of multivariable predicates whose truth-states are ascertained from information that is contained in the electronic health record is assembled at time t−1 and comprises a sensor pattern that denotes a compound or composite predicate that merits attention and decision-making. In an embodiment, the concurrent materialization of the predicate pattern vector causes a health care agent (such as a CareDecisions agent) or triggers a software service or process to nominate at least one specific CareDecision epoch A at time t and in an embodiment, enqueue it for a qualified user's review such as for likely decisions and action. Epoch A thus represents a critical juncture, in an embodiment.

In one embodiment, the epoch A is not a transient or momentary state; rather, it persists for a finite period that is commensurate with timeframes that are customary for ordinary, decision-making in health care services. Epochs are delimited in time by the onset of sensor predicate vector elements' values such that a distance for matching the vector against one or more of the set of reference epoch vectors is suitably small, and by the offset of vector elements' values such that the distance is larger than a threshold denoting a close or satisfactory match. In some embodiments, the offset may be due to the beneficial effect of a treatment or intervention that has been initiated. In some embodiments, the offset may be due to changes that arise spontaneously for the patient irrespective of any treatment or intervention, or the offset may be due to the emergence of a preponderance of multivocal and countervailing evidence from other sources as measured by cronbach alpha or other means such that one or more of the predicates that led initially to the epoch's being nominated is overruled. Epochs may be as short as several seconds or minutes in length in the case of critical care and perioperative care or may be as long as several years in the case of slowly-evolving chronic diseases. In an embodiment, care decision epochs are defined by parameters 2120 (discussed in connection to FIG. 1C), and may indicate the specific sensor information (such as clinical conditions (including sequences or patterns of clinical conditions) and clinical variables (including patient demographic variables, treatment history and caregiver/health care entity/insurance information) used to determine the decision epoch. It is contemplated that in some embodiments, decision epochs are discovered or "learned" by the mining and processing of patient information such as described in connection with FIG. 3A. For example, it may be determined that among groups of patients with common clinical information, certain sensors or patterns (including sequences) of sensors frequently lead to certain decisions points or decision patterns in patient treatment. Accordingly for a given patient having a set of sensors in common with other patients each of whom experienced a particular decision epoch, a probability can be determined that the particular decision epoch will apply to the given patient. Based on that probability, one or more recommendations may be determined for the patient, such as altering the course of care for the patient, consulting a clinical specialists, or other modification to treatment.

In an embodiment, the definition of a decision epoch contains the sensor information that led to the epoch's evocation. In an embodiment, it also contains a CareDecision epoch reference database predicate vector that the patient's information matched, and in an embodiment contains a Tanimoto or Jaccard or other distance metric denoting the degree of similarity or quality of matching of the patient's sensor vector to the reference vector associated with the nominated epoch. In an embodiment, it further contains the evidence-based content that is clinically indicated and recommended in the circumstance that obtains at time t, plus normative content that is data-mined and known to be reasonably prevalent and associated with desirable outcomes in that circumstance. In an embodiment, it simultaneously contains evidence-based content that is clinically contraindicated and either absolutely or relatively proscribed in the circumstance that obtains at time t, plus normative content that is data-mined and known to be reasonably prevalent and associated with undesirable outcomes in that circumstance, particularly with regard to interactions among therapeutics that may be utilized in other comorbid health conditions. In an embodiment, the normative and prescriptive content, in turn, may provoke obtaining additional information from the patient at t+1, which may include without limitation answers to a patient assessment, such as described in connection to FIG. 5E, a standardized questionnaire that is pertinent to the circumstance, observation of circumstance-relevant patient findings by physical examination, querying the patient (or family member or caregiver) for additional information, performing one or more diagnostic tests, initiating one or more therapeutic maneuvers or procedures or prescribed medications, or temporizing for a circumstance-relevant period of time, for example. In some embodiments, these items of information may be referenced in a further sensor pattern, which may optionally include one or more sensors that did not arise as a consequence of the prior decision epoch. In an embodiment, the information at time t+1 itself constitutes an induced or partially-induced set or vector of multivariable predicates that denotes yet another distinct circumstance that evokes a corresponding decision epoch.

Turning now to FIG. 7C and with reference to the example shown in FIG. 7A and the discussion of FIG. 7B, we have in FIG. 7C, an example circumstance where at time t−1 the congestive heart failure CHF sensor has caused ordering and measurement of left ventricular function and ejection fraction by ultrasound or other means and has determined that left ventricular dysfunction is presently moderate with an ejection fraction <40% and increased symptoms, including orthopnea and shortness of breath. In this example, serum electrolytes measured serially up to time t−1 show sodium trending downward over time. Beta-blocker and diuretics and other medications routinely prescribed in heart failure are ascertained to be at appropriate or near-maximal dosages in the context of progression to NYHA Class III severity. The vector of the patient's sensor predicate values prevailing at time t is matched against a set of decision epochs, which in one embodiment include predefined decision epochs (including learned decision epochs). In one embodiment, a vector of the sensor predicate values is determined by Tanimoto or Jaccard or similar metric to be a close match, resulting in the nomination of the 'Exacerbation of CHF with LVD and EF <40%' epoch. In this example, this epoch is, in turn, associated with evoking evidence-based and data-mined normative prescriptive content at time t+1—including running 'Beck Depression Inventory' (BDI) and 'Minnesota Living with Heart Failure' (MLWHF) assessments (or re-running them, in the case that they have been completed on a previous date more remote than 14 days before the current date); ordering a mineralocorticoid receptor antagonist medication, such as spironolactone; and ordering a recurring, periodic measurement of serum potassium and serum creatinine, to monitor and guard against the risks of hyperkalemia and renal injury, respectively, which may be associated with mineralocorticoid medications. The information collected by running the MLWHF at time t+1 may determine that the patient's Activities of Daily Living (ADLs) are significantly impaired, leading to the nomination of the 'Decompensation of ADL' CareDecision epoch at time t+2. This, in turn, may, with other sensors, cause the evocation of evidence-based or data-mined normative prescriptive content at time t+3, such as performing the 'Physical Self-Maintenance Scale' (PSMS) or other comparable assessment, to further characterize and quantify the extent of impairment of ADLs. It may also cause the initiation of physiotherapy, occupational therapy, social work or case manager engagement, revision of dietary orders, or further review and adjustment of pharmaceutical regimen.

As contrasted with static, standardized clinical pathways or protocols, the timing of the materialization of the epochs and the data-mined normative content have a saliency that reflects frequent relevant itemsets that are prevalent in the mined historical records of similar patients including recent patients. Rather than exalting the simplistic insights that are represented in a pathway, the effect is to reveal those decisions and alternative actions that are relevant to "patients like this, at moments like the present one", which has the effect of promoting optimal timing and intensity and duration of intervention, such as in this example of heart failure management programs with near-optimal targeting.

FIG. 7D shows a diagram similar to FIGS. 7B and 7C. In the example illustratively provided in FIG. 7D, at time t a patient is in a particular state or condition (here, also a decision epoch) $S_t$, having arrived at $S_t$ from a previous state $S_{t-1}$. FIG. 7D shows that at time t+1, at least four possible states are available, with the likelihood probability that the patient will transition to a particular state at time t+1, given as $P_4$, $P_1$, $P_2$, and $P_3$. In an embodiment, this likelihood or probability is determined based on the comparison of similar patients, such as described in FIG. 7B. FIG. 7D also shows that if the patient transitions to state 1 (which has a probability of $P_1$), then at time t+2, the likelihood that the patient will transition to each of the states shown at time t+2, is given as $P_{1-2}$, and $P_{1-1}$. Thus the probability may also be determined not only for the next state (or condition, including the evocation of decision epochs) at time t+1, but also for future states at time t+2, t+3, etc. for the patient.

Figure 8A:
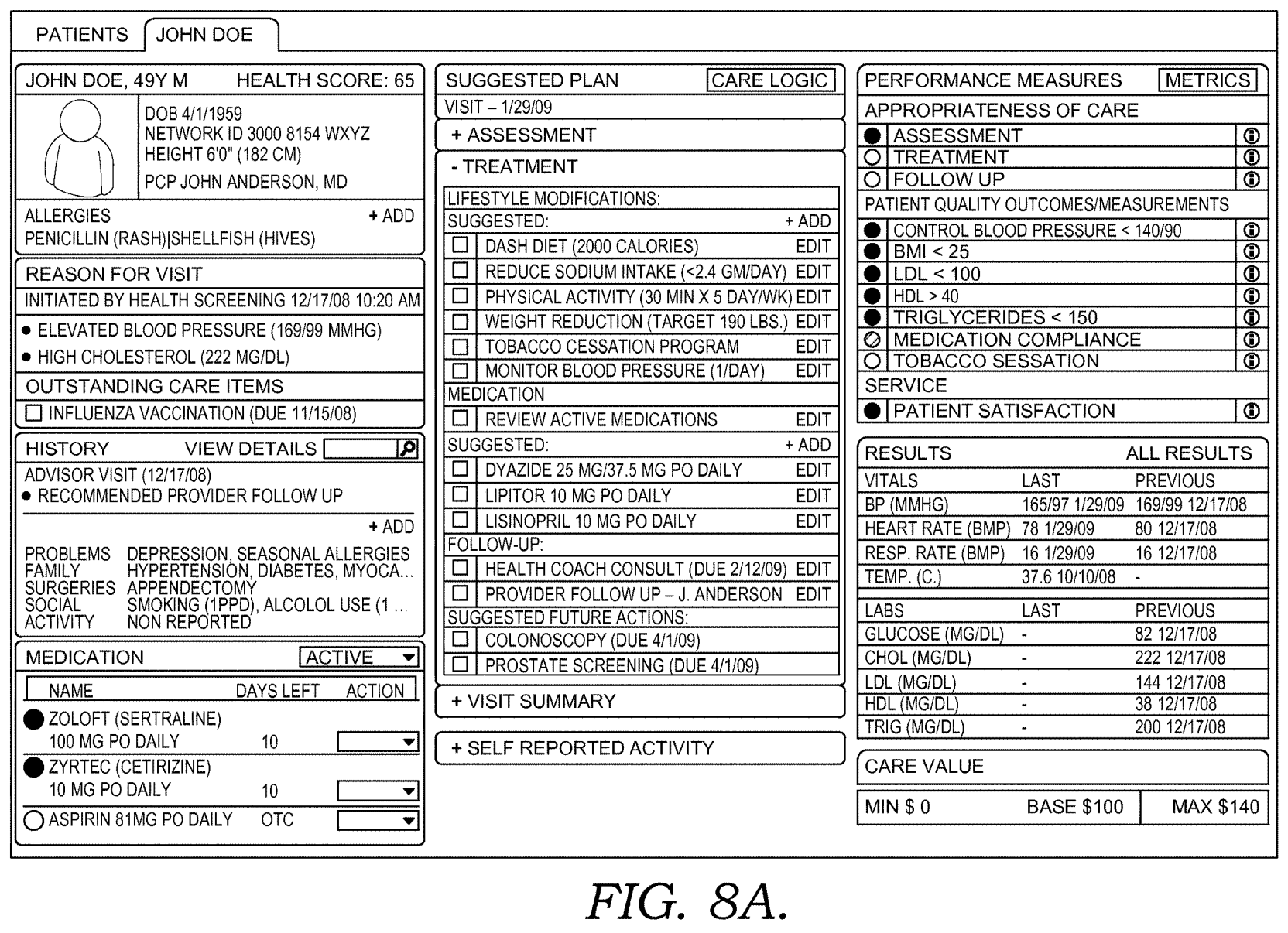
Figure 8B:
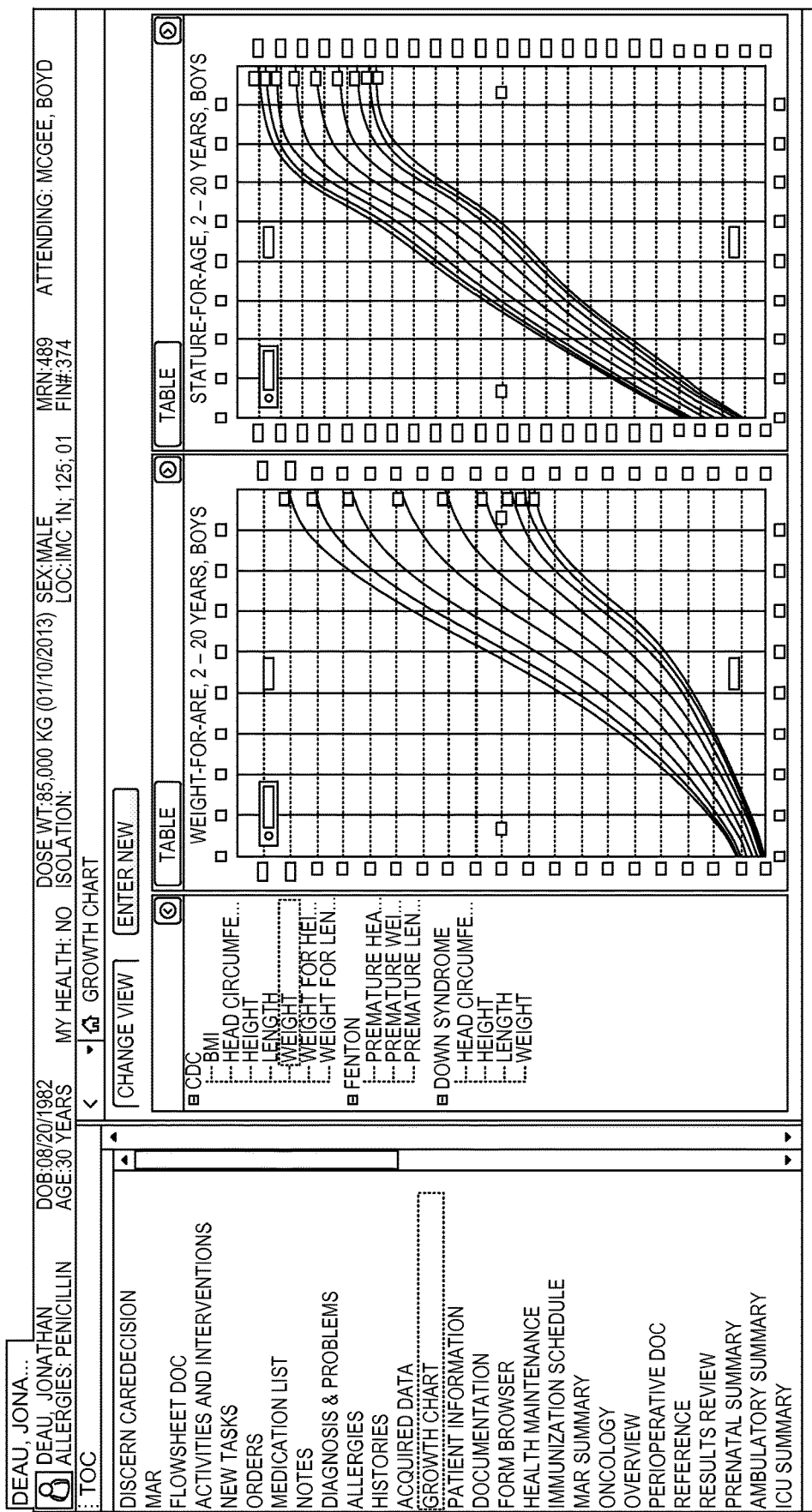
Figure 8D:
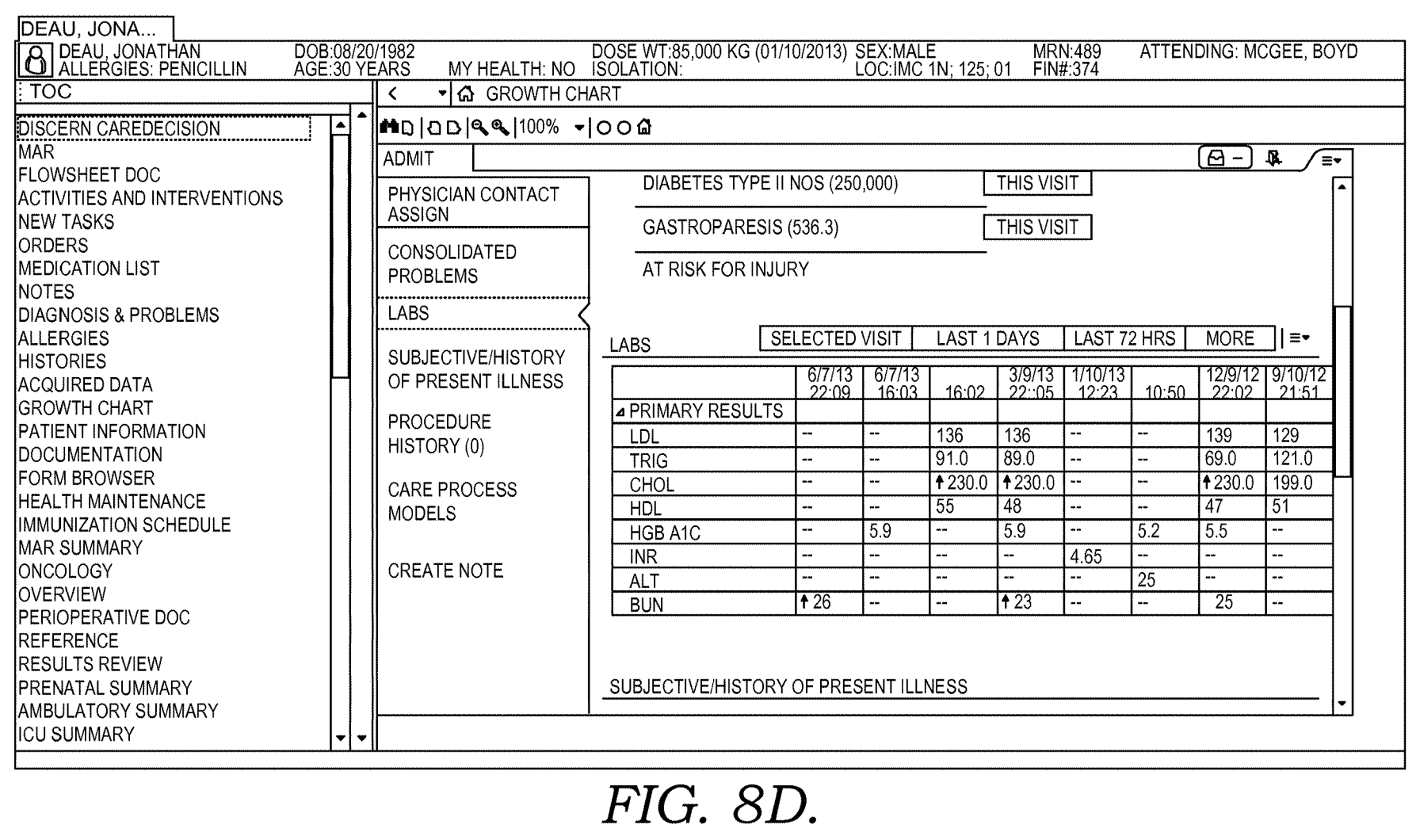

FIG. 8A-8D depicts illustrative screen displays of an example user interface for presenting and receiving clinical patient information in accordance with embodiments of the present invention. FIG. 8B shows an example of providing a user with additional information by selecting an item in the TOC (here "growth chart") for the patient, in comparison to other patients. FIG. 8C presents an example of a decision support application built using the EndPage framework within Cerner PowerChart®.

Additional example embodiments of the invention include: a system, method, and computer readable media having computer-executable instructions embodied thereon that when executed, facilitate a method for providing clinical decision support, the method comprising: receiving patient health data from a healthcare entity, the patient health data including a set of clinical concepts encoded in a first nomenclature; determining a second nomenclature corresponding to the first nomenclature; accessing a mapping database of mappings between the first nomenclature and the second nomenclature; from the first set of clinical concepts, determining a corresponding second set of clinical concepts encoded in the second nomenclature; accessing a first clinical condition program which uses a subset of the clinical concepts in the second set of clinical concepts to determine a probability that the patient has a first clinical condition; based on the first clinical condition program, determining that a patient has a probability for the first clinical condition; from the mapping database, determining a set of first-condition information including clinical concepts encoded in the first nomenclature and representing the first clinical condition, the determined probability that the patient has the first clinical condition, and the subset of clinical concepts used by the first condition program; and providing the first-condition information to the health care entity.

Some embodiments of the system, method, and computer readable media described above further comprise presenting in a user interface, a menu including the first clinical condition; and responsive to selecting the first clinical condition, presenting: (a) a condition risk score representing the determined probability that the patient has for the first clinical condition; (b) a set of risk factors corresponding to the subset of clinical concepts used by the first condition program; and (c) for at least a portion of the risk factors, a clinical value for the factor, the value determined based on information derived from the patient. In an embodiment of the systems, methods, and computer-readable media, described herein, the first clinical condition program is implemented by one or more software agents. In an embodiment, accessing a mapping database is facilitated by one or more software agents. In an embodiment, at least one of the presented menu, the presented condition risk score, or the set of risk factors are dynamically responsive to changes in the first clinical condition program. In an embodiment, clinical concepts comprise lab results, test results, patient conditions, patient health history, patient demographic information, or other discretized health-related information. In an embodiment, the clinical condition includes one or more of a disease, diagnoses, medical issue, or medical event; the probability for the first clinical condition is a calculated probability that the patient has or will develop the first clinical condition based on at least a portion of the set of clinical concepts for the patient; risk factors comprise one or more clinical variables of health data from population of patients that are determined to contribute to the likelihood that a given patient has or will develop the first clinical condition; the clinical variables correspond to clinical concepts; a clinical value comprises a patient-specific value corresponding to a clinical variable; the patient health information comprises specific lab results, tests, health-related findings, patient conditions, patient history, or other clinical-information component of a patient's health data; and/or the presented condition risk score and set of risk factors are dynamically responsive to changes in the first clinical condition program.

Some embodiments of the system, method, and computer readable media described herein further comprise presenting a condition assessment area for presenting a contextually-driven assessment based on patient information relevant to diagnosing or treating the condition, and for receiving patient information in response to presenting the assessment, wherein the received information includes one or more clinical concepts encoded in the first clinical nomenclature. Some embodiments of the system, method, and computer readable media described herein further comprise presenting a condition assessment area for presenting a contextually-driven assessment based on patient information relevant to diagnosing or treating the condition and determining that patient information is absent or stale in the patient health data.

In one aspect of the embodiments described herein, a system, method, or computer-readable media having computer-executable instructions embodied thereon that when executed, is provided for facilitate a method for providing clinical decision support comprising: receiving a first set of information about a patient, the first set of information including one or more clinical concepts encoded in a first nomenclature; determining a second nomenclature corresponding to the first nomenclature; accessing a mapping database of mappings between the first nomenclature and the second nomenclature; translating at least a portion of the one or more clinical concepts encoded in the first nomenclature into the second nomenclature thereby creating a second set of information about the patient including one or more clinical concepts encoded in the second nomenclature; accessing a library of clinical condition programs, each clinical condition program associated with a set of clinical concept risk factors encoded in the second nomenclature; determining one or more clinical conditions associated with the patient based on the second set of patient information and based on at least one of the clinical condition programs; translating into the first nomenclature the determined one or more clinical conditions and set of risk factors associated with the condition program corresponding to each of the one or more clinical conditions; presenting a user interface including a menu of condition items, each condition item corresponding to the determined one or more clinical conditions, wherein the conditions are presented using the first nomenclature; and responsive to selecting an item in the menu, displaying a risk score for the patient having the condition corresponding to the item, and displaying a set of risk factors relevant to the risk score, wherein the risk factors are presented in the first nomenclature. In an embodiment of the systems, methods, and computer-readable media, described herein, mapping entries of the mapping database are determined by one or more software agents.

In one aspect of the embodiments described herein, there is provided a system, method, or computer-readable media having computer-executable instructions embodied thereon that when executed, facilitate a method for providing clinical decision support, the method comprising: receiving patient health data from a healthcare entity, the patient health data including a set of clinical concepts encoded in a first nomenclature; determining a second nomenclature corresponding to the first nomenclature; accessing a mapping database of mappings between the first nomenclature and the second nomenclature; from the first set of clinical concepts, determining a corresponding second set of clinical concepts encoded in the second nomenclature; accessing a first clinical condition program which uses a subset of the clinical concepts in the second set of clinical concepts to determine a probability that the patient has a first clinical condition; based on the first clinical condition program, determining that a patient has a probability for the first clinical condition; from the mapping database, determining a set of first-condition information including clinical concepts encoded in the first nomenclature and representing the first clinical condition, the determined probability that the patient has the first clinical condition, and the subset of clinical concepts used by the first condition program; and providing the first-condition information to the health care entity.

Some embodiments described herein further comprise presenting in a user interface, a menu including the first clinical condition; and responsive to selecting the first clinical condition, presenting: (a) a condition risk score representing the determined probability that the patient has for the first clinical condition; (b) a set of risk factors corresponding to the subset of clinical concepts used by the first condition program; and (c) for at least a portion of the risk factors, a clinical value for the factor, the value determined based on information derived from the patient.

In an embodiment of the systems, methods, and computer-readable media, described herein, the first clinical condition program is implemented by one or more software agents; accessing a mapping database is facilitated by one or more software agents; at least one of the presented menu, the presented condition risk score, or the set of risk factors are dynamically responsive to changes in the first clinical condition program; clinical concepts comprise lab results, test results, patient conditions, patient health history, patient demographic information, or other discretized health-related information; the clinical condition includes one or more of a disease, diagnoses, medical issue, or medical event; the probability for the first clinical condition is a calculated probability that the patient has or will develop the first clinical condition based on at least a portion of the set of clinical concepts for the patient; risk factors comprise one or more clinical variables of health data from population of patients that are determined to contribute to the likelihood that a given patient has or will develop the first clinical condition; the clinical variables correspond to clinical concepts; a clinical value comprises a patient-specific value corresponding to a clinical variable; the patient health information comprises specific lab results, tests, health-related findings, patient conditions, patient history, or other clinical-information component of a patient's health data; and/or the presented condition risk score and set of risk factors are dynamically responsive to changes in the first clinical condition program.

Some embodiments described herein further comprise presenting a condition assessment area for presenting a contextually-driven assessment based on patient information relevant to diagnosing or treating the condition, and for receiving patient information in response to presenting the assessment, wherein the received information includes one or more clinical concepts encoded in the first clinical nomenclature. Some embodiments described herein further comprise presenting a condition assessment area for presenting a contextually-driven assessment based on patient information relevant to diagnosing or treating the condition and determining that patient information is absent or stale in the patient health data.

In one aspect of the embodiments described herein, there is provided a system, method, or computer-readable media for providing clinical decision support, comprising: receiving a first set of information about a patient, the first set of information including one or more clinical concepts encoded in a first nomenclature; determining a second nomenclature corresponding to the first nomenclature; accessing a mapping database of mappings between the first nomenclature and the second nomenclature; translating at least a portion of the one or more clinical concepts encoded in the first nomenclature into the second nomenclature thereby creating a second set of information about the patient including one or more clinical concepts encoded in the second nomenclature; accessing a library of clinical condition programs, each clinical condition program associated with a set of clinical concept risk factors encoded in the second nomenclature; determining one or more clinical conditions associated with the patient based on the second set of patient information and based on at least one of the clinical condition programs; translating into the first nomenclature the determined one or more clinical conditions and set of risk factors associated with the condition program corresponding to each of the one or more clinical conditions; presenting a user interface including a menu of condition items, each condition item corresponding to the determined one or more clinical conditions, wherein the conditions are presented using the first nomenclature; and responsive to selecting an item in the menu, displaying a risk score for the patient having the condition corresponding to the item, and displaying a set of risk factors relevant to the risk score, wherein the risk factors are presented in the first nomenclature. In an embodiment, mapping entries of the mapping database are determined by one or more software agents.

In one aspect of the embodiments described herein, there is provided a system, method, or computer-readable media for providing clinical decision support, comprising: receiving a search query comprising one or more search terms; from a first nomenclature of clinical concept-codes, determining a first nomenclature concept-code associated with each of the one or more search terms; from a second nomenclature of clinical concept-codes, determining a second nomenclature concept-code corresponding to a first nomenclature concept code, for each of the determined first-nomenclature concept codes, thereby forming a set of second nomenclature concept-codes; performing a search query based on the set of second nomenclature concept-codes; receiving from the search query a set of search results including result concepts that are coded based on the second nomenclature of clinical concept-codes; for each of the result concepts, determining a concept-code from the first nomenclature that corresponds to result concept code based on the second nomenclature; and providing the set of search results including the result concepts, wherein the result concepts are coded based on the first nomenclature of concept codes.

In an embodiment of the systems, methods, and computer-readable media, described herein, determining a second nomenclature concept-code corresponding to a first nomenclature concept code comprises: accessing a mapping database of mappings between the first nomenclature and the second nomenclature; and translating the first nomenclature concept code to the second nomenclature concept code based information in the mapping database. In an embodiment of the systems, methods, and computer-readable media, described herein, the search query comprises information about a first patient and the set of search results include information associated with one or more second patients having at least a portion of clinical information in common with the first patient, and/or the search query comprises information about a first care giver or first health care entity associated with a first patient and the set of search results include information associated with one or more second care givers or second health care entities having at least a portion of information in common with the first care giver or first health care entity. In an embodiment, the search query is received by a user interface. In an embodiment, the user interface comprises a set of user-interface elements including: (a) a clinical conditions menu for presenting a set of clinical conditions, each of the presented clinical conditions having a corresponding clinical condition program used for determining a condition risk score indicative of a probability that the patient has the clinical condition, wherein the presented set of clinical conditions are determined based on a treatment-session context; (b) a clinical condition risk area for presenting, responsive to a selection of a given clinical condition from the menu: (i) a condition risk score representing the patient's risk for having the given clinical condition, the score determined from the corresponding clinical condition program; (ii) a set of risk factors used by the clinical condition program for determining the condition risk score; and (iii) for at least a portion of the risk factors, a clinical value for the factor, the value determined from information derived from the patient; and (c) a clinical information area for presenting a plurality of clinical information elements associated with the given clinical condition, the elements populated with clinical values for the patient from a health record, wherein the plurality of elements presented is determined based on the condition care program and organizationally presented based on a treatment-session context.

In an embodiment of the systems, methods, and computer-readable media, described herein, the search query is received by selecting one or more user interface elements or portions of one or more user interface elements, and wherein the one or more user interface elements or portions of one or more user interface elements comprise the one or more search terms, and in an embodiment, selecting one or more user interface elements comprises one or more of clicking, right-clicking, lassoing, touching, or hovering over the one or more user interface elements or portions of one or more user interface elements.

In an embodiment of the systems, methods, and computer-readable media, described herein, the search query comprises information including one or more clinical conditions associated with first patient and the set of search results include information including one or more clinical conditions associated with a second patient having at least a portion of clinical information in common with the first patient; a medical event comprises one or more of admission or readmission to a health care facility, change in patient health status, sudden injury, patient treatment, patient reaction, patient response, treatment interaction, or other health care related event affecting the first patient; and/or the search query comprises information including one or more possible future clinical conditions associated with first patient and the set of search results include information including one or more clinical conditions associated with a second patient having at least a portion of clinical information in common with the first patient.

In one aspect of the embodiments described herein, there is provided a system for providing clinical decision support, comprising: one or more processors coupled to a computer storage medium, the computer storage medium having stored thereon a plurality of computer software components executable by the processor, the computer software components comprising: a query component that receives a search query comprising one or more search terms; a code component that determines, from a first nomenclature of clinical concept-codes, a first nomenclature concept-code associated with each of the one or more search terms; wherein the code component further determines, from a second nomenclature of clinical concept-codes, a second nomenclature concept-code corresponding to a first nomenclature concept-code, for each of the determined first-nomenclature concept codes, thereby forming a set of second nomenclature concept-codes; a search component that performs a second search query based on the set of second nomenclature concept-codes; a results component that receives, from the search component, a set of search results including result concepts that are coded based on the second nomenclature of clinical concept-codes; a concept-code component that determines, for each of the result concepts, a concept-code from the first nomenclature that corresponds to result concept code based on the second nomenclature; and a presentation component that provides the set of search results including the result concepts, wherein the result concepts are coded based on the first nomenclature of concept codes.

Some embodiments described herein further comprise a menu component that presents a set of clinical conditions, each of the presented clinical conditions having a corresponding clinical condition program used for determining a condition risk score indicative of a probability that the patient has the clinical condition, wherein the presented set of clinical conditions are determined based on a treatment-session context.

Some embodiments described herein further comprise a risk component that presents, responsive to a selection of a given clinical condition presented by the menu component: a condition risk score representing the patient's risk for having the given clinical condition, the score determined from the corresponding clinical condition program; a set of risk factors used by the clinical condition program for determining the condition risk score; and for at least a portion of the risk factors, a clinical value for the factor, the value determined from information derived from the patient; and a clinical information area for presenting a plurality of clinical information elements associated with the given clinical condition, the elements populated with clinical values for the patient from a health record, wherein the plurality of elements presented is determined based on the condition care program and organizationally presented based on a treatment-session context.

Some embodiments described herein further comprise a mapping component that accesses a mapping database of mappings between the first nomenclature and the second nomenclature; and/or a translation component that translates the first nomenclature concept code to the second nomenclature concept code based information in the mapping database.

In one aspect of the embodiments described herein, there is provided a system, method, or computer-readable media for providing clinical decision support, comprising: presenting a first clinical user interface associated with a first patient having a condition, the first clinical user interface including: (a) a clinical information area having a plurality of clinical information elements, at least a portion of the plurality of clinical information elements being populated with stored clinical information associated with the first patient; (b) a clinical recommendations area for presenting a clinical recommendation associated with the condition; and/or (c) a user-input area for receiving user commands. In an embodiment, further comprising: receiving a command to initiate a clinical decision support event associated with the first patient; associating the clinical decision support event with the condition; determining a change in the condition of first patient; identifying a second patient having the condition of the first patient; and based on the clinical decision support event associated with the first patient and the determined change in the condition of the first patient, determining a clinical recommendation for the second patient.

Some embodiments described herein further comprise presenting a second clinical user interface associated with the second patient; and presenting the clinical recommendation for the second patient in the second user interface. Some embodiments described herein further comprise determining a user's response to the recommendation for the second patient and logging information indicating the user's response.

In an embodiment of the systems, methods, and computer-readable media, described herein, the clinical recommendation includes clinical concepts encoded using a proprietary vocabulary; the received command is received in a first nomenclature and the clinical recommendation includes clinical concepts encoded in a second nomenclature; and/or clinical concepts associated with the first patient are encoded in a first nomenclature and clinical concepts associated with the second patient are encoded in a second nomenclature. In an embodiment of the systems, methods, and computer-readable media, described herein, identifying a second patient having a condition of the first patient comprises: determining a first set of clinical concept codes associated with the condition of the first patient; the first set of codes being encoded in a first nomenclature; determining a second set of clinical concept codes that correspond to the first set of concept codes, the second set of codes being encoded in a second nomenclature; and from a set of patient health records for one or more patients other than the first patient, identifying a second patient having clinical concept codes matching the second set of clinical concept codes.

In one aspect of the embodiments described herein, there is provided a system, method, or computer-readable media for providing clinical decision support, comprising: presenting a first clinical user interface associated with a first patient having a condition, the first clinical user interface including: (a) a clinical information area having a plurality of clinical information elements, at least a portion of the plurality of clinical information elements being populated with stored clinical information associated with the first patient; (b) a clinical recommendations area for presenting a clinical recommendation associated with the condition; and/or (c) a user-input area for receiving user commands. In an embodiment, further comprises: receiving a command to initiate a clinical support event associated with a first patient, the command being encoded using a first clinical nomenclature; associating the clinical decision event with a clinical condition; determining a change in the first patient's condition; storing a first set of information for the first patient indicative of the event, the association with the condition, and the change in condition, the information encoded in a first clinical nomenclature; determining a second nomenclature corresponding to the first nomenclature; translating the first set of information encoded in the first nomenclature into a second set of information encoded in the second nomenclature; and storing the second set of information in a health records database.

Some embodiments described herein further comprise removing identifying information from the second set of information thereby forming de-identified information. In an embodiment of the systems, methods, and computer-readable media described herein, translating the first set of information encoded in the first nomenclature into a second set of information encoded in the second nomenclature comprises accessing a mapping database of mappings between the first nomenclature and the second nomenclature. An embodiment further comprises: identifying a second patient having the condition of the first patient; based on the second set of information, determining a clinical recommendation for the second patient; and presenting the clinical recommendation for the second patient.

In one aspect of the embodiments described herein, there is provided a system, method, or computer-readable media for providing clinical decision support, comprising: identifying a first set of patients from a set of patient caregivers, the first set of patients having in common a first set of clinical concepts; monitoring the set of patients to determine a change in condition of each patient in the first set of patients; identifying a second set of patients from a target caregiver; the second set of patients having in common a the first set of clinical concepts; for each patient in the second set of patients: (a) monitoring the patient to determine a change in condition; and (b) comparing a change in condition of the patient with changes in condition of patients in the first set of patients; based on the comparison for each patient in the second set of patients, determining a treatment score for the target caregiver. In an embodiment, the comparison is based on an average change in patient conditions for patients in the first set of patients; monitoring comprises tracking treatment costs (including financial, risk, and resources) associated with the patient, and the comparison includes a comparison of treatment cost information.

In one aspect of the embodiments described herein, a system is provided for clinical decision support comprising: one or more processors coupled to a computer storage medium, the computer storage medium having stored thereon a plurality of computer software components executable by the processor, the computer software components comprising: a first set component that identifies a first set of patients from a set of patient caregivers, the first set of patients having in common a first set of clinical concepts; a first monitor component that monitors the first set of patients to determine a change in condition of each patient in the first set of patients; a second set component that identifies a second set of patients from a target caregiver, the second set of patients having in common the first set of clinical concepts; a second monitor component that, for each patient in the second set of patients, monitors the patient to determine a change in condition; a comparison component that compares a change in condition of each patient in the second set of patients with changes in condition of patients in the first set of patients; and a treatment score component that, based on the comparison for each patient in the second set of patients, determines a treatment score for the target caregiver.

Some embodiments described herein further comprise an event component that receives a command to initiate a clinical decision support event associated with the first set of patients; an association component that associates the clinical decision support event with the first set of clinical concepts; and a recommendation component that, based on the clinical decision support event associated with the first set of patients and the changes in condition of patients in the first set of patients, determines a clinical recommendation for each patient in the second set of patients. Some embodiments further comprise a first nomenclature component that stores a first set of information for the first set of patients indicative of the clinical decision support event, the association with the first set of clinical concepts, and the changes in condition of patients in the first set of patients, the first set of information encoded in a first nomenclature; and some embodiments further comprise a second nomenclature component that determines a second nomenclature corresponding to the first nomenclature. Some embodiments further comprise: a translation component that translates the first set of information encoded in the first nomenclature into a second set of information encoded in the second nomenclature, wherein the translation component accesses a mapping database of mappings between the first nomenclature and the second nomenclature. Some embodiments further comprise a store component that stores the second set of information in a health records database, wherein identifying information is removed from the second set of information thereby forming de-identified information.

In one aspect of the embodiments described herein, there is provided a system, method, or computer-readable media for providing clinical decision support, comprising: receiving unstructured health-related data associated with a first patient, the health related data including a discrete element; identifying a preliminary match between the discrete element and a candidate clinical concept encoded in a first nomenclature; determining a first-patient set of clinical concepts associated with the first patient; receiving structured health-related data associated with a population of patients the structured health related data including, for each patient in the population, a set of clinical concepts matching the first-patient set of clinical concepts; determining a likelihood of patients in the population also having the candidate clinical concept; and based on the determined likelihood, determining that the discrete element matches the candidate clinical concept. Some embodiments described herein further comprise determining the discrete element from the received unstructured health related data using a natural language processing service.

In an embodiment of the systems, methods, and computer-readable media, described herein, natural language processing service uses an open-source natural language processing system; the natural language processing service is carried out by one or more software agents; the received unstructured health-related data comprises received audio or speech data; the received unstructured health-related data comprises data from a monitor or sensor associated with the first patient; and/or the received unstructured health-related data is received from the first patient. Some embodiments described herein further comprise presenting information about the discrete element and candidate clinical concept to a user for confirming a match; and receiving a confirmation from the user that the discrete element matches the candidate clinical concept.

In one aspect of the embodiments described herein, there is provided a system, method, or computer-readable media for providing clinical decision support, comprising: receiving unstructured patient health related data; processing the unstructured data to determine one or more clinical concepts from the unstructured data, at least one of the concepts corresponding to a clinical condition of the patient, wherein the concepts encoded are in a first nomenclature; associating the clinical concepts with each other, thereby forming a set of associated clinical concepts; determining a second nomenclature corresponding to the first nomenclature; translating the set of associated clinical concepts into the second nomenclature; storing the set of associated clinical concepts in the second nomenclature; from a database of health records, determining one or more similar sets of associated clinical concepts; and designating the clinical concepts as a contextual ontology for the clinical condition.

In an embodiment of the systems, methods, and computer-readable media, described herein, processing the unstructured data to determine one or more clinical concepts comprises using a natural language processing service; the natural language processing service uses an open-source natural language processing system; and/or the natural language processing service is carried out by one or more software agents.

In one aspect of the embodiments described herein, there is provided a system for providing clinical decision support comprising one or more processors coupled to a computer storage medium, the computer storage medium having stored thereon a plurality of computer software components executable by the processor, the computer software components comprising: an unstructured data component that receives unstructured health-related data associated with a first patient, the health related data including a discrete element; a match component that identifies a preliminary match between the discrete element and a candidate clinical concept encoded in a first nomenclature; a concept component that determines a first-patient set of clinical concepts associated with the first patient; a structured data component that receives structured health-related data associated with a population of patients the structured health related data including, for each patient in the population, a set of clinical concepts matching the first-patient set of clinical concepts; a likelihood component that determines a likelihood of patients in the population also having the candidate clinical concept; and a determination component that, based on the determined likelihood, determines that the discrete element matches the candidate clinical concept.

Some embodiments described herein further comprise a processing component that determines the discrete element from the received unstructured health related data, and in an embodiment, the processing component utilizes natural language processing. Some embodiments described herein further comprise a presentation component that presents information about the discrete element and candidate clinical concept to a user for confirming a match; and/or a confirmation component that receives a confirmation from the user that the discrete element matches the candidate clinical concept.

In one aspect of the embodiments described herein, there is provided a system, method, or computer-readable media for providing clinical decision support, comprising: from a first sequence of past clinical events relating to a patient; determining a clinical event pattern associated with the patient; from health record data associated with a population of patients, determining a set of patient health records that include the clinical event pattern; and for each member in the set of patient health records, determining a second sequence of clinical health events succeeding the clinical event pattern thereby forming a set of second sequences of clinical health events.

Some embodiments described herein further comprise based on the set of second sequences, determining a likelihood of a future health care event for the patient; recommending a health care action to take based on the likelihood of the future event; and/or for each member of the set of second sequences of clinical health events, determining a cost associated with the sequence; determining a measure of improvement in the health condition at the end of the sequence as indicated by the health record associated with each sequence; and ranking the members of the set of sequences based on the measure of improvement and cost. Some embodiments described herein further comprise recommending a care treatment sequence for the patient based on the ranking.

In one aspect of the embodiments described herein, there is provided a system, method, or computer-readable media for providing clinical decision support, comprising: determine that patient has a probability for clinical event; determining that patient is missing clinical data needed for increasing or decreasing the determined event probability; determining that clinical information is not currently available for one or more of the clinical information elements relevant to the decision support event; identifying a set of patients having similar clinical concepts associated with the condition; imputing values for target patient's clinical data based on set of patients clinical data; and using the imputed data to determine an updated probability for the clinical event. Some embodiments described herein further comprise providing an indication of the difference in target patient's EHR between actual patient data and imputed data, such as presenting imputed data in a color different than the actual patient data.

In one aspect of the embodiments described herein, there is provided a system, method, or computer-readable media for providing clinical decision support, comprising: for a patient, determining a pattern of clinical events (which may include one or more epochs); from a population of patients, identifying a set of patient records with similar pattern of clinical events; for each record, determining a series of events preceding the pattern thereby forming a future event series for each record; and designating frequently occurring event as a trigger. In an embodiment, two or more records of the set of records are in different nomenclatures.

Some embodiments described herein further comprise clustering the patient records by their change in condition. Some embodiments described herein further comprise for each cluster of records, determining a frequently occurring events among the future event series, thereby forming a frequently occurring set associated with each record cluster; and/or designating frequently occurring event a critical juncture, or critical epoch. Some embodiments described herein further comprise alerting caregiver of critical juncture thereby facilitating increased attention may be administered to patient. Some embodiments described herein further comprise determining additional clinical information for the patient to determine a probability that a future event will occur. In an embodiment, determining additional clinical information includes providing a patient assessment such as described in connection to FIG. 5E, for determining at least a portion of the additional clinical information, wherein the patient assessment is generated based on a treatment-session context.

Some embodiments described herein further comprise based on the frequently occurring events for each cluster, determining a recommendation for a target patient; selecting recommended care-pathway to execute, wherein the care-pathway comprises a treatment program; and/or determining a degree of similarity between a target patient and the set of patient records; and based on the degree of similarity, determining a probability that the target patient will have one or more of the events in the future event series. Some embodiments described herein further comprise determining a cost associated with each future event series.

In one aspect of the embodiments described herein, there is provided a system, method, or computer-readable media for providing clinical decision support, comprising: receiving a first set of clinical information associated with a patient from a data store; based on the first set of clinical information, determining a preliminary likelihood of a clinical decision support event being associated with the patient; determining that additional clinical information is not currently available for one or more clinical information factors relevant to the clinical decision support event; providing or generating a patient assessment for determining at least a portion of the additional clinical information, wherein the patient assessment is generated based on a treatment-session context; and providing the patient assessment to a health care provider treating the patient.

In an embodiment of the systems, methods, and computer-readable media, described herein, treatment-session context is determined based on at least one of the health care provider's role or clinical specialty, a clinical treatment-session venue, and the clinical decision support event, such as the clinical condition(s) of the patient. Some embodiments described herein further comprise receiving the at least a portion of the additional clinical information in response to providing the assessment, and updating the likelihood of a clinical decision support event based on the received additional clinical information; determining clinical advice or a clinical recommendation (such as described in connection to FIG. 1E), based on the likelihood of a clinical decision support event; and/or receiving the at least a portion of the additional clinical information in response to providing the assessment, and updating the determined clinical advice based on the received additional clinical information.

In an embodiment of the systems, methods, and computer-readable media, described herein, the assessment is provided via a graphical user interface; the assessment comprises a series of questions, wherein an answer for a first question, received via the user interface, determines a subsequent question in the series of questions; and/or the additional clinical information includes clinical concepts encoded in a first nomenclature. Some embodiments described herein further comprise determining clinical advice or recommendation based on the received answer to a first question or series of questions, and presenting the clinical advice in proximity to the first question or series of questions.

In one aspect of the embodiments described herein, there is provided a system, method, or computer-readable media for providing clinical decision support, comprising: receiving a first set of clinical information associated with a patient from a data store; based on the first set of clinical information, determining a likelihood of a clinical decision support event being associated with the patient; accessing an assessment associated with the clinical decision support event, the assessment including a set of patient related questions; determining from the set of questions a portion of the questions to include in a questionnaire, based on a treatment-session context and the first set of clinical information; generating a user interface for presenting the questionnaire; presenting the user interface to a user; and receiving a set of answers, via one or more clinical information elements of the user interface, in response to the portion of questions in the questionnaire. Some embodiments described herein further comprise based on the set of answers, determining an additional portion of questions from the set of questions to include in the questionnaire, and presenting the additional portion of questions.

Some embodiments described herein further comprise receiving a second set of answers to the additional portion of questions, determining clinical advice based on the first and second answers and the first set of clinical information; and presenting the clinical advice to the user. Some embodiments described herein further comprise determining a clinical concept code associated with a first question and a first answer received in response to the first question; and storing the concept code in the first set of clinical information.

In an embodiment of the systems, methods, and computer-readable media, described herein, the set of questions are determined based on health records for a population of patients, wherein each health record includes information corresponding to the clinical decision support event. In an embodiment, the set of questions is further determined based on frequently occurring clinical concepts in the health records; and/or the set of questions is determined by a health care software agent.

In one aspect of the embodiments described herein, there is provided a system, method, or computer-readable media for providing clinical decision support, comprising: receiving a target set of clinical information associated with a target population of patients from a first set of records of a first health-records system, the target set of clinical information including codified clinical concepts; receiving a reference set of clinical information associated with a reference population of patients from a second set of records of a second health-records system, the reference set of clinical information including codified clinical concepts; based on the reference set of clinical information, determining a clinical decision support event common to the records in the reference population of patients; determining frequent item-sets of the clinical concepts associated with the reference population; associating the frequent item-sets of clinical concepts with the clinical decision support event; performing a statistical comparison between the frequent item-sets and the clinical concepts of the target set of clinical information to determining a statistical measure of association between the frequent item-sets and the clinical concepts of the target set; and based on the statistical measure of association, determining a probability that the target population of patients includes the clinical decision support event.

In an embodiment of the systems, methods, and computer-readable media, described herein, performing a statistical comparison comprises: performing a distance based, similarity, or cluster-based matching of the frequent item-sets and the target set of clinical information to determine one or more clusters; determining at least one measure quantifying difference for at least one cluster; and determining a statistical measure of association based on the quantifying difference. In an embodiment, the clinical decision support event comprises a health condition, combination or health conditions or clinical procedures; clinical concepts are codified using a standardized clinical nomenclature; and/or the target and reference sets of clinical information are encoded using different nomenclatures.

In one aspect of the embodiments described herein, there is provided a system, method, or computer-readable media for providing clinical decision support, comprising: receiving a reference set of clinical information associated with a reference population of patients from a plurality of health-records systems; the reference set of clinical information including codified clinical concepts; based on the reference set of clinical information, determining a clinical decision support event common to patients in the reference population of patients; from the reference set of clinical information, determining one or more sets of frequently-occurring clinical concepts; and associating the one or more sets of frequently occurring clinical concepts with the clinical decision support event thereby forming one or more event indicators for the clinical decision support event.

Some embodiments described herein further comprise receiving a set of clinical information associated with a first patient, the clinical information including codified clinical concepts; determining a number of the indicators in set of clinical information; and based on the number of indicators, determining a likelihood that the first patient has the clinical decision support event. Some embodiments described herein further comprise presenting the determined likelihood to a user; determining a recommended clinical order for the patient based on the determined likelihood that the first patient has the clinical decision support event; generating an update for a condition care program associated with the clinical decision support event, the update including the one or more event indicators; determining the presence of the one or more event indicators in a specific patient's health record; and based on the determined presence of the one or more event indicators, determining a probability that a specific patient has a clinical decision support event.

In an embodiment of the systems, methods, and computer-readable media, described herein, the recommended clinical order is determined based on the reference set of clinical information associated with a reference population; and/or determining one or more sets of frequently-occurring clinical concepts is determined using a software agent.

In one aspect of the embodiments described herein, there is provided a system, method, or computer-readable media having computer usable instructions embodied thereon for presenting one or more user interfaces for facilitating clinical decision support, the one or more user interfaces comprising: (a) a clinical conditions menu for presenting a set of clinical conditions, each of the presented clinical conditions having a corresponding clinical condition program used for determining a condition risk score indicative of a probability that the patient has the clinical condition, wherein the presented set of clinical conditions are determined based on a treatment-session context; (b) a clinical condition risk area for presenting, responsive to a selection of a given clinical condition from the menu: (i) a condition risk score representing the patient's risk for having the given clinical condition, the score determined from the corresponding clinical condition program; (ii) a set of risk factors used by the clinical condition program for determining the condition risk score; and (iii) for at least a portion of the risk factors, a clinical value for the factor, the value determined from information derived from the patient; and/or (c) a clinical information area for presenting a plurality of clinical information elements associated with the given clinical condition, the elements populated with clinical values for the patient from a health record, wherein the plurality of elements presented is determined based on the condition care program and organizationally presented based on a treatment-session context.

In an embodiment of the systems, methods, and computer-readable media, described herein, the clinical condition program is accessed from a remote server, and may be downloaded to the client, may reside on the server, or operate in the cloud. In an embodiment, the condition program is based on healthcare information obtained from a plurality of patient health records from at least two record systems having distinct clinical nomenclatures. In an embodiment the presented condition risk score and set of risk factors are dynamically responsive to changes in the corresponding condition care program. In an embodiment, the clinical information elements are presented in a proprietary clinical nomenclature, and in an embodiment, the treatment-session context is based on at least one of a user-caregiver's clinical specialty, a clinical treatment venue, the given clinical condition, and the condition care program.

Some embodiments described herein further comprise a condition assessment area for presenting a contextually-driven assessment based on patient information relevant to diagnosing or treating a condition and receiving patient information in response to presenting the assessment, wherein the received information including one or more clinical concepts encoded in a first clinical nomenclature. Some embodiments described herein further comprise a condition assessment area for presenting a contextually-driven assessment based on patient information relevant to diagnosing or treating a condition and determining the patient information is absent or stale in the patient health data.

Some embodiments of the systems, methods, and computer-readable media, described herein further comprise determining a change in the set of risk factors used for determining a condition risk score of a condition; based on the determined change, updating the condition program corresponding to the condition; and dynamically updating the clinical condition risk area of the one or more user interfaces, in response to updating the condition program. In an embodiment updating the clinical condition risk area includes updating the presented condition risk score or presented set of risk factors; and/or determining a change in the set of risk factors comprises determining the set of risk factors includes a new or additional risk factor. Some embodiments described herein further comprise displaying an indication that the presented condition risk score or presented set of risk factors have changed; and some embodiments further comprise displaying an indication that a new risk factor has been added. In an embodiment the presented menu is dynamically responsive to changes in condition care programs or changes in the patient's clinical information associated with the patient.

Some embodiments of the systems, methods, and computer-readable media, described herein further comprise determining that a set of patient data corresponding to the determined change in the set of risk factors used for determining the condition risk score is absent in the health record; and providing a notice to a caregiver that the set of patient data is not in the health record. Some embodiments further comprise: providing or generating an assessment for obtaining the set of patient data; and presenting the assessment in a condition assessment area of the user interface.

Some embodiments of the systems, methods, and computer-readable media, described herein further comprise determining that a set of clinical values for the patient corresponding to the determined change in the set of risk factors used for determining the condition risk score is absent in the health record; and imputing values for the absent set of clinical values for the patient based on a second set of clinical values of health records of a plurality of other patients having a set of clinical concepts associated with the condition in common with the patient.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more computer-readable storage devices having computer-usable instructions embodied thereon that, when executed by a processor, perform a method for discovering and validating latent relationships in a health care dataset, the method comprising:

receiving, at a multi-agent system, a target set of clinical information associated with a target population of patients from a first set of records of a first health-records system, the target set of clinical information including a first plurality of codified clinical concepts;

receiving, at the multi-agent system, a reference set of clinical information associated with a reference population of patients from a second set of records of a second health records system, the reference set of clinical information including a second plurality of codified clinical concepts;

based on the reference set of clinical information and one or more reference sensor indications of a reference patient in the reference population, determining, at the multi-agent system, a probable future clinical decision support event that is common after at least a first time period after the one or more reference sensor indications in the second set of records for the reference population of patients and clustering the second set of records for the reference population of patients based on a change in condition;

discovering, at the multi-agent system, frequent item-sets among the second set of patients that are clustered based on the change in condition;

associating, at the multi-agent system, the frequent item-sets with the probable future clinical decision support event;

training a machine learning agent of the multi-agent system to determine a reference predicate vector pattern associated with a decision epoch for the probable future clinical decision support event based on the reference set of clinical information and on the one or more reference sensor indications of a reference patient in the reference population, wherein the decision epoch represents a future time instance that is also occurring prior to the probable future clinical decision support event;

receiving, at the multi-agent system, sensor information from a sensor coupled to at least one target patient;

based on a change in a target vector element associated with the sensor information, determining, utilizing the trained machine learning agent of the multi-agent system, an onset of the decision epoch based on determining a distance metric between the target vector element and a reference predicate vector from the reference predicate vector pattern;

based on the onset of the decision epoch, automatically and dynamically determining, at the multi-agent system, an altered course of care for the at least one target patient from the target population of patients; and causing for display, by the multi-agent system, within an interface, the altered course of care for the at least one target patient from the target population of patients by:
(1) notifying one of the following of the probable future clinical decision support event: (i) a target patient among the target population of patients, (ii) a health care professional, and (iii) a medical organization; and
(2) providing an indication of one or more alternative clinical recommendations within the decision epoch.

2. The computer readable storage devices of claim 1 wherein performing a statistical comparison comprises:
performing cluster-based matching of the frequent itemsets and the target set of clinical information to determine one or more clusters;
determining at least one measure quantifying difference for at least one cluster; and
determining a statistical measure of association based on the quantifying difference.

3. The computer readable storage devices of claim 1, wherein the probable future clinical decision support event comprises a health condition.

4. The computer readable storage devices of claim 1, wherein the probable future clinical decision support event comprises a combination of health conditions or clinical procedures.

5. The computer readable storage devices of claim 1, wherein the clinical concepts are codified using a standardized clinical nomenclature.

6. The computer readable storage devices of claim 1, wherein the target and reference sets of clinical information are encoded using different nomenclatures.

7. Computer-readable storage devices having computer-executable instructions embodied thereon that, when executed, facilitate a method for providing clinical decision support, the method comprising:
receiving, at a multi-agent system, a reference set of clinical information associated with a reference population of patients from a plurality of health-records systems, the reference set of clinical information including codified clinical concepts;
based on the reference set of clinical information and one or more reference sensor indications of a reference patient in the reference population, determining, at the multi-agent system, a probable future clinical decision support event that is common after at least a first time period after the one or more reference sensor indications to patients in the reference population of patients and clustering a set of records for the reference population of patients based on a change in condition;
determining, at the multi-agent system, one or more sets of frequently-occurring clinical concepts among the clustered set of the reference population of patients; and
associating, at the multi-agent system, the frequently-occurring clinical concepts with a decision epoch;
training a machine learning agent of the multi-agent system to determine a reference predicate vector pattern associated with a decision epoch for the probable future clinical decision support event based on the reference set of clinical information and on the one or more reference sensor indications of a reference patient in the reference population, wherein the decision epoch represents a future time instance that is also occurring prior to the probable future clinical decision support event;

receiving, at the multi-agent system, sensor information from a sensor coupled to at least one target patient;

based on a change in a target vector associated with the sensor information, determining, utilizing the trained machine learning agent of the multi-agent system, an onset of the decision epoch for the at least one target patient based on determining a distance metric between the target vector element and a reference predicate vector from the reference predicate vector pattern;

based on the onset of the decision epoch, automatically and dynamically determining, at the multi-agent system, an altered course of care for the at least one target patient from the target population of patients; and causing for display, at the multi-agent system, within an interface, the altered course of care for the at least one target patient by:
(1) notifying one of the following of the probable future clinical decision support event: (i) the at least one target patient, (ii) a health care professional, and (iii) a medical organization; and
(2) providing an indication of one or more alternative clinical recommendations within the decision epoch.

8. The computer readable storage devices of claim 7, further comprising:
receiving a set of clinical information associated with a first patient, the clinical information including codified clinical concepts;
determining a number of the indicators in the set of clinical information; and
based on the number of indicators, determining a likelihood that the first patient has the probable future clinical decision support event.

9. The computer readable storage devices of claim 8, further comprising presenting the determined likelihood to a user.

10. The computer readable storage devices of claim 8, further comprising determining a recommended clinical order for the patient based on the determined likelihood that the first patient has the probable future clinical decision support event.

11. The computer readable storage devices of claim 10, wherein a recommended clinical order is determined based on the reference set of clinical information associated with a reference population.

12. The computer readable storage devices of claim 7, wherein determining one or more sets of frequently-occurring clinical concepts is determined using a software agent.

13. The computer readable storage devices of claim 7, further comprising generating an update for a condition care program associated with the probable future clinical decision support event, the update including the one or more event indicators.

14. The computer readable storage devices of claim 7, further comprising determining the presence of the one or more event indicators in a specific patient's health record; and based on the determined presence of the one or more event indicators, determining a probability that a specific patient has the probable future clinical decision support event.

15. Computer-readable storage devices having computer-executable instructions embodied thereon that, when executed, facilitate a method for providing clinical decision support, the method comprising:
- receiving, at a multi-agent system, patient information from a population of patients having a clinical condition, the patient information including patient records comprising one or more codified clinical concepts;
- determining, at the multi-agent system, a set of frequently occurring clinical concepts in a clustered set of the patient records for the patients in the population that are clustered based on a change in condition;
- based on the patient information and one or more reference sensor indications of a reference patient in the patient population, determining, at the multi-agent system, a probable future clinical decision support event that is common within the patient population, the probable future clinical decision support event occurring after at least a first time period after the one or more reference sensor indications;
- training a machine learning agent of the multi-agent system to determine a reference predicate vector pattern associated with a decision epoch for the probable future clinical decision support event based on the reference set of clinical information and on the one or more reference sensor indications of a reference patient in the reference population, wherein the decision epoch represents a future time instance that is also occurring prior to the probable future clinical decision support event;
- receiving, at the multi-agent system, sensor information from a sensor coupled to at least one target patient;
- based on a change in a target vector element associated with the sensor information, determining, utilizing the trained machine learning agent of the multi-agent system, an onset of the decision epoch for the target patient based on determining a distance metric between the target vector element and a reference predicate vector from the reference predicate vector pattern;
- based on the onset of the decision epoch, automatically and dynamically determining, at the multi-agent system, an altered course of care for the at least one target patient from the target population of patients; and
- causing for display, at the multi-agent system, within an interface, the altered course of care for the target patient by:
  - (1) notifying one of the following of the probable future clinical decision support event: (i) the target patient, (ii) a health care professional, and (iii) a medical organization; and
  - (2) providing an indication of a one or more alternative clinical recommendations within the decision epoch.

16. The computer readable storage devices of claim 15, further comprising determining a statistical degree of association between one or more clinical concept in a set of potential risk factors and a clinical condition.

17. The computer readable storage devices of claim 16, further comprising ranking the risk factors based on the statistical degree of association with the clinical condition.

18. The computer readable storage devices of claim 15, further comprising generating an update for a condition care program associated with the clinical condition, the update including one or more of the risk factors.

19. The computer readable storage devices of claim 18, further comprising determining the presence of one or more event indicators in a specific patient's health record; and based on the determined presence of the one or more event indicators, determining a probability that a specific patient has the clinical condition.

20. The computer readable storage devices of claim 15, wherein the clinical condition comprises a clinical decision support event.

21. The computer readable storage devices of claim 1, wherein the decision epoch concludes based on an offset of the target predicate vector element.

* * * * *

UNITED STATES PATENT AND TRADEMARK OFFICE
CERTIFICATE OF CORRECTION

| | | |
|---|---|---|
| PATENT NO. | : 10,957,449 B1 | Page 1 of 2 |
| APPLICATION NO. | : 14/148046 | |
| DATED | : March 23, 2021 | |
| INVENTOR(S) | : Douglas S. McNair et al. | |

It is certified that error appears in the above-identified patent and that said Letters Patent is hereby corrected as shown below:

On the Title Page
Column 01, (73) Assignee: After "Inc." please insert --, Kansas City, KS (US)--.
Page 03, Column 02, Other Publications, Line 14: Please remove "Eidemiological" and replace with --Epidemiological--.
Page 03, Column 02, Other Publications, Line 40: Please remove "Schook" and replace with --School--.

In the Drawings
Sheet 5 of 46, FIG. 1E.: Please remove "SEQUENCEING" and replace with --SEQUENCING--.
Sheet 6 of 46, FIG. 2A., reference numeral 2020: Please remove "DISERN" and replace with --DISCERN--.
Sheet 16 of 46, FIG. 4B., reference numeral 4170: Please remove "NOMENCALUE" and replace with --NOMENCLATURE--.

In the Specification
Column 03, Line 11: Please remove "FIG." and replace with --FIGS.--.
Column 08, Line 44: Please remove "as as" and replace with --as--.
Column 17, Line 30: Please remove "chronbach" and replace with --cronbach--.
Column 18, Line 40: Please remove "Kohenen" and replace with --Kohonen--.
Column 25, Line 51: Please remove "enroleed" and replace with --enrolled--.
Column 30, Line 27: Please remove "and or" and replace with --and/or--.
Column 30, Line 37: Please remove "and or" and replace with --and/or--.
Column 49, Line 53: Please remove "scropt" and replace with --script--.
Column 59, Line 04: Please remove "FIG." and replace with --FIGS.--.
Column 62, Line 23: Please remove "a the" and replace with --the--.

In the Claims
Column 71, Line 18: Please remove "computer readable" and replace with --computer-readable--.
Column 71, Line 27: Please remove "computer readable" and replace with --computer-readable--.
Column 72, Line 29: Please remove "computer readable" and replace with --computer-readable--.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*

Column 72, Line 39: Please remove "computer readable" and replace with --computer-readable--.
Column 72, Line 59: Please remove "computer readable" and replace with --computer-readable--.
Column 74, Line 14: Please remove "computer readable" and replace with --computer-readable--.
Column 74, Line 18: Please remove "computer readable" and replace with --computer-readable--.
Column 71, Line 21: Please remove "computer readable" and replace with --computer-readable--.